(12) United States Patent
Defauw et al.

(10) Patent No.: US 8,802,728 B2
(45) Date of Patent: Aug. 12, 2014

(54) ANALGESIC COMPOUNDS, METHODS, AND FORMULATIONS

(75) Inventors: Jean Marie Defauw, New Palestine, IN (US); Scott Dale Holmstrom, Fishers, IN (US); Shuhui Chen, Calabasas, CA (US); Yang Zhang, Shangahi (CN); Wentao Wu, Shanghai (CN); Xian Peng, Shanghai (CN); Yujuan Ma, Shanghai (CN); Lun Lu, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/883,803

(22) PCT Filed: Jan. 13, 2012

(86) PCT No.: PCT/US2012/021181
§ 371 (c)(1),
(2), (4) Date: May 7, 2013

(87) PCT Pub. No.: WO2012/102875
PCT Pub. Date: Aug. 2, 2012

(65) Prior Publication Data
US 2013/0225679 A1    Aug. 29, 2013

(30) Foreign Application Priority Data

Jan. 27, 2011   (CN) ................ PCT/CN2011/070706

(51) Int. Cl.
| | | |
|---|---|---|
| *A01N 37/00* | (2006.01) | |
| *A61K 31/21* | (2006.01) | |
| *A01N 33/02* | (2006.01) | |
| *A61K 31/135* | (2006.01) | |
| *C07C 215/00* | (2006.01) | |

(52) U.S. Cl.
USPC ............ 514/511; 514/646; 514/647; 564/443

(58) Field of Classification Search
CPC combination set(s) only.
See application file for complete search history.

(56) References Cited

U.S. PATENT DOCUMENTS

| | | |
|---|---|---|
| 3,564,100 A | 2/1971 | Frankus et al. |
| 3,652,589 A | 3/1972 | Flick et al. |
| 5,801,201 A * | 9/1998 | Graudums et al. ............ 514/646 |
| 2003/0232891 A1 | 12/2003 | Sundermann et al. |
| 2005/0182131 A1 | 8/2005 | Friderichs et al. |

FOREIGN PATENT DOCUMENTS

| | | |
|---|---|---|
| EP | 1127871 A1 | 8/2001 |
| EP | 2022778 A1 | 2/2009 |
| GB | 997399 A | 7/1965 |
| WO | 02/26694 A1 | 4/2002 |
| WO | 03/048113 A1 | 6/2003 |

OTHER PUBLICATIONS

Alvarado, Cuauhtemoc, et al., "Synthesis of tramadol and analogs," Journal of the Mexican Chemical Society, 49 (4):324-327 (Jan. 2005).

Flick, K., et al., "Untersuchungen zur chemischen struktur and analgetischen wirkung von phenylsubstituierten aminomethylcyclohexanolen. Ostudeies on chemical structure and analgetic activity of phenyl substituted aminomethylcyclohexanoles," Arzneimittel Forschung, Drug Research, ECV Editio Cantor Verlag, Aulendorf, DE, 28 (1a):107-113 (Jan. 1978).

\* cited by examiner

*Primary Examiner* — Jason Sims
*Assistant Examiner* — Tori M Strong
(74) *Attorney, Agent, or Firm* — McAndrews Held & Malloy, Ltd.

(57) ABSTRACT

Provided are analgesic compounds, and salts thereof, of formula: (I) wherein A is: (A) Additionally, pharmaceutical formulations and methods of use employing the above compounds are provided.

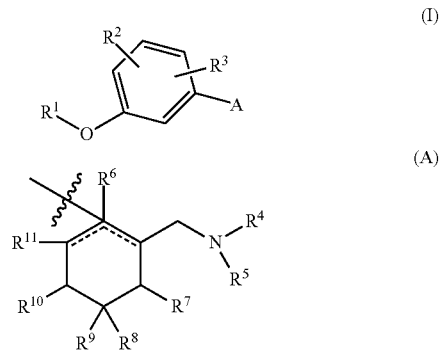

31 Claims, No Drawings

ANALGESIC COMPOUNDS, METHODS, AND FORMULATIONS

Opiates, a class of centrally acting compounds, are the most frequently used agents for pain control and alleviation, and which act upon one or more of the human or mammal opiate receptors. Technically, opiates are the natural alkaloids found in the resin of the opium poppy, but current usage of the term includes synthetic variations, termed opioids. Opiates are narcotic agonistic analgesics and are drugs including or derived from opium, such as morphine, codeine, and many synthetic congeners of morphine, with morphine and hydrocodone preparations being the most widely used opiates. Opiates are natural and synthetic drugs with morphine-like actions, and are subject to control under U.S. Federal narcotics law (scheduled drugs) and the laws of most other nations and international organizations because of their addicting properties and the subsequent destructive toll exacted on the abusers and those with any connection to them.

Tramadol is a synthetic analog of the phenanthrene alkaloid codeine and, as such, is an opioid and also a prodrug (codeine is metabolized to morphine, tramadol is converted to M-1 also called O-desmethyltramadol). Tramadol, like the opiates, is associated with adverse effects, such as physical and psychological dependence, severe withdrawal symptoms, as well as other somewhat less serious side-effects, including nausea, vomiting, sweating, constipation, and drowsiness.

While the opiates and related drugs clearly serve useful purposes, alternative therapies and compounds for alleviation of pain are desirable due to the known problems of the opiates. Particularly, compounds which are not scheduled, allow for lower dosing frequency, and/or do not exhibit the side-effects either at all or to the degree associated with the opiates and related drugs, would provide such alternative therapies.

Provided are analgesic compounds, and salts thereof, of formula I:

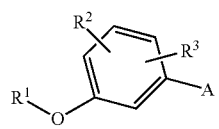

I wherein A is

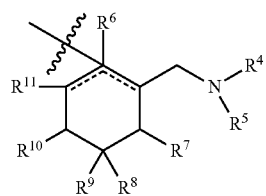

$R^1$ is hydrogen, $C_1$-$C_5$ alkyl, $C_1$-$C_5$ alkoxy, $C_1$-$C_5$ haloalkyl, $C_1$-$C_5$ alkanol, —($C_1$-$C_5$ alkyl)phenyl, or phenyl, or a group of the formula —C(O)—$R^{12}$, where $R^{12}$ may be $C_1$-$C_5$ alkyl, $C_1$-$C_5$ alkoxy, $C_1$-$C_5$ haloalkyl, $C_1$-$C_5$ alkanol, —($C_1$-$C_5$ alkyl)phenyl, or phenyl;

$R^2$ is hydrogen, $C_1$-$C_5$ alkyl, $C_1$-$C_5$ alkoxy, halogen, $C_1$-$C_5$ haloalkyl, or $C_1$-$C_5$ haloalkoxy;

$R^3$ is hydrogen, $C_1$-$C_5$ alkyl, $C_1$-$C_5$ alkoxy, halogen, $C_1$-$C_5$ haloalkyl, or $C_1$-$C_5$ haloalkoxy;

$R^4$ is hydrogen, $C_1$-$C_5$ alkyl, or —($C_1$-$C_5$ alkyl)phenyl;
$R^5$ is hydrogen, $C_1$-$C_5$ alkyl, or —($C_1$-$C_5$ alkyl)phenyl;
$R^6$ is hydrogen, hydroxy, or is absent;
$R^7$ is hydrogen;
$R^8$ is hydrogen or methyl;
$R^9$ is hydrogen or methyl;
$R^{10}$ is hydrogen;
$R^{11}$ is hydrogen or $C_1$-$C_5$ alkyl;
or $R^7$ and $R^{10}$ combine to form —$CH_2$— or —$(CH_2)_2$—;
or $R^8$ and $R^9$ combine to form a cyclopropyl group with the carbon to which they are attached;
or $R^{10}$ and $R^{11}$ combine to form —$CH_2$— or —$(CH_2)_3$—.

More particularly, A may be:

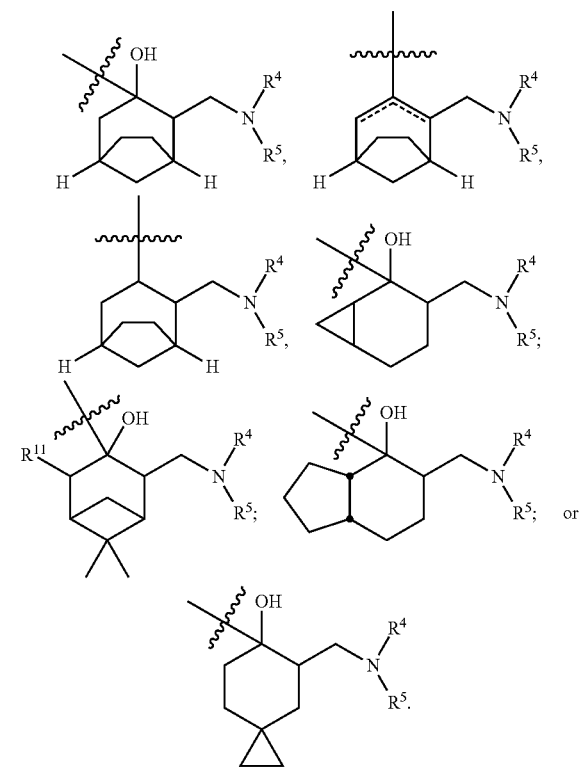

Of the first four definitions immediately above for A, the following are preferred:

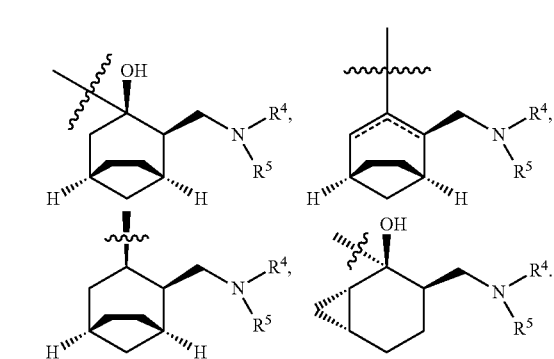

$C_1$-$C_5$ alkyl refers to straight chain and branched alkyls having one to five carbon atoms, and includes methyl, ethyl, propyl, n-butyl, iso-butyl, pentyl, isopentyl, and neopentyl.

$C_1$-$C_5$ alkoxy refers to straight chain and branched alkoxys having one to five carbon atoms, and includes methoxy, ethoxy, propoxy, n-butoxy, iso-butoxy, pentoxy, isopentoxy, and neopentoxy.

Halogen or halo refers to fluorine, bromine, chlorine, and iodine.

Haloalkyl as used herein refers to an alkyl (as noted above) substituted with one or more halo atoms. Such groups include trifluoromethyl, methylchloride, dichloromethyl, pentylchloride, butyl chloride, and isopropyl chloride.

Haloalkoxy refers to an alkoxy group, as described herein, which is substituted with one to six halo groups. Examples of fluoroalkoxy groups include fluoromethoxy, difluoromethoxy, trifluoromethoxy, pentafluoroethoxy, and trifluoroethoxy.

$C_1$-$C_5$ alkanols refer to methanol, ethanol, propanol, or methoxyethanol.

In the definition of A:

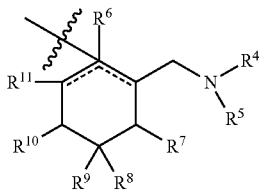

the portion

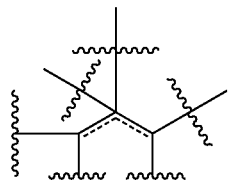

can be

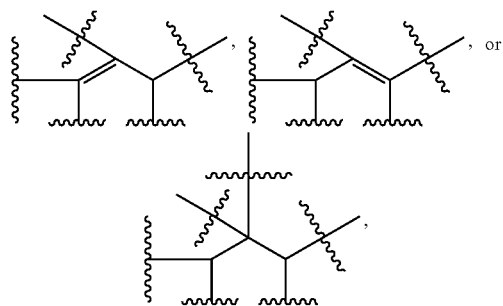

as appropriate.

PivCl refers to pivaloyl chloride.

Controlling pain refers to either suppressing, inhibiting, ameliorating, reducing, or eliminating pain, its severity, and/or duration. As such, the invention is applicable to the alleviation of existing pain as well as the suppression or inhibition of pain which would otherwise ensue from an imminent pain-causing event. The pain being alleviated can be chronic or acute.

Mammal includes both human or non-human mammals. Non-human mammals include domestic animals, such as livestock animals and companion animals. Livestock animals include cattle, camellids, pigs, sheep, goats, and horses. Companion animals include dogs, rabbits, cats, and other pets owned and maintained in close association with humans as part of the human-animal bond.

Effective amount refers to the amount of a compound of formula I, or a salt thereof, sufficient to control or alleviate pain in a mammal in need thereof, and as such will depend upon several factors. Ranges for a compound of formula I, or a salt thereof, in the methods include from 0.01 to 1000 mg/kg and more desirably, 0.1 to 100 mg/kg of the animal's body weight. The frequency of the administration will also be dependent upon several factors, and can be a single dose administered once a day or once a week for a duration determined by the attending doctor or veterinarian. The dose can be also be split into two or more smaller doses given in a timeframe to result in the control or alleviation of pain.

Pharmaceutically acceptable as used in this application, for example with reference to salts and formulation components such as carriers, includes "veterinarily acceptable", and thus includes both human and animal applications independently.

Pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. A preferred salt is the hydrochloride salt.

The compounds of formula I and their salts may be formulated as pharmaceutical compositions for systemic administration. Such pharmaceutical compositions and processes for making the same are known in the art for both humans and non-human mammals. See, e.g., REMINGTON: THE SCIENCE AND PRACTICE OF PHARMACY, (A. Gennaro, et al., eds., 19th ed., Mack Publishing Co., 1995). Additional active ingredients may be included in the formulation containing a compound of formula I or a salt thereof.

Carrier is used herein to describe any ingredient other than the active component(s) in a formulation. The choice of carrier will to a large extent depend on factors such as the particular mode of administration, the effect of the carrier on solubility and stability, and the nature of the dosage form.

The compounds of the invention may be made by the following described procedures, as well as the procedures described in Selnick, H. C.; Bourgeois, M. L.; Butcher, J. W.; Radzilowski, E. M. *Tetrahedron Lett*, 1993, 34, 2043; Alvarado, C; Guzman, A.; Diaz, E.; Patino. R. *J. Mex. Chem. Soc.* 2005, 49, 324; Evans, G. R.; Paloma, Fernandez, D.; Henshilwood, J. A.; Lloyd, S.; Nicklin, C. *Org. Process Res. Dev.* 2002, 6, 729; and Mohacsi, E.; O'Brien, J. P.; Blount, J. F. *J. Heterocycl. Chem.* 1990, 27, 1623.

The invention provides a pharmaceutical formulation comprising a compound of formula I, or a pharmaceutically acceptable salt thereof, and one or more pharmaceutically acceptable carriers. The pharmaceutical formulation may further comprise at least one additional active ingredient. A pharmaceutical formulation may be a human pharmaceutical formulation or a veterinary pharmaceutical formulation.

The invention provides a method of controlling pain in a mammal in need thereof comprising administering an effective amount of a compound of formula I, or a pharmaceutically acceptable salt thereof, to said mammal. The method may further provide administering at least one other active ingredient to said mammal. The mammal may be a human or non-human mammal, and further may be a companion animal, such as a dog or cat.

For compounds of the formula Ia, below, Schemes A-C and Preparations and/or Examples 1-76 illustrate methods of preparing them.

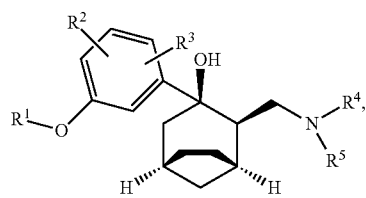

Ia

Scheme A

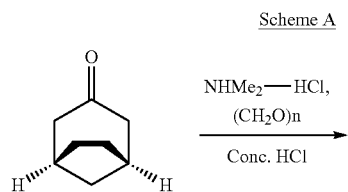

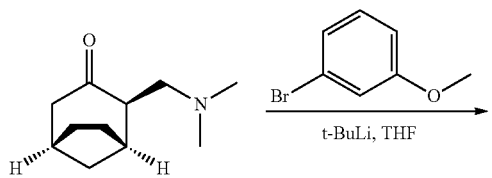

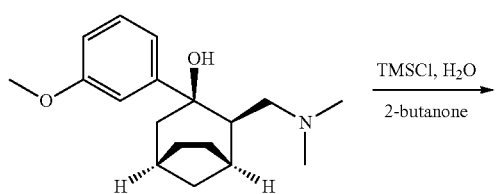

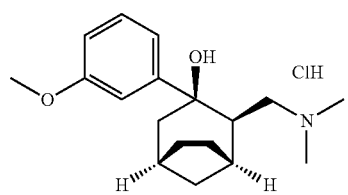

PREPARATION 1

Synthesis of 2-dimethylaminomethyl-bicyclo[3.2.1]octan-3-one

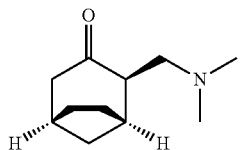

Stir a mixture of bicyclo[3.2.1]octan-3-one (5.2 g, 41.9 mmol), (HCHO)$_n$ (1.51 g, 50.3 mmol), dimethylamine hydrochloride (3.42 g, 41.9 mmol) and 0.5 mL of conc. HCl in MeCN (50 mL) at 80° C. for 2 hours. After removal of the solvent under vacuum, dissolve the residue in H$_2$O (20 mL) and wash with EtOAc (20 mL×3). Basify the aqueous solution with NaOH to pH=10. Extract the resultant aqueous mixture with EtOAc (60 mL×3). The combined organic layers are washed with brine (10 mL), dried over Na$_2$SO$_4$, filtered, and concentrated under vacuum to give crude 2-dimethylaminomethyl-bicyclo[3.2.1]octan-3-one as brown oil (5.9 g, yield: 78.7%). MS (m/z): 182 (M+1).

EXAMPLE 2

Synthesis of 2-dimethylaminomethyl-3-(3-methoxyphenyl)-bicyclo[3.2.1]octan-3-ol

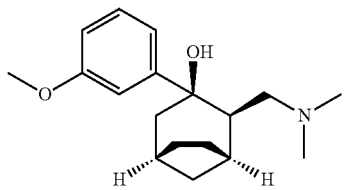

Add dropwise a solution of t-BuLi (19.2 mL, 25.0 mmol) in hexane via syringe to a solution of 1-bromo-3-methoxy-benzene (3.74 g, 20.0 mmol) in THF (60 mL) at −78° C. under N$_2$. After being stirred at −78° C. for 1 hour, add dropwise a solution of 2-dimethylaminomethyl-bicyclo[3.2.1]octan-3-one (1.81 g, 10.0 mmol) in THF (10 mL) to the reaction mixture and stir the resultant mixture at −78° C. for additional 1 hour. Quench the reaction with saturated aqueous NH$_4$Cl solution (20 mL). Extract the aqueous mixture with EtOAc (50 mL×3). The combined organic layers are washed with brine (15 mL), dried over Na$_2$SO$_4$, filtered, and concentrated under vacuum. Purify the residue by silica gel chromatography (CH$_2$Cl$_2$:MeOH=30:1) to afford 2-dimethylaminomethyl-3-(3-methoxy-phenyl)-bicyclo[3.2.1]octan-3-ol as white solid (1.49 g, yield: 51%). MS (m/z): 290 (M+1).

The following compounds may be prepared essentially by the method of Example 2.

| Ex. No. | Chemical name | Structure | Physical data |
|---|---|---|---|
| 3 | 2-Dimethylaminomethyl-3-(3-fluoro-5-methoxy-phenyl)-bicyclo[3.2.1]octan-3-ol | 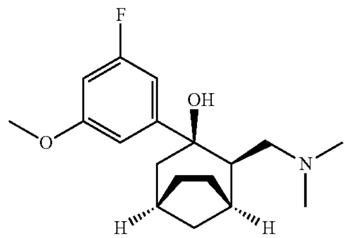 | MS (m/z): 308 (M + 1). |
| 4 | 2-Dimethylaminomethyl-3-(5-methoxy-2-trifluoro-methoxy-phenyl)-bicyclo[3.2.1]octan-3-ol | 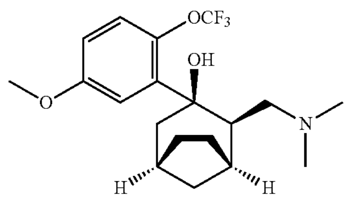 | MS (m/z): 374 (M + 1). |
| 5 | 2-Dimethylaminomethyl-3-(2-fluoro-5-methoxy-phenyl)-bicyclo[3.2.1]octan-3-ol | 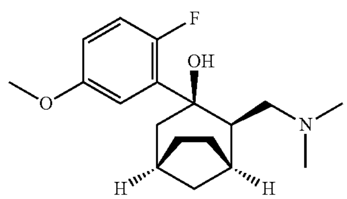 | MS (m/z): 308 (M + 1). |
| 6 | 2-Dimethylaminomethyl-3-(4-fluoro-3-methoxy-phenyl)-bicyclo[3.2.1]octan-3-ol | 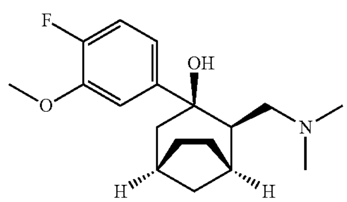 | MS (m/z): 308 (M + 1). |
| 7 | 2-Dimethylaminomethyl-3-(2-fluoro-3-methoxy-phenyl)-bicyclo[3.2.1]octan-3-ol | 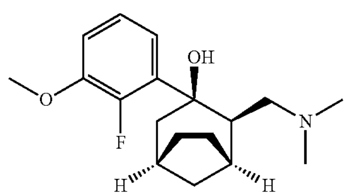 | MS (m/z): 308 (M + 1). |
| 8 | 2-Dimethylaminomethyl-3-(3-methoxy-5-methyl-phenyl)-bicyclo[3.2.1]octan-3-ol | 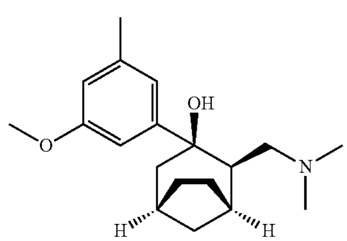 | MS (m/z): 304 (M + 1). |
| 9 | 3-(2-Chloro-5-methoxy-phenyl)-2-dimethylamino-methyl-bicyclo[3.2.1]octan-3-ol | 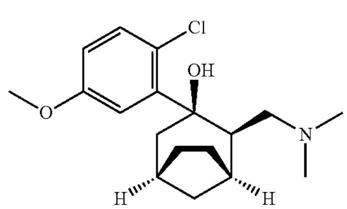 | MS (m/z): 324 (M + 1). |

| Ex. No. | Chemical name | Structure | Physical data |
|---|---|---|---|
| 10 | 3-(3-Chloro-5-methoxy-phenyl)-2-dimethylamino-methyl-bicyclo[3.2.1]octan-3-ol | 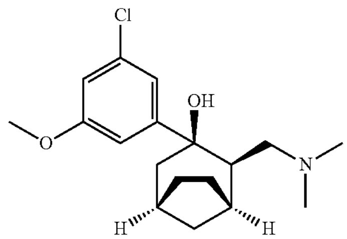 | MS (m/z): 324 (M + 1). |
| 11 | 2-Dimethylaminomethyl-3-(5-methoxy-2-methyl-phenyl)-bicyclo[3.2.1]octan-3-ol | 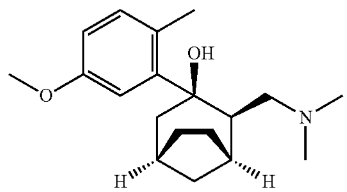 | MS (m/z): 304 (M + 1). |
| 12 | 2-Dimethylaminomethyl-3-(3-methoxy-4-methyl-phenyl)-bicyclo[3.2.1]octan-3-ol | 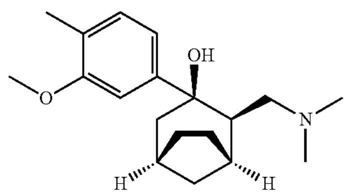 | MS (m/z): 304 (M + 1). |
| 13 | 2-Dimethylaminomethyl-3-(3-hydroxy-phenyl)-bicyclo[3.2.1]octan-3-ol | 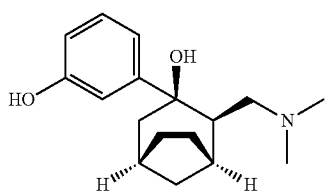 | MS (m/z): 276 (M + 1). |

EXAMPLE 14

Synthesis of 2-dimethylaminomethyl-3-(3-methoxy-phenyl)-bicyclo[3.2.1]octan-3-ol hydrochloride

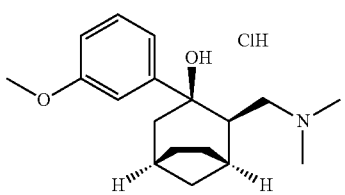

Add $H_2O$ (100 mg, 5.56 mmol) and TMSCl (361 mg, 3.34 mmol) to a solution of 2-dimethylaminomethyl-3-(3-methoxy-phenyl)-bicyclo[3.2.1]octan-3-ol (877 mg, 3.03 mmol) in 2-butanone (60 mL). Stir the mixture at ambient temperature for 12 hours. Concentrate the mixture under vacuum to give 2-dimethylaminomethyl-3-(3-methoxy-phenyl)-bicyclo[3.2.1]octan-3-ol hydrochloride as white solid (986 mg, Yield: 100%). $^1$H NMR (400 MHz, $D_2O$) δ 7.23-7.27 (t, J=16.4, 1H), 7.00-7.02 (d, J=8.0, 1H), 6.95-6.96 (t, J=4.0, 1H), 6.78-6.80 (d, J=10.4, 1H), 3.71 (s, 3H), 3.05-3.19 (m, 1H), 2.52-2.58 (m, 4H), 2.14-2.26 (m, 4H), 2.09-2.14 (m, 2H), 2.05-2.06 (d, J=2.4, 1H), 1.89-1.92 (m, 1H), 1.78-1.80 (m, 1H), 1.51-1.68 (m, 4H), 1.40-1.52 (m, 1H).

The following compounds may be prepared essentially by the method of Example 14.

| Ex. No. | Chemical name | Structure | Physical data |
|---|---|---|---|
| 15 | 2-Dimethylamino-methyl-3-(3-fluoro-5-methoxy-phenyl)-bicyclo[3.2.1]octan-3-ol hydrochloride | 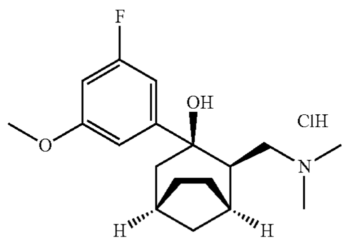 | $^1$H NMR (400 MHz, Methanol-d4) δ 6.92 (s, 1H), 6.88-6.85 (d, J = 12.0, 1H), 6.62-6.59 (d, J = 12.0, 1H), 3.82 (s, 3H), 2.80 (s, 3H), 2.74-2.70 (d, J = 16.0, 1H), 2.51-2.48 (m, 4H), 2.40 (s, 1H), 2.30-2.25 (m, 3H), 2.27-2.24 (d, J = 12.0, 2H), 2.17-2.15 (m, 1H), 1.81-1.64 (m, 4H). |
| 16 | 2-Dimethylamino-methyl-3-(5-methoxy-2-trifluoro-methoxy-phenyl)-bicyclo[3.2.1]octan-3-ol hydrochloride | 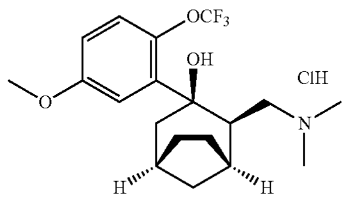 | $^1$H NMR (400 MHz,, D$_2$O) δ 7.24-7.26 (d, J = 8.4, 1H), 7.13 (s, 1H), 6.86-6.88 (d, J = 8.8, 1H), 3.73 (s, 3H), 3.11-3.17 (m, 1H), 2.65 (s, 3H), 2.48-2.55 (m, 2H), 2.18-2.39 (m, 6H), 1.92-1.94 (m, 1H), 1.60-1.75 (m, 5H), 1.48-1.56 (m, 1H). |
| 17 | 2-Dimethylamino-methyl-3-(2-fluoro-5-methoxy-phenyl)-bicyclo[3.2.1]octan-3-ol hydrochloride | 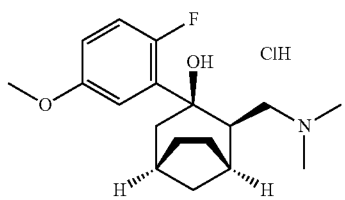 | $^1$H NMR (400 MHz, D$_2$O) δ 6.98-6.70 (m, 2H), 6.79-6.81 (m, 1H), 3.70 (s, 3H) 3.08-3.11 (t, J = 12.8, 1H), 2.55-2.62 (m, 4H), 2.25-2.48 (m, 6H), 2.17 (s, 1H), 1.85-1.94 (m, 1H), 1.49-1.57 (m, 6H). |
| 18 | 2-Dimethylamino-methyl-3-(4-fluoro-3-methoxy-phenyl)-bicyclo[3.2.1]octan-3-ol hydrochloride | 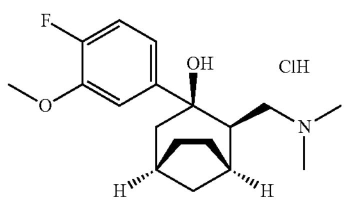 | $^1$H NMR (400 MHz, D$_2$O) δ 7.12-7.06 (m, 2H), 7.08 (s, 1H), 3.82 (s, 3H), 2.64-2.57 (m, 3H), 2.35 (m, 2H), 2.31 (s, 1H), 2.21-2.11 (m, 2H), 2.12 (s, 6H), 1.87-1.74 (m, 2H), 1.66-1.48 (m, 3H). |
| 19 | 2-Dimethylamino-methyl-3-(2-fluoro-3-methoxy-phenyl)-bicyclo[3.2.1]octan-3-ol hydrochloride | 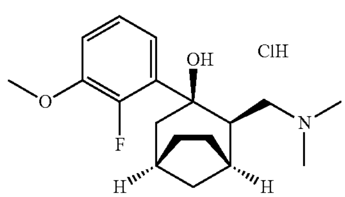 | $^1$H NMR (400 MHz, D$_2$O) δ 7.11-7.01 (m, 3H), 3.77 (s, 3H), 3.14-3.09 (m, 1H), 2.63-2.57 (m, 4H), 2.45-2.26 (m, 5H), 2.18 (s, 1H) 2.06 (s, 1H), 1.95-1.90 (m, 1H), 1.79-1.74 (m, 1H), 1.69-1.53 (m, 4H), 1.51-1.47 (m, 1H). |
| 20 | 2-Dimethylamino-methyl-3-(3-methoxy-5-methyl-phenyl)-bicyclo[3.2.1]octan-3-ol hydrochloride | 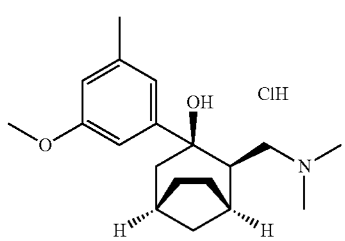 | $^1$H NMR (400 MHz, D$_2$O) δ 6.86 (s, 1H), 6.76 (s, 1H), 6.65 (s, 1H), 3.69 (s, 3H), 3.03-3.09 (m, 1H), 2.60 (s, 3H), 2.52-2.55 (d, J = 13.2, 1H), 2.33 (s, 3H), 2.14-2.24 (m, 6H), 2.04-2.08 (d, J = 14.4, 1H), 1.90-1.94 (m, 1H), 1.76-1.80 (m, 1H), 1.58-1.66 (m, 4H), 1.45-1.49 (m, 1H). |
| 21 | 3-(2-Chloro-5-methoxy-phenyl)-2-dimethylaminomethyl-bicyclo[3.2.1]octan-3-ol hydrochloride | 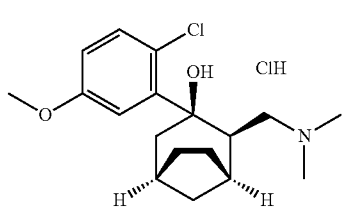 | $^1$H NMR (400 MHz, Methanol-d4) δ 7.44-7.45 (d, J = 3.2, 1H), 7.32-7.34 (d, J = 8.8, 1H), 6.86-6.89 (m, 1H), 3.73 (s, 3H), 3.27-3.30 (t, J = 13.6 1H), 3.05-3.07 (d, J = 9.2, 1H), 2.90-2.94 (m, 1H), 2.81 (s, 3H), 2.71-2.75 (d, J = 13.6, 1H), 2.47 (m, 5H), 2.29-2.35 (m, 1H), 2.03-2.12 (m, 2H), 1.59-1.79 (m, 4H). |

| Ex. No. | Chemical name | Structure | Physical data |
|---|---|---|---|
| 22 | 3-(3-Chloro-5-methoxy-phenyl)-2-dimethylaminomethyl-bicyclo[3.2.1]octan-3-ol hydrochloride | 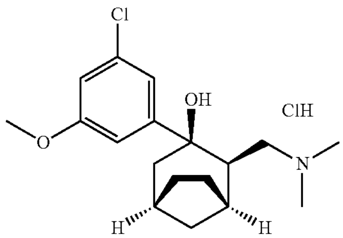 | $^1$H NMR (400 MHz, Methanol-d4) δ 7.12 (s, 1H), 7.02 (t, J = 2.0, 1H), 6.85-6.86 (t, J = 4.0, 1H), 3.82 (s, 3H), 3.36 (m, 1H), 2.68-2.71 (m, 7H), 2.36-2.37 (m, 2H), 2.25-2.28 (m, 2H), 2.14-2.18 (m, 1H), 2.03-2.09 (t, J = 23.6, 1H), 1.70-1.86 (m, 4H), 1.59-1.67 (m, 1H). |
| 23 | 2-Dimethylamino-methyl-3-(5-methoxy-2-methyl-phenyl)-bicyclo[3.2.1]octan-3-ol hydrochloride | 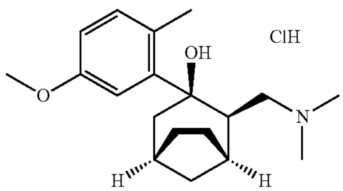 | $^1$H NMR (400 MHz, D$_2$O) δ 7.26 (s, 1H), 7.21-7.19 (d, J = 8.0, 1H), 6.88-6.86 (d, J = 8.0, 1H), 3.81 (s, 3H), 3.23-3.17 (m, 1H), 3.71-3.66 (m, 3H), 2.59-2.51 (m, 6H), 2.41 (s, 4H), 2.32 (s, 1H), 2.04-2.01 (m, 1H), 1.90-1.88 (m, 2H), 1.75-1.67 (m, 2H), 1.63-1.59 (m, 2H). |
| 24 | 2-Dimethylamino-methyl-3-(3-methoxy-4-methyl-phenyl)-bicyclo[3.2.1]octan-3-ol hydrochloride | 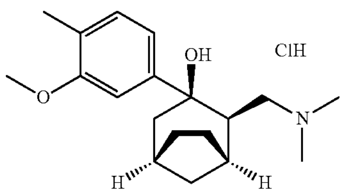 | $^1$H NMR (400 MHz, D$_2$O) δ 7.23-7.21 (d, J = 4.0, 1H), 7.05 (s, 1H), 7.03 (s, 1H), 3.85 (s, 3H), 3.22-3.18 (m, 1H), 2.71-2.64 (m, 4H), 2.42 (s, 3H), 2.36-2.27 (m, 3H), 2.20-2.16 (m, 4H), 2.08-2.02 (m, 1H), 1.94-1.90 (m, 1H), 1.88-1.75 (m, 4H), 1.60-1.56 (m, 1H). |
| 25 | 2-Dimethylamino-methyl-3-(3-hydroxy-phenyl)-bicyclo[3.2.1]octan-3-ol hydrochloride | 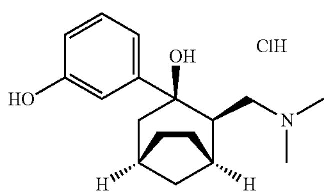 | $^1$H NMR (400 MHz, D$_2$O) δ 7.14-7.18 (t, J = 15.6, 1H), 6.91-6.93 (d, J = 7.2, 1H), 6.85 (s, 1H), 6.64-6.66 (d, J = 6.8, 1H), 3.00-3.06 (t, J = 22.8, 1H), 2.53-2.57 (m, 4H), 2.28 (s, 3H), 2.22 (s, 1H), 2.12-2.14 (m, 2H), 2.01-2.05 (d, J = 13.6, 1H), 1.90 (m, 1H), 1.76 (m, 1H), 1.60-1.65 (m, 4H), 1.45 (m, 1H). |

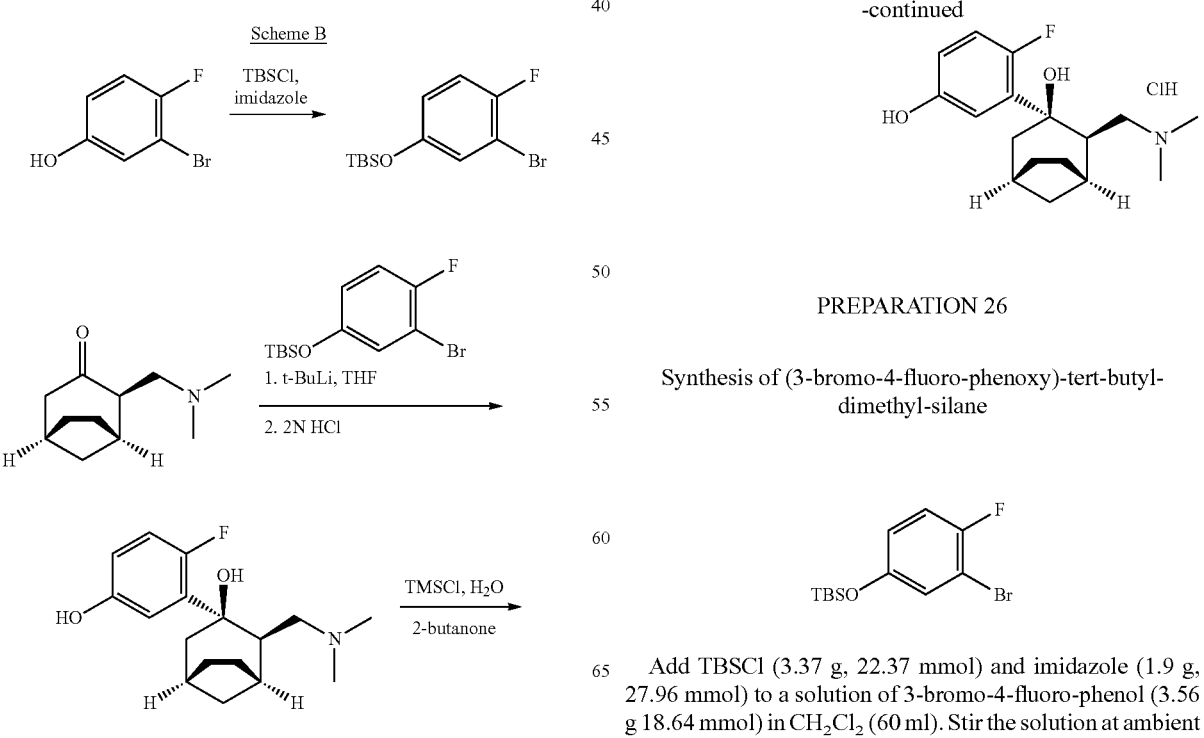

Scheme B

PREPARATION 26

Synthesis of (3-bromo-4-fluoro-phenoxy)-tert-butyl-dimethyl-silane

Add TBSCl (3.37 g, 22.37 mmol) and imidazole (1.9 g, 27.96 mmol) to a solution of 3-bromo-4-fluoro-phenol (3.56 g 18.64 mmol) in CH$_2$Cl$_2$ (60 ml). Stir the solution at ambient temperature for 3 hours. Quench the reaction with water (30 mL). Extract the aqueous layer with $CH_2Cl_2$ (30 mL×3). The combined organic layers are washed with brine, dried over $Na_2SO_4$, concentrated under vacuum. The residue is purified by silica gel chromatography (petroleum ether) to give (3-bromo-4-fluoro-phenoxy)-tert-butyl-dimethyl-silane as colorless oil (5.81 g, 99%), MS (m/z): 303 (M−1).

The following compounds may be prepared essentially by the method of Preparation 26.

| Prep No. | Chemical name | Structure | Physical data |
|---|---|---|---|
| 27 | (3-Bromo-5-fluoro-phenoxy)-tert-butyl-dimethyl-silane | 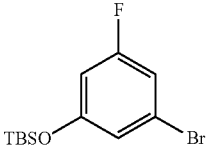 [SMILES: CC(C)(C)[Si](C)(C)Oc1cc(F)cc(Br)c1] | MS (m/z): 303 (M − 1). |
| 28 | (3-Bromo-5-trifluoromethyl-phenoxy)-tert-butyl-dimethyl-silane | 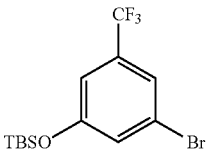 [SMILES: CC(C)(C)[Si](C)(C)Oc1cc(Br)cc(C(F)(F)F)c1] | MS (m/z): 353 (M − 1). |
| 29 | (3-Bromo-4-trifluoro-methoxy-phenoxy)-tert-butyl-dimethyl-silane | 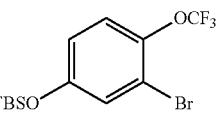 | MS (m/z): 369 (M − 1). |
| 30 | (5-Bromo-2-trifluoromethyl-phenoxy)-tert-butyl-dimethyl-silane | 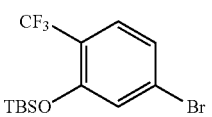 | MS (m/z): 353 (M − 1). |
| 31 | (5-Bromo-2-fluoro-phenoxy)-tert-butyl-dimethyl-silane | 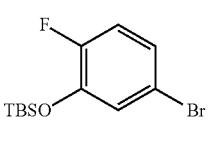 [SMILES: CC(C)(C)[Si](C)(C)Oc1cc(Br)ccc1F] | MS (m/z): 303 (M − 1). |
| 32 | (3-Bromo-2-fluoro-phenoxy)-tert-butyl-dimethyl-silane | 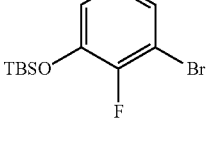 | MS (m/z): 303 (M − 1). |
| 33 | (3-Bromo-5-methyl-phenoxy)-tert-butyl-dimethyl-silane | 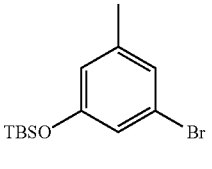 [SMILES: Cc1cc(Br)cc(O[Si](C)(C)C(C)(C)C)c1] | MS (m/z): 299 (M − 1). |
| 34 | (3-Bromo-4-chloro-phenoxy)-tert-butyl-dimethyl-silane | 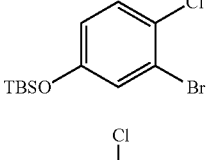 | MS (m/z): 319 (M − 1). |
| 35 | (3-Bromo-5-chloro-phenoxy)-tert-butyl-dimethyl-silane | 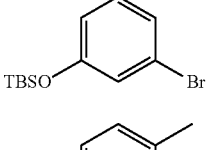 | MS (m/z): 319 (M − 1). |
| 36 | (3-Bromo-4-methyl-phenoxy)-tert-butyl-dimethyl-silane | 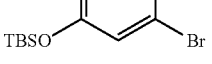 | MS (m/z): 299 (M − 1). |

| Prep No. | Chemical name | Structure | Physical data |
|---|---|---|---|
| 37 | (5-Bromo-2-methyl-phenoxy)-tert-butyl-dimethyl-silane | 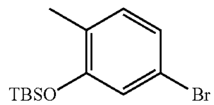 [SMILES: Cc1ccc(Br)cc1O[Si](C)(C)C(C)(C)C] | MS (m/z): 299 (M − 1). |
| 38 | (5-Bromo-2,3-difluoro-phenoxy)-tert-butyl-dimethyl-silane | 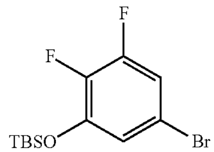 [SMILES: CC(C)(C)[Si](C)(C)Oc1cc(Br)cc(F)c1F] | MS (m/z): 321 (M − 1). |

EXAMPLE 39

Synthesis of 2-dimethylaminomethyl-3-(2-fluoro-5-hydroxy-phenyl)-bicyclo[3.2.1]octan-3-ol

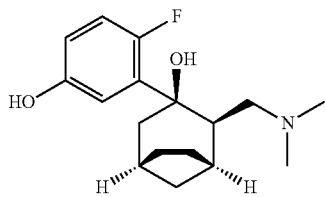

Cool a solution of (3-bromo-4-fluoro-phenoxy)-tert-butyl-dimethyl-silane (5.81 g, 19.03 mmol) in THF (100 mL) to −78° C. under $N_2$. Then add dropwise a solution of t-BuLi (14.6 mL, 19.03 mmol) in hexane via syringe to the reaction solution. After being stirred at −78° C. for 1 hour, add dropwise a solution of 2-dimethylaminomethyl-bicyclo[3.2.1]octan-3-one (2.87 g, 15.86 mmol) in THF (1.5 mL) to the reaction mixture and stir the mixture at −78° C. for additional 1 hour. Quench the reaction with 60 mL of diluted HCl (2N), and stir at ambient temperature for 2 hours. Basify the resultant mixture with $K_2CO_3$ to pH=9, and extract with EtOAc (100 mL×3). The combined organic layers are washed with brine, dried over $Na_2SO_4$, filtered, and concentrated under vacuum. Purify the residue by silica gel chromatography ($CH_2Cl_2$ to $CH_2Cl_2$:MeOH=10:1) to afford 2-dimethylaminomethyl-3-(2-fluoro-5-hydroxy-phenyl)-bicyclo[3.2.1]octan-3-ol as white solid (2.38 g, yield: 51.2%). MS (m/z): 294 (M+1).

The following compounds may be prepared essentially by the method of Example 39.

| Ex. No. | Chemical name | Structure | Physical data |
|---|---|---|---|
| 40 | 2-Dimethylaminomethyl-3-(3-fluoro-5-hydroxy-phenyl)-bicyclo[3.2.1]octan-3-ol | 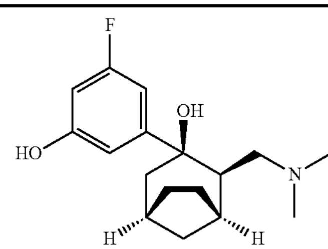 | MS (m/z): 294 (M + 1). |
| 41 | 2-Dimethylaminomethyl-3-(3-hydroxy-5-trifluoromethyl-phenyl)-bicyclo[3.2.1]octan-3-ol | 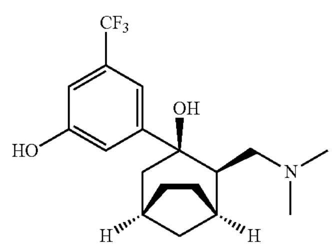 | MS (m/z): 344 (M + 1). |
| 42 | 2-Dimethylaminomethyl-3-(5-hydroxy-2-trifluoromethoxy-phenyl)-bicyclo[3.2.1]octan-3-ol | 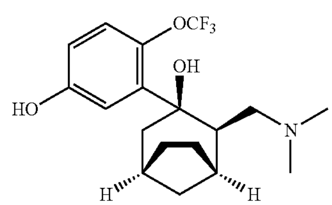 | MS (m/z): 360 (M + 1). |

-continued

| Ex. No. | Chemical name | Structure | Physical data |
|---|---|---|---|
| 43 | 2-Dimethylaminomethyl-3-(3-hydroxy-4-trifluoromethyl-phenyl)-bicyclo[3.2.1]octan-3-ol | 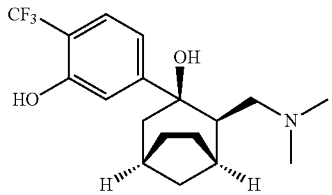 | MS (m/z): 344 (M + 1). |
| 44 | 2-Dimethylaminomethyl-3-(4-fluoro-3-hydroxy-phenyl)-bicyclo[3.2.1]octan-3-ol | 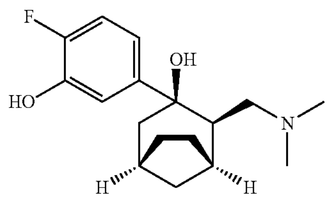 | MS (m/z): 294 (M + 1). |
| 45 | 2-Dimethylaminomethyl-3-(2-fluoro-3-hydroxy-phenyl)-bicyclo[3.2.1]octan-3-ol | 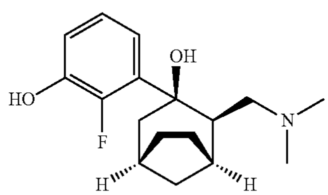 | MS (m/z): 294 (M + 1). |
| 46 | 2-Dimethylaminomethyl-3-(3-hydroxy-5-methyl-phenyl)-bicyclo[3.2.1]octan-3-ol | 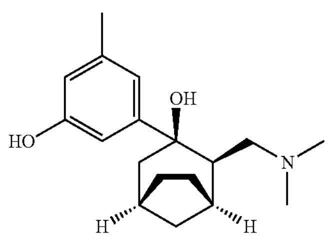 | MS (m/z): 290 (M + 1). |
| 47 | 3-(2-Chloro-5-hydroxy-phenyl)-2-dimethylamino-methyl-bicyclo[3.2.1]octan-3-ol | 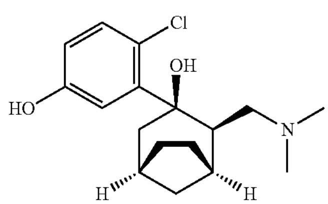 | MS (m/z): 310 (M + 1). |
| 48 | 3-(3-Chloro-5-hydroxy-phenyl)-2-dimethylamino-methyl-bicyclo[3.2.1]octan-3-ol | 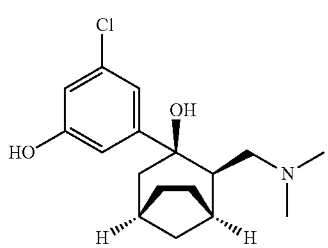 | MS (m/z): 310 (M + 1). |
| 49 | 2-Dimethylaminomethyl-3-(5-hydroxy-2-methyl-phenyl)-bicyclo[3.2.1]octan-3-ol | 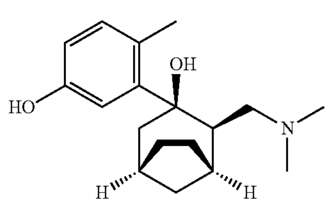 | MS (m/z): 290 (M + 1). |

| Ex. No. | Chemical name | Structure | Physical data |
|---|---|---|---|
| 50 | 2-Dimethylaminomethyl-3-(3-hydroxy-4-methyl-phenyl)-bicyclo[3.2.1]octan-3-ol | 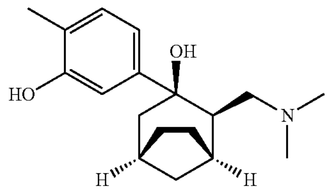 | MS (m/z): 290 (M + 1). |
| 51 | 3-(3,4-Difluoro-5-hydroxy-phenyl)-2-dimethylamino-methyl-bicyclo[3.2.1]octan-3-ol | 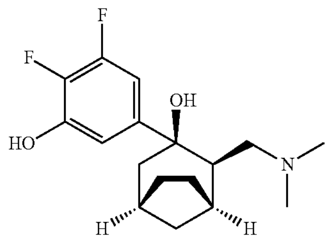 | MS (m/z): 312 (M + 1). |

EXAMPLE 52

Synthesis of 2-dimethylaminomethyl-3-(2-fluoro-5-hydroxy-phenyl)-bicyclo[3.2.1]octan-3-ol

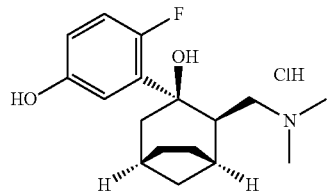

Add $H_2O$ (175.1 mg, 9.73 mmol) and TMSCl (1.057 g, 9.73 mmol) to a solution of 2-dimethylaminomethyl-3-(2-fluoro-5-hydroxy-phenyl)-bicyclo[3.2.1]octan-3-ol (2.38 g, 8.11 mmol) in 2-butanone (60 mL). Stir the reaction mixture at ambient temperature for 3 hours. After removal solvent by evaporation, wash the residue with EtOAc to give 2-dimethylaminomethyl-3-(2-fluoro-5-hydroxy-phenyl)-bicyclo[3.2.1]octan-3-ol hydrochloride as white solid (2.23 g, Yield: 83.5%). $^1$H NMR (400 MHz, $D_2O$) δ 6.89-6.93 (m, 2H), 6.66-6.70 (m, 1H), 3.10-3.14 (m, 1H), 2.59-2.65 (m, 4H), 2.42-2.44 (d, J=8.0, 1H), 2.36-2.41 (d, J=20.0, 3H), 2.30-2.33 (d, J=12.0, 2H), 2.18 (s, 1H), 1.89-1.95 (m, 1H), 1.74-1.78 (m, 1H), 1.51-1.67 (m, 4H), 1.47-1.50 (m, 1H).

The following compounds may be prepared essentially by the method of Example 52.

| Ex. No. | Chemical name | Structure | Physical data |
|---|---|---|---|
| 53 | 2-Dimethylaminomethyl-3-(3-fluoro-5-hydroxy-phenyl)-bicyclo[3.2.1]octan-3-ol hydrochloride | 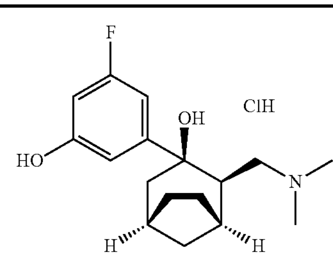 | $^1$H NMR (400 MHz, Methanol-d4) δ 6.74-6.79 (m, 2H), 6.39-6.43 (d, J = 14.4, 1H), 3.26-3.23 (t, J = 14.0 Hz, 1H), 2.74-2.79 (m, 4H), 2.50 (s, 3H), 2.38 (s, 2H), 2.29-2.31 (m, 1H), 2.16-2.27 (m, 2H), 2.03-2.09 (m, 1H), 1.71-1.85 (m, 4H), 1.60-1.67 (m, 1H). |
| 54 | 2-Dimethylaminomethyl-3-(3-hydroxy-5-trifluoromethyl-phenyl)-bicyclo[3.2.1]octan-3-ol hydrochloride | 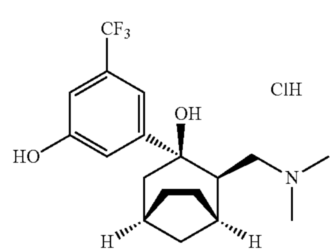 | $^1$H NMR (400 MHz, $D_2O$) δ 7.40-7.42 (d, J = 4.0, 1H), 7.08-7.10 (d, J = 4.0, 1H), 6.93 (s, 1H), 2.41-2.53 (m, 6H), 2.24 (s, 4H), 2.18 (s, 1H), 2.10 (s, 1H), 1.83-1.91 (m, 1H), 1.66-1.72 (m, 2H), 1.39-1.55 (m, 4H). |

-continued

| Ex. No. | Chemical name | Structure | Physical data |
|---|---|---|---|
| 55 | 2-Dimethylaminomethyl-3-(5-hydroxy-2-trifluoromethoxy-phenyl)-bicyclo[3.2.1]octan-3-ol hydrochloride | 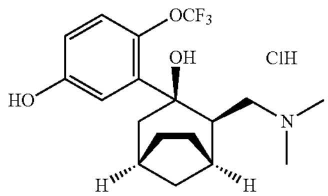 | $^1$H NMR (400 MHz, D$_2$O) δ 7.08-7.11 (d, J$_1$ = 8.8, J$_2$ = 1.2, 1H), 6.96-6.97 (d, J = 3.2, 1H), 6.65-6.68 (d, J = 12.0, 1H), 3.02-3.08 (t, J = 23.2 Hz, 1H), 2.46-2.57 (m, 4H), 2.20-2.41 (m, 6H), 2.10 (s, 1H), 1.83-1.87 (m, 1H), 1.48-1.67 (m, 5H), 1.38-1.41 (m, 1H). |
| 56 | 2-Dimethylaminomethyl-3-(3-hydroxy-4-trifluoromethyl-phenyl)-bicyclo[3.2.1]octan-3-ol hydrochloride | 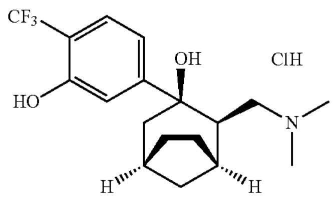 | $^1$H NMR (400 MHz, D$_2$O) δ 7.45-7.47 (d, J = 8.0, 1H), 6.98-7.01 (m, 2H), 3.03-3.09 (t, J = 23.6, 1H), 2.60 (s, 3H), 2.48-2.51 (d, J = 13.2, 1H), 2.30 (s, 3H), 2.23 (s, 1H), 2.12-2.15 (d, J = 8.4, 2H), 2.00-2.04 (m, 1H), 1.87-1.91 (m, 1H), 1.73-1.77 (m, 1H), 1.57-1.67 (m, 4H), 1.44-1.47 (m, 1H). |
| 57 | 2-Dimethylaminomethyl-3-(4-fluoro-3-hydroxy-phenyl)-bicyclo[3.2.1]octan-3-ol hydrochloride | 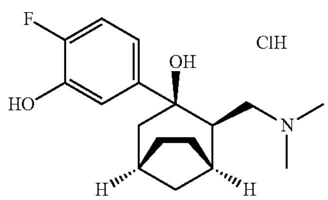 | $^1$H NMR (400 MHz, D$_2$O) δ 7.01-7.06 (m, 2H), 6.90-6.91 (m, 1H), 3.03-3.07 (t, J = 13.6, 1H), 2.57-2.62 (m, 4H), 2.05-2.32 (m, 7H), 1.88-1.92 (m, 1H), 1.72-1.79 (m, 1H), 1.62-1.68 (m, 4H), 1.43-1.51 (m, 1H). |
| 58 | 2-Dimethylaminomethyl-3-(2-fluoro-3-hydroxy-phenyl)-bicyclo[3.2.1]octan-3-ol hydrochloride | 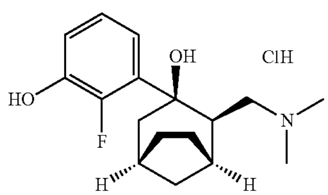 | $^1$H NMR (400 MHz, D$_2$O) δ 7.00-7.96 (m, 2H), 6.88 (s, 1H), 3.10-3.18 (m, 1H), 2.78-2.79 (d, J = 4.0, 4H), 2.27-2.47 (m, 6H), 2.18 (s, 1H), 1.80-1.99 (m, 1H), 1.76 (s, 1H), 1.66-1.68 (d, J = 8.0, 4H), 1.49 (s, 1H). |
| 59 | 2-Dimethylaminomethyl-3-(3-hydroxy-5-methyl-phenyl)-bicyclo[3.2.1]octan-3-ol hydrochloride | 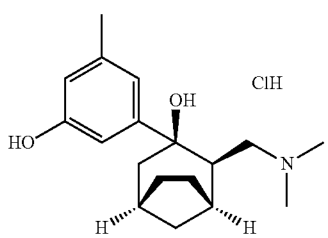 | $^1$H NMR (400 MHz, D$_2$O) δ 6.80 (s, 1H), 6.69 (s, 1H), 6.53 (s, 1H), 3.03-3.06 (t, J = 13.2, 1H), 2.55-2.61 (m, 4H), 2.32 (s, 3H), 2.24 (s, 1H), 2.04-2.18 (m, 6H), 1.77-1.90 (m, 1H), 1.24-1.33 (m, 1H), 1.55-1.69 (m, 4H), 1.41-1.52 (m, 1H). |
| 60 | 3-(2-Chloro-5-hydroxy-phenyl)-2-dimethylaminomethyl-bicyclo[3.2.1]octan-3-ol hydrochloride | 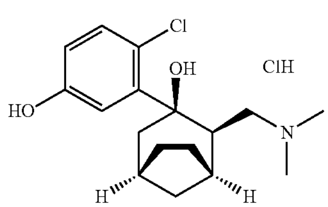 | $^1$H NMR (400 MHz, Methanol-d4) δ 7.34-7.35 (d, J = 2.4, 1H), 7.20-7.21 (d, J = 4.8, 1H), 6.69-6.72 (m, 1H), 3.25-3.31 (m, 1H), 3.02-3.05 (d, J = 9.2, 1H), 2.90-2.94 (m, 1H), 2.73-2.77 (m, 4H), 2.41 (m, 5H), 2.28 (m, 1H), 1.95-2.13 (m, 2H), 1.62-1.78 (m, 4H). |
| 61 | 3-(3-Chloro-5-hydroxy-phenyl)-2-dimethylaminomethyl-bicyclo[3.2.1]octan-3-ol hydrochloride | 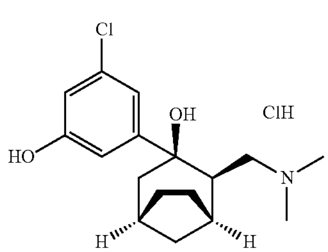 | $^1$H NMR (400 MHz, Methanol-d4) δ 7.01 (t, J = 3.6, 1H), 6.88-6.89 (t, J = 3.6, 1H), 6.69-6.70 (t, J = 3.6, 1H), 3.28-3.31 (t, J = 13.6, 1H), 2.72-2.81 (m, 4H), 2.51 (s, 3H), 2.14-2.40 (m, 5H), 2.04-2.10 (m, 1H), 1.73-1.85 (m, 4H), 1.64-1.67 (m, 1H). |

| Ex. No. | Chemical name | Structure | Physical data |
|---|---|---|---|
| 62 | 2-Dimethylaminomethyl-3-(5-hydroxy-2-methyl-phenyl)-bicyclo[3.2.1]octan-3-ol hydrochloride | 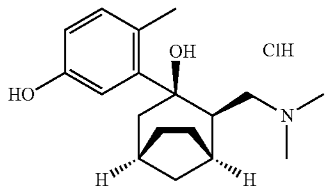 | $^1$H NMR (400 MHz, D$_2$O) δ 7.06 (s, 1H), 7.00-7.02 (d, J = 8.0, 1H), 6.62-6.64 (m, 1H), 3.04-3.11 (m, 1H), 2.60 (s, 4H), 2.37-2.48 (m, 5H), 2.29 (s, 4H), 2.09 (s, 1H), 1.90-1.93 (m, 1H), 1.75-1.78 (m, 2H), 1.59-1.63 (m, 2H), 1.48-1.54 (m, 2H). |
| 63 | 2-Dimethylaminomethyl-3-(3-hydroxy-4-methyl-phenyl)-bicyclo[3.2.1]octan-3-ol hydrochloride | 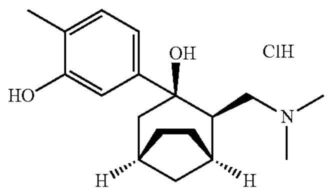 | $^1$H NMR (400 MHz, D$_2$O) δ 7.06-7.08 (d, J = 4.0, 1H), 6.86 (s, 1H), 6.85 (s, 1H), 3.03-3.07 (m, 1H), 2.54-2.59 (m, 4H), 2.22-2.29 (m, 4H), 2.12-2.14 (m, 2H), 2.01-2.07 (m, 4H), 1.91-1.94 (m, 1H), 1.76-1.88 (m, 1H), 1.55-1.66 (m, 4H), 1.43-1.49 (m, 1H). |
| 64 | 3-(3,4-Difluoro-5-hydroxy-phenyl)-2-dimethylamino-methyl-bicyclo[3.2.1]octan-3-ol hydrochloride | 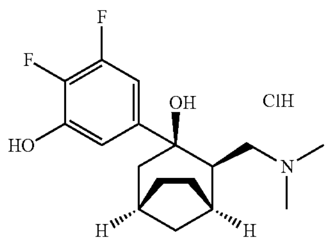 | $^1$H NMR (400 MHz, Methanol-d4) δ 6.75-6.80 (m, 2H), 3.20-3.21 (m, 1H), 2.36-2.72 (m, 7H), 2.26-2.27 (m, 1H), 2.13-2.20 (m, 2H), 2.02-2.08 (m, 2H), 1.91-1.97 (m, 1H), 1.52-1.69 (m, 4H), 1.50-1.51 (m, 1H). |

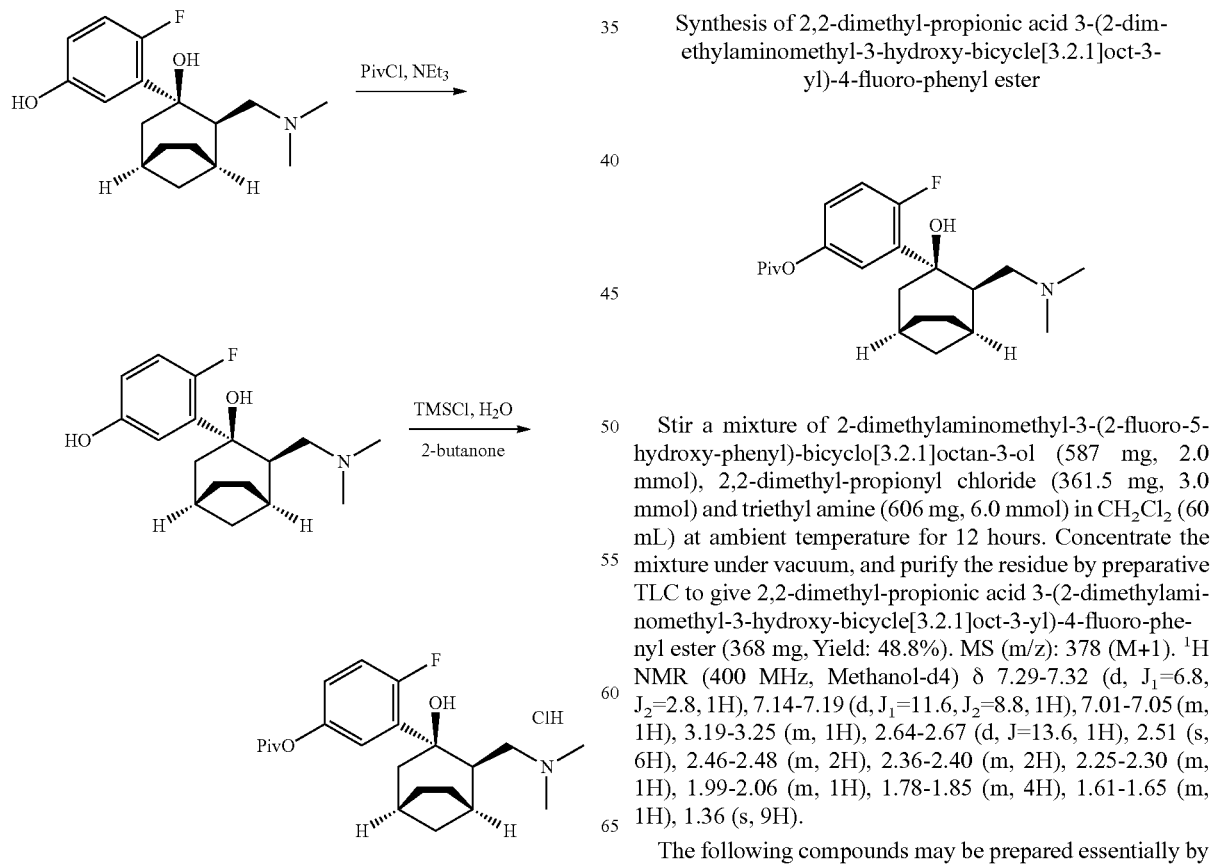

Scheme C

EXAMPLE 65

Synthesis of 2,2-dimethyl-propionic acid 3-(2-dimethylaminomethyl-3-hydroxy-bicycle[3.2.1]oct-3-yl)-4-fluoro-phenyl ester Stir a mixture of 2-dimethylaminomethyl-3-(2-fluoro-5-hydroxy-phenyl)-bicyclo[3.2.1]octan-3-ol (587 mg, 2.0 mmol), 2,2-dimethyl-propionyl chloride (361.5 mg, 3.0 mmol) and triethyl amine (606 mg, 6.0 mmol) in CH$_2$Cl$_2$ (60 mL) at ambient temperature for 12 hours. Concentrate the mixture under vacuum, and purify the residue by preparative TLC to give 2,2-dimethyl-propionic acid 3-(2-dimethylaminomethyl-3-hydroxy-bicycle[3.2.1]oct-3-yl)-4-fluoro-phenyl ester (368 mg, Yield: 48.8%). MS (m/z): 378 (M+1). $^1$H NMR (400 MHz, Methanol-d4) δ 7.29-7.32 (d, J$_1$=6.8, J$_2$=2.8, 1H), 7.14-7.19 (d, J$_1$=11.6, J$_2$=8.8, 1H), 7.01-7.05 (m, 1H), 3.19-3.25 (m, 1H), 2.64-2.67 (d, J=13.6, 1H), 2.51 (s, 6H), 2.46-2.48 (m, 2H), 2.36-2.40 (m, 2H), 2.25-2.30 (m, 1H), 1.99-2.06 (m, 1H), 1.78-1.85 (m, 4H), 1.61-1.65 (m, 1H), 1.36 (s, 9H).

The following compounds may be prepared essentially by the method of Example 65.

| Ex. No. | Chemical name | Structure | Physical data |
|---|---|---|---|
| 66 | Benzoic acid 3-(2-dimethylaminomethyl-3-hydroxy-bicyclo[3.2.1]oct-3-yl)-4-fluoro-phenyl ester | 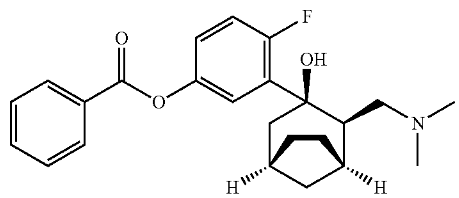 | MS (m/z): 398 (M + 1), $^1$H NMR (400 MHz, Methanol-d4) δ 8.19-8.21 (m, 2H), 7.72-7.76 (t, J = 14.8, 1H), 7.58-7.62 (t, J = 15.6, 2H), 7.47-7.50 (m, 1H), 7.20-7.22 (m, 2H), 3.15-3.18 (m, 1H), 2.62-2.66 (d, J = 13.2, 1H), 2.40-2.55 (m, 10H), 2.28-2.31 (m, 1H), 2.03 (m, 1H), 1.76-1.83 (m, 4H), 1.41-1.50 (m, 1H). |
| 67 | 2,2-Dimethyl-propionic acid 3-(2-dimethyl-aminomethyl-3-hydroxy-bicyclo[3.2.1]oct-3-yl)-phenyl ester | 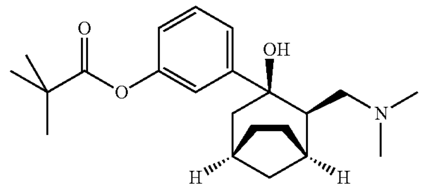 | MS (m/z): 360 (M + 1). |
| 68 | Benzoic acid 3-(2-dimethylaminomethyl-3-hydroxy-bicyclo[3.2.1]oct-3-yl)-phenyl ester | 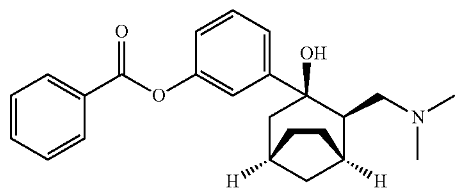 | MS (m/z): 380 (M + 1). |
| 69 | 2,2-Dimethyl-propionic acid 3-(2-dimethylamino-methyl-3-hydroxy-bicyclo[3.2.1]oct-3-yl)-5-fluoro-phenyl ester | 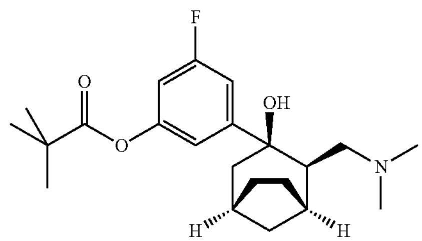 | MS (m/z): 378 (M + 1). |
| 70 | Benzoic acid 3-(2-dimethylaminomethyl-3-hydroxy-bicyclo[3.2.1]oct-3-yl)-5-fluoro-phenyl ester | 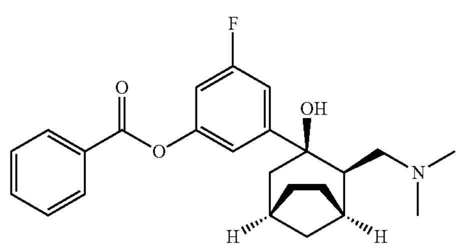 | MS (m/z): 398 (M + 1), $^1$H NMR (400 MHz, Methanol-d4) δ 8.07-8.09 (m, 2H), 7.59-7.61 (t, J = 7.6, 1H), 7.45-7.49 (t, J = 15.6, 2H), 7.10-7.15 (m, 2H), 6.81-6.83 (d, J = 8.8, 1H), 2.71-2.77 (m, 1H), 2.27-2.28 (m, 2H), 2.07-2.13 (m, 7H), 2.04-2.07 (m, 2H), 1.94-2.03 (m, 2H), 1.59-1.74 (m, 4H), 1.45-1.48 (m, 1H). |

EXAMPLE 71

Synthesis of 2,2-dimethyl-propionic acid 3-(2-dimethylaminomethyl-3-hydroxy-bicycle[3.2.1]oct-3-yl)-4-fluoro-phenyl ester hydrochloride

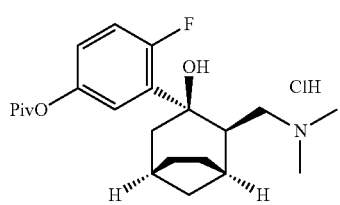

Add $H_2O$ (9 mg, 0.5 mmol) and TMSCl (43 mg, 0.397 mmol) to a solution of 2,2-dimethyl-propionic acid 3-(2-dimethylaminomethyl-3-hydroxy-bicycle[3.2.1]oct-3-yl)-4-fluoro-phenyl ester (150 mg, 0.397 mmol) in 2-butanone (50 mL). Stir the reaction mixture at 0° C. for 2 hours. Evaporate the mixture under vacuum to give 2,2-dimethyl-propionic acid 3-(2-dimethylaminomethyl-3-hydroxy-bicycle[3.2.1]oct-3-yl)-4-fluoro-phenyl ester hydrochloride as white solid (164 mg, Yield: 100%). $^1$H NMR (400 MHz, Methanol-d4) δ 7.30-7.32 (d, $J_1$=6.8, $J_2$=2.8, 1H), 7.15-7.20 (d, $J_1$=11.6, $J_2$=8.8, 1H), 7.03-7.06 (m, 1H), 3.28-3.31 (m, 1H), 2.77-2.81 (m, 4H), 2.37-2.52 (m, 7H), 2.27 (m, 1H), 2.03 (m, 1H), 1.79-1.86 (m, 4H), 1.63-1.65 (m, 1H), 1.38 (s, 9H).

The following compounds may be prepared essentially by the method of Example 71.

| Ex. No. | Chemical name | Structure | Physical data |
|---|---|---|---|
| 72 | Benzoic acid 3-(2-dimethyl-aminomethyl-3-hydroxy-bicyclo[3.2.1]oct-3-yl)-4-fluoro-phenyl ester hydrochloride | 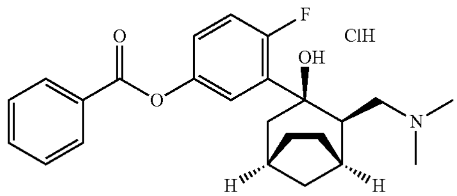 | 1H NMR (400 MHz, Methanol-d4) δ 8.19-8.21 (m, 2H), 7.72-7.76 (t, J = 14.8, 1H), 7.58-7.62 (t, J = 15.6, 2H), 7.49-7.51 (t, J = 8.0, 1H), 7.22-7.24 (m, 2H), 2.42-2.87 (m, 12H), 2.25-2.28 (m, 1H), 2.01-2.03 (m, 1H), 1.79-1.85 (m, 4H), 1.64-1.67 (m, 1H). |
| 73 | 2,2-Dimethyl-propionic acid 3-(2-dimethyl-aminomethyl-3-hydroxy-bicyclo[3.2.1]oct-3-yl)-phenyl ester hydrochloride | 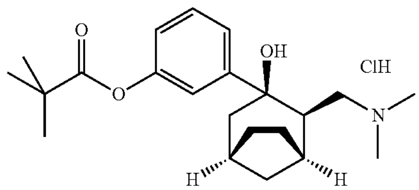 | 1H NMR (400 MHz, Methanol-d4) δ 7.43-7.44 (d, J = 4.4, 2H), 7.24 (s, 1H), 6.94-6.95 (m, 1H), 3.21-3.22 (m, 1H), 2.37-2.81 (m, 9H), 2.21-2.30 (m, 3H), 2.09-2.11 (m, 1H), 1.75-1.88 (m, 4H), 1.63-1.65 (m, 1H), 1.38 (s, 9H). |
| 74 | Benzoic acid 3-(2-dimethyl-aminomethyl-3-hydroxy-bicyclo[3.2.1]oct-3-yl)-phenyl ester hydrochloride | 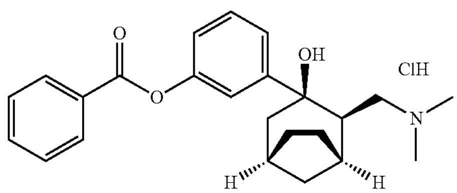 | 1H NMR (400 MHz, Methanol-d4) δ 8.20-8.22 (t, J = 8.4, 2H), 7.72-7.74 (m, 1H), 7.58-7.62 (t, J = 15.2, 2H), 7.50-7.51 (d, J = 5.2, 2H), 7.43 (s, 1H), 7.14 (m, 1H), 3.33 (m, 1H), 2.74-2.86 (m, 4H), 2.43-2.48 (m, 4H), 2.24-2.42 (m, 4H), 2.01-2.10 (m, 1H), 1.76-1.92 (m, 4H), 1.65-1.66 (m, 1H). |
| 75 | 2,2-Dimethyl-propionic acid 3-(2-dimethyl-aminomethyl-3-hydroxy-bicyclo[3.2.1]oct-3-yl)-5-fluoro-phenyl ester hydrochloride | 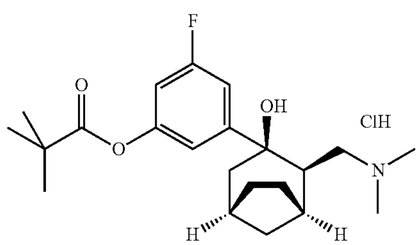 | 1H NMR (400 MHz, Methanol-d4) δ 7.22-7.25 (m, 1H), 7.07 (s, 1H), 6.78-6.80 (m, 1H), 3.25-3.28 (m, 1H), 2.72-2.78 (m, 4H), 2.48 (s, 3H), 2.38-2.39 (d, J = 4.0, 2H), 2.17-2.37 (m, 3H), 2.03 (m, 1H), 1.71-1.87 (m, 4H), 1.64-1.67 (m, 1H), 1.38 (s, 9H). |
| 76 | Benzoic acid 3-(2-dimethyl-aminomethyl-3-hydroxy-bicyclo[3.2.1]oct-3-yl)-5-fluoro-phenyl ester hydrochloride | 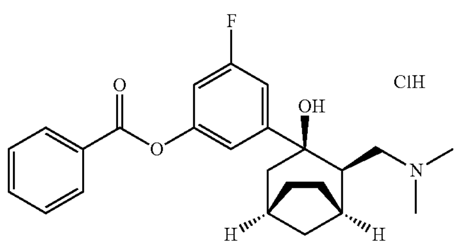 | 1H NMR (400 MHz, Methanol-d4) δ 8.19-8.21 (t, J = 8.4, 2H), 7.72-7.74 (t, J = 8.4, 1H), 7.58-7.62 (t, J = 15.6, 2H), 7.30-7.33 (d, $J_1$ = 10.4, $J_2$ = 1.6, 1H), 7.27 (s, 1H), 6.98-7.00 (d, $J_1$ = 8.8, $J_2$ = 2.0, 1H), 2.55-2.81 (m, 8H), 2.41 (m, 1H), 2.36 (m, 1H), 2.21-2.35 (m, 3H), 2.08-2.10 (m, 1H), 1.74-1.91 (m, 4H), 1.63-1.67 (m, 1H). |

For compounds of the formula Ib, below, Schemes D and E and Examples 77-113 illustrate methods of preparing them.

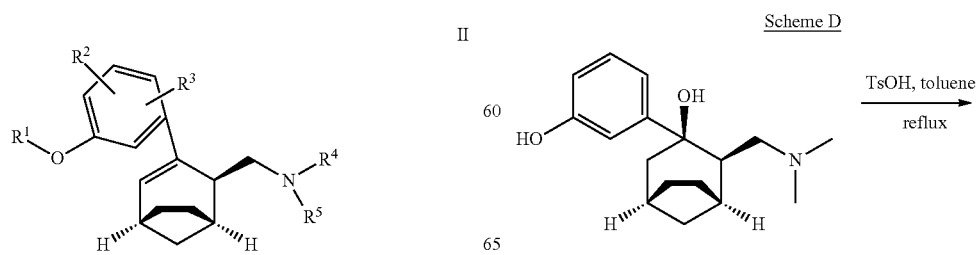

EXAMPLE 77

Synthesis of 3-(4-dimethylaminomethyl-bicyclo[3.2.1]oct-2-en-3-yl)-phenol

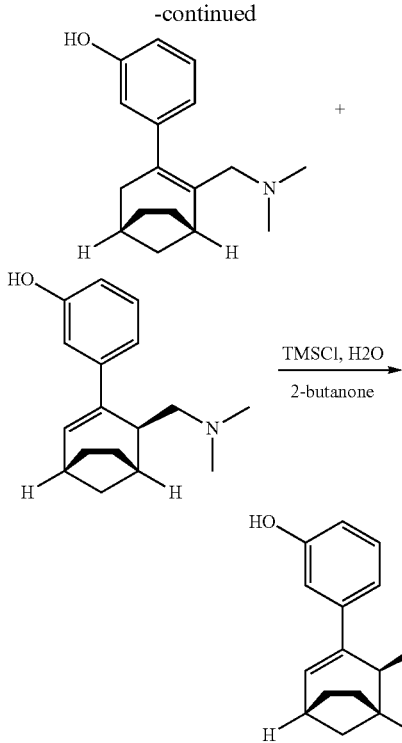

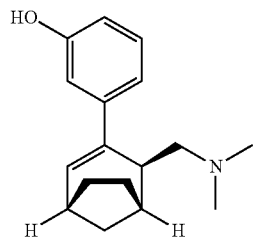

Add TsOH (5.0 g, 29.1 mmol) to a solution of 2-dimethylaminomethyl-3-(3-hydroxy-phenyl)-bicyclo[3.2.1]octan-3-ol (4.8 g, 17.5 mmol) in toluene (150 mL). Heat the reaction mixture to reflux for 2 hours and then quench the reaction by addition of saturated aqueous $K_2CO_3$ (20 mL). Extract the aqueous layer with EtOAc (60 mL×3). The combined organic layers are washed with brine, dried over $Na_2SO_4$ and evaporated under vacuum. Purify the residue by preparative HPLC to yield 3-(4-dimethyl aminomethyl-bicyclo[3.2.1]oct-2-en-3-yl)-phenol as white solid (2.27 g, 50.2%). MS (m/z): 258 (M+1).

The following compounds may be prepared essentially by the method of Example 77.

| Ex. No. | Chemical name | Structure | Physical data |
|---|---|---|---|
| 78 | [3-(3-Methoxy-phenyl)-bicyclo[3.2.1]oct-3-en-2-ylmethyl]-dimethyl-amine | 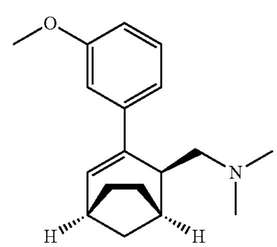 | MS (m/z): 272 (M + 1). |
| 79 | [3-(5-Methoxy-2-trifluoromethoxy-phenyl)-bicyclo[3.2.1]oct-3-en-2-ylmethyl]-dimethyl-amine | 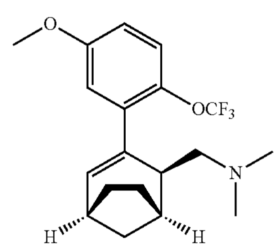 | MS (m/z): 356 (M + 1). |
| 80 | 3-(4-Dimethylaminomethyl-bicyclo[3.2.1]oct-2-en-3-yl)-4-trifluoromethoxy-phenol | 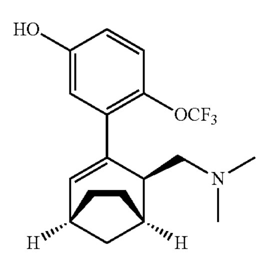 | MS (m/z): 342 (M + 1). |

-continued

| Ex. No. | Chemical name | Structure | Physical data |
|---|---|---|---|
| 81 | [3-(3-Fluoro-5-methoxy-phenyl)-bicyclo[3.2.1]oct-3-en-2-ylmethyl]-dimethyl-amine | 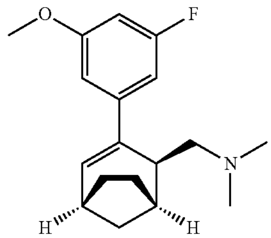 | MS (m/z): 290 (M + 1). |
| 82 | 3-(4-Dimethylaminomethyl-bicyclo[3.2.1]oct-2-en-3-yl)-5-fluoro-phenol | 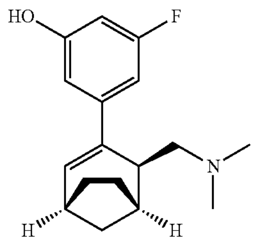 | MS (m/z): 276 (M + 1). |
| 83 | [3-(2-Fluoro-5-methoxy-phenyl)-bicyclo[3.2.1]oct-3-en-2-ylmethyl]-dimethyl-amine | 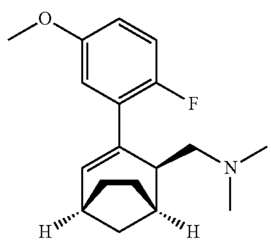 | MS (m/z): 290 (M + 1). |
| 84 | 3-(4-Dimethylaminomethyl-bicyclo[3.2.1]oct-2-en-3-yl)-4-fluoro-phenol | 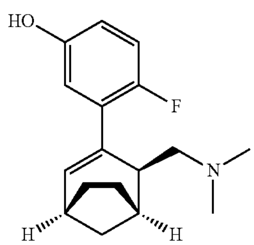 | MS (m/z): 276 (M + 1). |
| 85 | [3-(3-Methoxy-5-methyl-phenyl)-bicyclo[3.2.1]oct-3-en-2-ylmethyl]-dimethyl-amine | 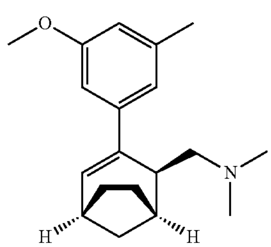 | MS (m/z): 286 (M + 1). |
| 86 | 3-(4-Dimethylaminomethyl-bicyclo[3.2.1]oct-2-en-3-yl)-5-methyl-phenol | 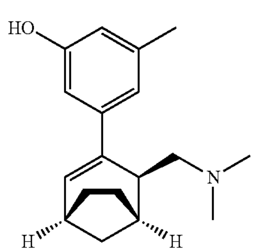 | MS (m/z): 272 (M + 1). |

| Ex. No. | Chemical name | Structure | Physical data |
|---|---|---|---|
| 87 | 3-Chloro-5-(4-dimethyl-aminomethyl-bicyclo[3.2.1]oct-2-en-3-yl)-phenol | 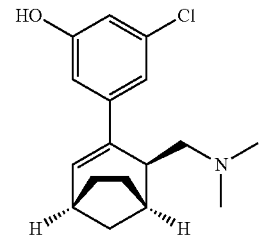 | MS (m/z): 292 (M + 1). |
| 88 | [3-(5-Methoxy-2-methyl-phenyl)-bicyclo[3.2.1]oct-3-en-2-ylmethyl]-dimethyl-amine | 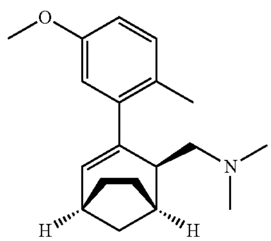 | MS (m/z): 286 (M + 1). |
| 89 | 3-(4-Dimethylaminomethyl-bicyclo[3.2.1]oct-2-en-3-yl)-4-methyl-phenol | 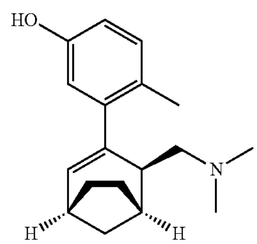 | MS (m/z): 272 (M + 1). |
| 90 | 4-Chloro-3-(4-dimethylamino-methyl-bicyclo[3.2.1]oct-2-en-3-yl)-phenol | 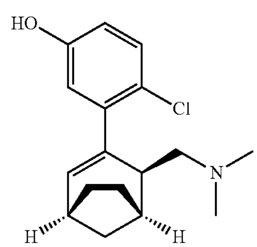 | MS (m/z): 292 (M + 1). |

EXAMPLE 91

Synthesis of 3-(4-dimethylaminomethyl-bicyclo[3.2.1]oct-2-en-3-yl)-phenol hydrochloride

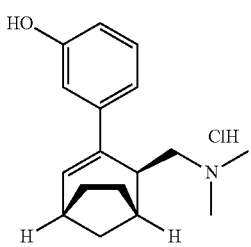

Add H₂O (392 mg, 21.8 mmol) and TMSCl (1.4 g, 12.9 mmol) to a solution of 3-(4-dimethylaminomethyl-bicyclo[3.2.1]oct-2-en-3-yl)-phenol (2.8 g, 10.9 mmol) in 2-butanone (200 mL). Stir the reaction mixture at ambient temperature for 12 hours. Collect the precipitate by filter, and wash with EtOAc (30 mL×2), dry under vacuum to give 3-(4-dimethylaminomethyl-bicyclo[3.2.1]oct-2-en-3-yl)-phenol hydrochloride as white solid (2.41 g, Yield: 75.5%). $^1$H NMR (400 MHz, D₂O) δ 7.20-7.24 (t, J=15.6, 1H), 6.76-6.81 (m, 2H), 6.72 (s, 1H), 6.15 (d, J=6.4, 1H), 3.58-3.61 (d, J=12.8, 1H), 3.08-3.14 (t, J=26.0, 1H), 2.89-2.92 (m, 1H), 2.88 (s, 3H), 2.76 (s, 3H), 2.56 (m, 1H), 2.45 (m, 1H), 1.72-1.83 (m, 6H).

The following compounds may be prepared essentially by the method of Example 91.

| Ex. No. | Chemical name | Structure | Physical data |
|---|---|---|---|
| 92 | [3-(3-Methoxy-phenyl)-bicyclo[3.2.1]oct-3-en-2-ylmethyl]-dimethyl-amine hydrochloride | 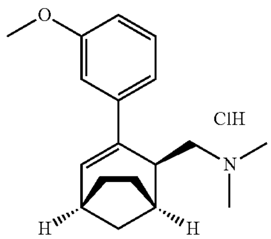 | $^1$H NMR (400 MHz, D$_2$O) δ 7.24-7.28 (t, J = 16.0, 1H), 6.82-6.87 (t, J = 20.4, 2H), 6.78 (s, 1H), 6.12-6.14 (d, J = 7.2, 1H), 3.77 (s, 3H), 3.56-3.59 (m, 1H), 3.04-3.11 (m, 1H), 2.77-2.86 (m, 6H), 2.54 (m, 1H), 2.42 (m, 1H), 2.15 (s, 2H), 1.77-1.80 (m, 1H), 1.65-1.75 (m, 4H). |
| 93 | [3-(5-Methoxy-2-trifluoromethoxy-phenyl)-bicyclo[3.2.1]oct-3-en-2-ylmethyl]-dimethyl-amine hydrochloride | 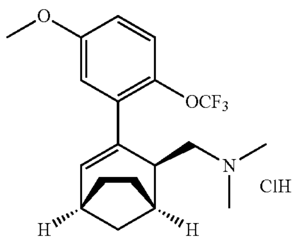 | $^1$H NMR (400 MHz, D$_2$O) δ 7.15-7.18 (d, J = 9.6, 1H), 6.81-6.84 (m, 1H), 6.69-6.70 (d, J = 5.6, 1H), 6.03-6.01 (d, J = 4.0, 1H), 3.68 (s, 3H), 3.46-3.47 (d, J = 4.0, 1H), 3.01-3.06 (m, 1H), 2.64-2.70 (d, J = 9.6, 6H), 2.32-2.46 (m, 4H), 1.16-1.80 (m, 6H). |
| 94 | 3-(4-Dimethylamino-methyl-bicyclo[3.2.1]oct-2-en-3-yl)-4-trifluoro-methoxy-phenol hydrochloride | 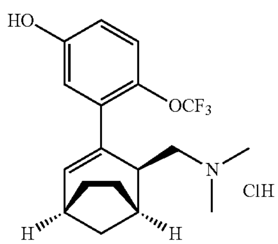 | $^1$H NMR (400 MHz, D$_2$O) δ 7.02-7.04 (d, J = 8.8, 1H), 6.68- 6.71 (d, J = 11.6, 1H), 6.56 (d, J = 3.2, 1H), 5.92-5.93 (d, 7 = 6.8, 1H), 3.32-3.37 (d, J = 18.8, 1H), 2.58-2.59 (m, 2H), 2.37-2.54 (m, 1H), 2.18 (s, 6H), 1.71-1.88 (m, 7H). |
| 95 | [3-(3-Fluoro-5-methoxy-phenyl)-bicyclo[3.2.1]oct-3-en-2-ylmethyl]-dimethyl-amine hydrochloride | 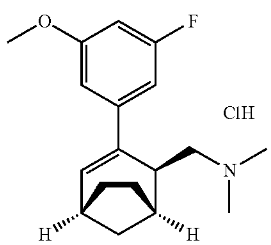 | $^1$H NMR (400 MHz, D$_2$O) δ 6.35-6.38 (m, 3H), 6.01- 6.12 (d, J = 6.4, 1H), 3.69-3.70 (d, J = 3.2, 3H), 3.48-3.50 (m, 1H), 3.02-3.09 (m, 1H), 2.68-2.82 (m, 7H), 2.49 (s, 1H), 2.36 (s, 1H), 1.63-1.74 (m, 6H). |
| 96 | 3-(4-Dimethylamino-methyl-bicyclo[3.2.1]oct-2-en-3-yl)-5-fluoro-phenol hydrochloride | 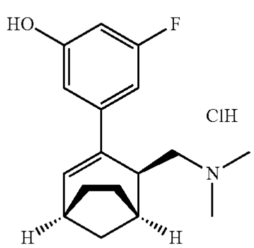 | $^1$H NMR (400 MHz, Methanol-d4) δ 6.44-6.49 (m, 2H), 6.41-6.42 (d, J = 2.0, 1H), 6.18-6.19 (d, J = 6.8, 1H), 3.60-3.63 (d, J = 14.0, 1H), 3.16-3.22 (t, J = 25.6, 1H), 2.99-3.00 (d, J = 3.6, 1H), 2.90-2.93 (d, J = 14.8, 6H), 2.64 (s, 1H), 2.57 (s, 1H), 1.92-1.95 (d, J = 10.8, 1H), 1.85 (m, 5H). |
| 97 | [3-(2-Fluoro-5-methoxy-phenyl)-bicyclo[3.2.1]oct-3-en-2-ylmethyl]-dimethyl-amine hydrochloride | 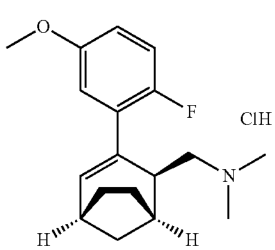 | $^1$H NMR (400 MHz, D$_2$O) δ 6.91-6.96 (m, 1H), 6.77-6.79 (m, 1H), 6.66-6.68 (m, 1H), 6.07-6.08 (d, J = 4.0, 1H), 3.66-3.67 (d, J = 4.0, 3H), 3.47 (s, 1H), 3.03 (m, 1H), 2.60-2.69 (m, 6H), 2.48 (s, 1H), 2.33 (s, 1H), 1.62-1.78 (m, 7H). |

| Ex. No. | Chemical name | Structure | Physical data |
|---|---|---|---|
| 98 | 3-(4-Dimethylamino-methyl-bicyclo[3.2.1]oct-2-en-3-yl)-4-fluoro-phenol hydrochloride | 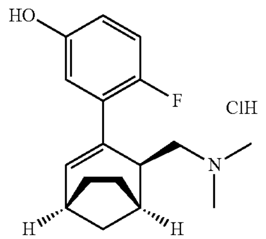 | $^1$H NMR (400 MHz, D$_2$O) δ 6.83-6.88 (m, 1H), 6.63-6.67 (m, 1H), 6.54-6.57 (m, 1H), 6.03-6.05 (d, J = 8.0, 1H), 3.44-3.48 (d, J = 16.0, 1H), 3.01-3.09 (m, 1H), 2.61-2.69 (m, 7H), 2.48 (s, 1H), 2.32 (s, 1H), 1.76-1.79 (d, J = 12.0, 1H), 1.70-1.71 (d, J = 4.0, 1H), 1.61-1.65 (m, 4H). |
| 99 | [3-(3-Methoxy-5-methyl-phenyl)-bicyclo[3.2.1]oct-3-en-2-ylmethyl]-dimethyl-amine hydrochloride | 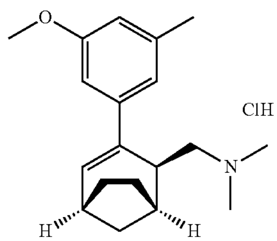 | $^1$H NMR (400 MHz, Methanol-d4) δ 6.67-6.69 (m, 2H), 6.57 (s, 1H), 6.13-6.14 (d, J = 6.8, 1H), 3.80 (s, 3H), 3.64-3.67 (d, J = 12.4, 1H), 3.14-3.26 (m, 1H), 2.86-2.95 (m, 7H), 2.57-2.63 (m, 2H), 2.33 (s, 3H), 1.94-1.97 (m, 1H), 1.79-1.92 (m, 5H). |
| 100 | 3-(4-Dimethylamino-methyl-bicyclo[3.2.1]oct-2-en-3-yl)-5-methyl-phenol hydrochloride | 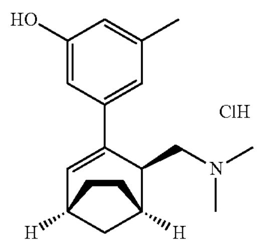 | $^1$H NMR (400 MHz, D$_2$O) δ 6.63-6.53 (d, J = 1.2, 2H), 6.44 (s, 1H), 6.11-6.13 (d, J = 6.4, 1H), 3.59-3.63 (m, 1H), 3.13-3.19 (m, 1H), 2.99-3.00 (m, 1H), 2.89-2.97 (m, 6H), 2.55-2.62 (m, 2H), 2.18 (s, 3H), 1.80-1.95 (m, 6H). |
| 101 | 3-Chloro-5-(4-dimethyl-aminomethyl-bicyclo[3.2.1]oct-2-en-3-yl)-phenol hydrochloride | 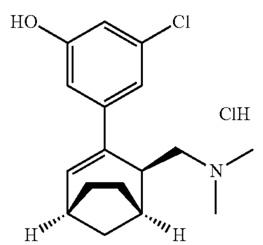 | $^1$H NMR (400 MHz, Methanol-d4) δ 6.71-6.73 (m, 2H), 6.58-6.59 (t, J = 3.6, 1H), 6.16-6.18 (d, J = 6.4, 1H), 3.62-3.68 (m, 1H), 3.16-3.23 (t, J = 26.0, 1H), 2.90-2.96 (m, 7H), 2.56-2.64 (m, 2H), 1.83-1.95 (m, 6H). |
| 102 | [3-(5-Methoxy-2-methyl-phenyl)-bicyclo[3.2.1]oct-3-en-2-ylmethyl]-dimethyl-amine hydrochloride | 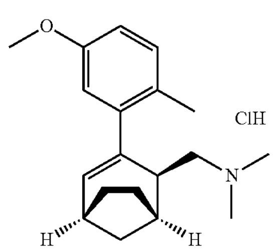 | $^1$H NMR (400 MHz, D$_2$O) δ 7.10 (d, J = 6.4, 1H), 6.75 (d, J$_1$ = 2.4, J$_2$ = 6.4, 1H), 6.58 (m, 1H), 5.78 (s, 1H), 3.71 (s, 3H), 3.35 (d, J = 12.0, 1H), 3.12 (t, J = 12.4, 1H), 2.62 (s, 6H), 2.48 (s, 2H), 2.35 (m, 1H), 2.06 (s, 3H), 1.84 (m, 1H), 1.73 (m, 1H), 1.65 (m, 4H). |
| 103 | 3-(4-Dimethylamino-methyl-bicyclo[3.2.1]oct-2-en-3-yl)-4-methyl-phenol hydrochloride | 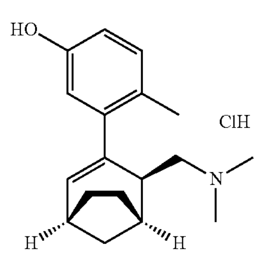 | $^1$H NMR (400 MHz, D$_2$O) δ 7.21-7.23 (d, J = 4.0, 1H), 6.82-6.84 (d, J = 4.0, 1H), 6.69 (s, 1H), 6.96-6.97 (d, J = 4.0, 1H), 3.50-3.52 (m, 1H), 3.25-3.27 (m, 1H), 2.85 (s, 6H), 2.66-2.71 (m, 2H), 2.54 (s, 1H), 2.23 (s, 3H), 1.87-2.05 (m, 6H). |

| Ex. No. | Chemical name | Structure | Physical data |
|---|---|---|---|
| 104 | 4-Chloro-3-(4-dimethyl-aminomethyl-bicyclo[3.2.1]oct-2-en-3-yl)-phenol hydrochloride | 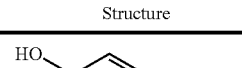 | $^1$H NMR (400 MHz, Methanol-d4) δ 7.18-7.20 (d, J = 8.8, 1H), 6.70-6.73 (d, J$_1$ = 8.8, J$_2$ = 3.2, 1H), 6.60 (s, 1H), 5.97-5.98 (d, J = 6.0, 1H), 3.71-3.76 (m, 1H), 3.32-3.34 (t, J = 6.4, 1H), 2.87 (s, 6H), 2.63-2.66 (s, 3H), 2.03-2.05 (d, J = 10.8, 1H), 1.83-1.94 (m, 5H). |

EXAMPLE 105

Synthesis of 2,2-dimethyl-propionic acid 3-(4-dimethylaminomethyl-bicyclo[3.2.1]oct-2-en-3-yl)-phenyl ester

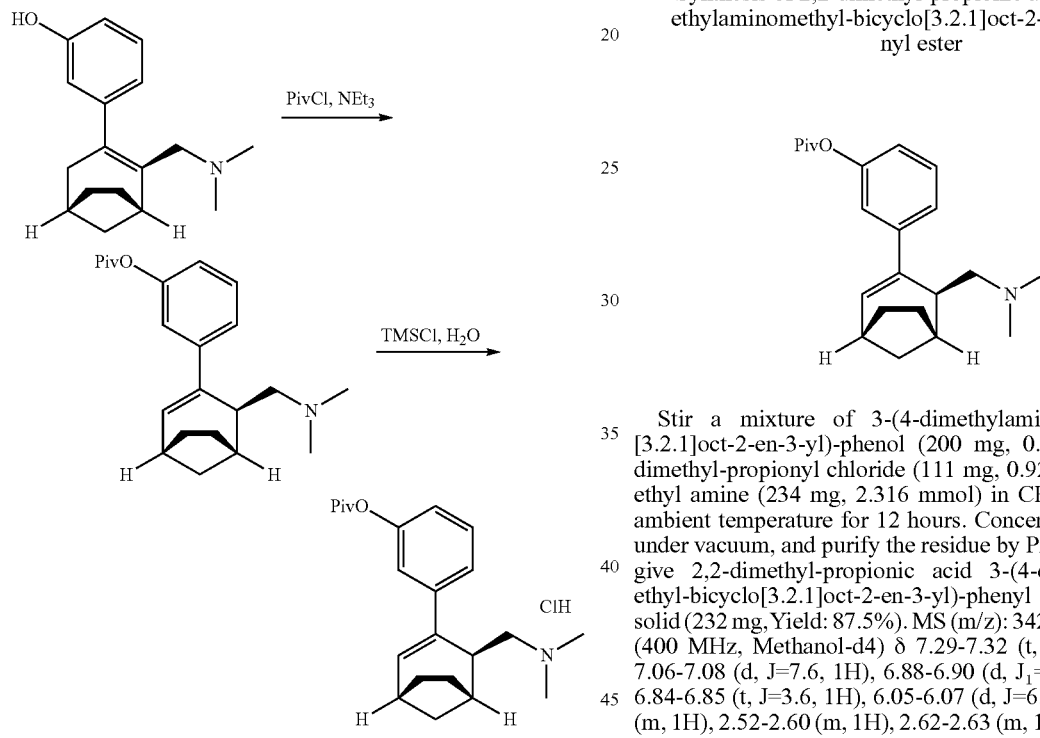

Stir a mixture of 3-(4-dimethylaminomethyl-bicyclo[3.2.1]oct-2-en-3-yl)-phenol (200 mg, 0.778 mmol), 2,2-dimethyl-propionyl chloride (111 mg, 0.927 mmol) and tri-ethyl amine (234 mg, 2.316 mmol) in CH$_2$Cl$_2$ (40 mL) at ambient temperature for 12 hours. Concentrate the mixture under vacuum, and purify the residue by Preparative TLC to give 2,2-dimethyl-propionic acid 3-(4-dimethylaminomethyl-bicyclo[3.2.1]oct-2-en-3-yl)-phenyl ester as white solid (232 mg, Yield: 87.5%). MS (m/z): 342 (M+1). $^1$H NMR (400 MHz, Methanol-d4) δ 7.29-7.32 (t, J=15.6 Hz, 1H), 7.06-7.08 (d, J=7.6, 1H), 6.88-6.90 (d, J$_1$=8.0, J$_2$=1.6, 1H), 6.84-6.85 (t, J=3.6, 1H), 6.05-6.07 (d, J=6.8, 1H), 3.22-3.32 (m, 1H), 2.52-2.60 (m, 1H), 2.62-2.63 (m, 1H), 2.37-2.41 (m, 1H), 2.17 (s, 6H), 2.07-2.14 (m, 1H), 1.71-1.85 (m, 6H), 1.37 (s, 9H).

The following compounds may be prepared essentially by the method of Example 105.

| Ex. No. | Chemical name | Structure | Physical data |
|---|---|---|---|
| 106 | Benzoic acid 3-(4-dimethylaminomethyl-bicyclo[3.2.1]oct-2-en-3-yl)-phenyl ester | 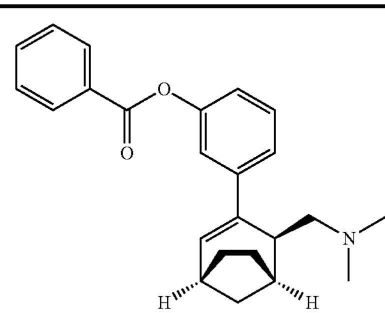 | MS (m/z): 362 (M + 1), $^1$H NMR (400 MHz, Methanol-d4) δ 8.19-8.21 (d, J = 8.0, 2H), 7.70-7.73 (t, J = 15.2 Hz, 1H), 7.57-7.61 (t, J = 19.6, 2H), 7.36-7.40 (t, J = 15.6, 1H), 7.14-7.16 (d, J = 8.0, 1H), 7.07-7.09 (m, 2H), 6.11-6.13 (d, J = 6.8, 1H), 3.31-3.33 (m, 2H), 2.59-2.64 (d, J = 20.4, 2H), 2.42-2.45 (t, J = 13.2, 1H), 2.18-2.20 (m, 6H), 1.75-1.88 (m, 6H). |

-continued

| Ex. No. | Chemical name | Structure | Physical data |
|---|---|---|---|
| 107 | 2,2-Dimethyl-propionic-acid 3-(4-dimethyl-aminomethyl-bicyclo[3.2.1]oct-2-en-3-yl)-5-fluoro-phenyl ester | 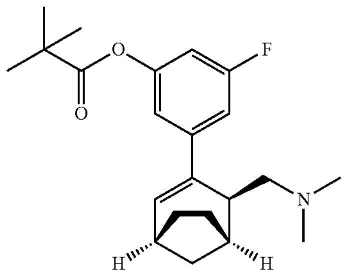 | MS (m/z): 360 (M + 1), $^1$H NMR (400 MHz, Methanol-d4) δ 6.94-6.97 (m, 1H), 6.80-6.81 (m, 2H), 6.25-6.28 (d, J = 9.2, 1H), 3.68-3.71 (d, J = 12.4, 1H), 3.18-3.25 (t, J = 26.0, 1H), 2.90-2.93 (m, 7H), 2.62-2.66 (m, 2H), 1.85-1.96 (m, 6H), 1.37 (s, 9H). |
| 108 | Isobutyric acid 3-(4-dimethylamino-methyl-bicyclo[3.2.1]oct-2-en-3-yl)-5-fluoro-phenyl ester | 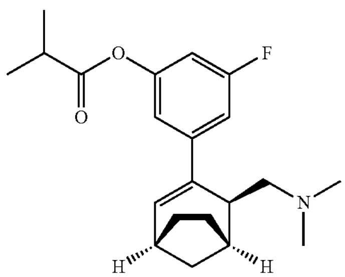 | MS (m/z): 346 (M + 1). $^1$H NMR (400 MHz, Methanol-d4) δ 6.86-6.89 (m, 1H), 6.76-6.79 (m, 2H), 6.14-6.15 (d, J = 6.8, 1H), 3.36-3.39 (m, 1H), 2.82-2.85 (m, 1H), 2.54-2.63 (m, 3H), 2.37 (s, 6H), 2.25-2.29 (m, 1H), 1.74-1.87 (m, 6H), 1.31-1.32 (d, J = 6.8, 6H). |
| 109 | 2,2-Dimethyl-propioni-acid 3-(4-dimethyl-aminomethyl-bicyclo[3.2.1]oct-2-en-3-yl)-4-fluoro-phenyl ester | 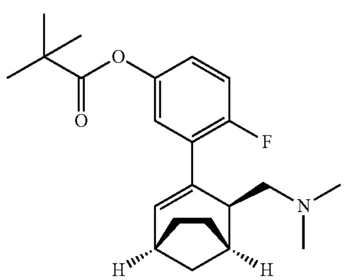 | MS (m/z): 360 (M + 1), $^1$H NMR (Methanol-d4, 400 MHz) δ 7.10 (t, J = 9.6, 1H), 6.97 (m, 1H), 6.88 (m, 1H), 6.12 (d, J = 9.6, 1H), 3.48 (m, 1H), 2.85 (t, J = 12.4, 1H), 2.61 (s, 2H), 2.52 (s, 6H), 2.33 (m, 1H), 1.94 (m, 1H), 1.83 (m, 5H), 1.38 (s, 9H). |
| 110 | Isobutyric acid 3-(4-dimethylamino-methyl-bicyclo[3.2.1]oct-2-en-3-yl)-4-fluoro-phenyl ester | 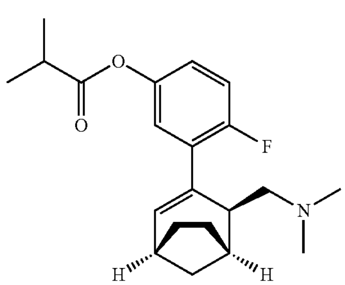 | MS (m/z): 346 (M + 1). $^1$H NMR (Methanol-d4, 400 MHz) δ 7.10 (t, J = 9.6, 1H), 7.01 (m, 1H), 6.90 (m, 1H), 6.11 (d, J = 6.4, 1H), 3.50 (m, 1H), 2.85 (m, 2H), 2.62 (s, 2H), 2.55 (s, 6H), 2.48 (m, 1H), 1.95 (m, 1H), 1.76 (m, 5H), 1.31 (d, J = 6.8, 6H). |

EXAMPLE 111

Synthesis of 2,2-dimethyl-propionic acid 3-(4-dimethylaminomethyl-bicyclo[3.2.1]oct-2-en-3-yl)-phenyl ester hydrochloride

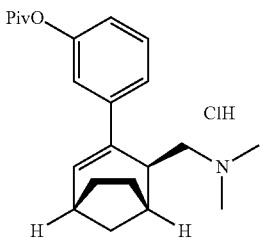

Add H$_2$O (18 mg, 1 mmol) and TMSCl (75 mg, 0.69 mmol) to a solution of 2,2-dimethyl-propionic acid 3-(4-dimethylaminomethyl-bicyclo[3.2.1]oct-2-en-3-yl)-phenyl ester (197 mg, 0.58 mmol) in 2-butanone (70 mL). Stir the reaction mixture at ambient temperature for 2 hours. Evaporate the mixture under vacuum to afford 2,2-dimethyl-propionic acid 3-(4-dimethylaminomethyl-bicyclo[3.2.1]oct-2-en-3-yl)-phenyl ester hydrochloride as white solid (219 mg, Yield: 100%). $^1$H NMR (400 MHz, Methanol-d4) δ 7.38-7.42 (t, J=16.4, 1H), 7.13-7.15 (d, J$_1$=7.2, J$_2$=0.8, 1H), 6.96-6.98 (m, 2H), 6.21-6.23 (d, J=6.8, 1H), 3.68-3.71 (d, J=12.0, 1H), 3.16-3.23 (t, J=25.6, 1H), 2.99-3.00 (m, 1H), 2.88-2.92 (d, J=14.8, 6H), 2.65 (m, 1H), 2.60 (m, 1H), 1.95-1.98 (m, 1H), 1.82-1.86 (m, 5H), 1.37 (s, 9H).

The following compounds may be prepared essentially by the method of Example 111.

For compounds of the formula Ic, below, Schemes F and G and Preparations and/or Examples 114-140 illustrate methods of preparing them.

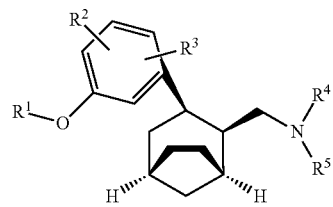

Ic

Scheme F

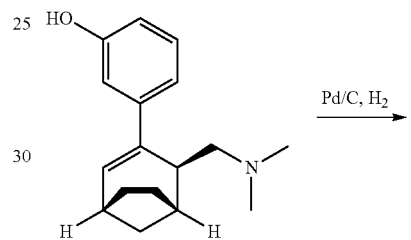

| Ex. No. | Chemical name | Structure | Physical data |
|---|---|---|---|
| 112 | Benzoic acid 3-(4-dimethylaminomethyl-bicyclo[3.2.1]oct-2-en-3-yl)-phenyl ester hydrochloride | 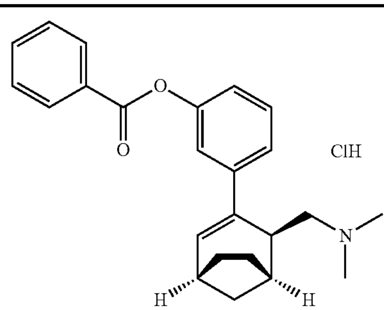 | $^1$H NMR (400 MHz, Methanol-d4) δ 8.19-8.21 (t, J = 8.0, 2H), 7.71-7.74 (t, J = 14.8, 1H), 7.57-7.61 (t, J = 15.6, 2H), 7.43-7.72 (t, J = 15.6, 1H), 7.13-7.22 (m, 3H), 6.25-6.27 (d, J = 6.8, 1H), 3.71-3.74 (d, J = 12.0, 1H), 3.19-3.26 (t, J = 25.6, 1H), 3.02-3.06 (m, 1H), 2.90-2.94 (d, J = 14.8, 6H), 2.65 (s, 2H), 1.95-1.98 (m, 1H), 1.83-1.87 (m, 5H). |
| 113 | 2,2-Dimethyl-propionic acid 3-(4-dimethylaminomethyl-bicyclo[3.2.1]oct-2-en-3-yl)-5-fluoro-phenyl ester hydrochloride | 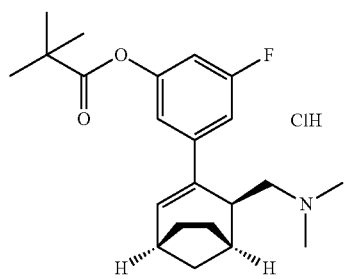 | $^1$H NMR (400 MHz, Methanol-d4) δ 6.94-6.96 (d, J$_1$ = 3.6, J$_2$ = 2.0, 1H), 6.81-6.83 (m, 2H), 6.25-6.27 (d, J = 6.8, 1H), 3.65-3.68 (d, J = 10.8, 1H), 3.15-3.21 (t, J = 26.0, 1H), 2.88-2.93 (m, 7H), 2.66 (m, 1H), 2.58 (m, 1H), 1.82-1.96 (m, 6H), 1.37 (s, 9H). |

-continued

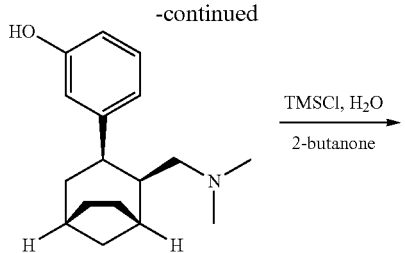

→ TMSCl, H₂O / 2-butanone

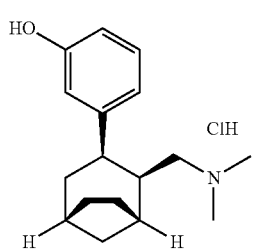
·ClH

EXAMPLE 114

Synthesis of 3-(2-dimethylaminomethyl-bicyclo[3.2.1]oct-3-yl)-phenol

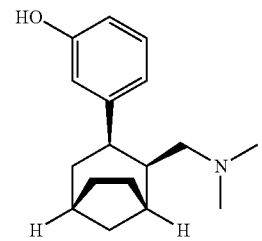

Add Pd/C (80 mg) to a solution of 3-(4-dimethylaminomethyl-bicyclo[3.2.1]oct-2-en-3-yl)-phenol (250 mg, 0.97 mmol) in MeOH (40 mL). Then stir the mixture at 25° C. for 12 hours under 45 PSI of H₂. After filtration, Concentrate the solution under vacuum to afford 3-(2-dimethylaminomethyl-bicyclo[3.2.1]oct-3-yl)-phenol as white solid (252 mg, Yield: 100%). MS (m/z): 260 (M+1).

The following compounds may be prepared essentially by the method of Example 114.

| Ex. No. | Chemical name | Structure | Physical data |
|---|---|---|---|
| 115 | [3-(3-methoxy-phenyl)-bicyclo[3.2.1]oct-2-ylmethyl]-dimethyl-amine | 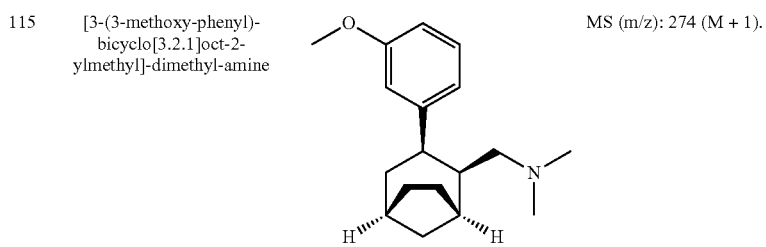 | MS (m/z): 274 (M + 1). |
| 116 | 3-(2-dimethylaminomethyl-bicyclo[3.2.1]oct-3-yl)-5-fluoro-phenol | 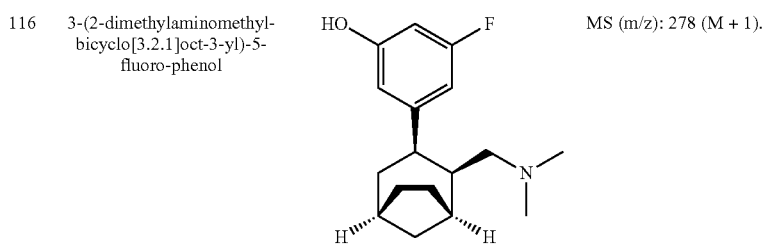 | MS (m/z): 278 (M + 1). |
| 117 | [3-(3-fluoro-5-methoxy-phenyl)-bicyclo[3.2.1]oct-2-ylmethyl]-dimethyl-amine | 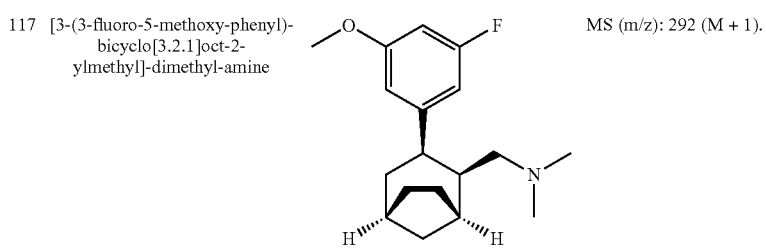 | MS (m/z): 292 (M + 1). |

-continued

| Ex. No. | Chemical name | Structure | Physical data |
|---|---|---|---|
| 118 | 3-(2-dimethylaminomethyl-bicyclo[3.2.1]oct-3-yl)-4-fluoro-phenol | 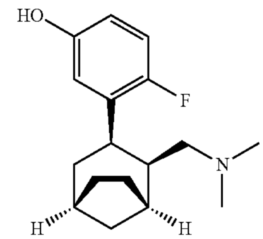 | MS (m/z): 278 (M + 1). |
| 119 | [3-(2-fluoro-5-methoxy-phenyl)-bicyclo[3.2.1]oct-2-ylmethyl]-dimethyl-amine | 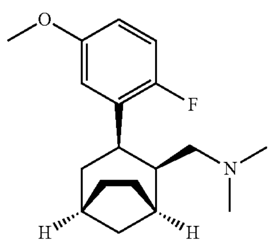 | MS (m/z): 292 (M + 1). |
| 120 | 3-(2-dimethylaminomethyl-bicyclo[3.2.1]oct-3-yl)-5-methyl-phenol | 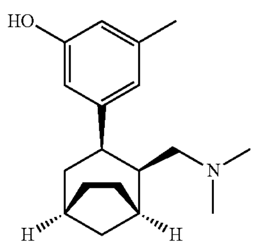 | MS (m/z): 274 (M + 1). |
| 121 | [3-(3-methoxy-5-methyl-phenyl)-bicyclo[3.2.1]oct-2-ylmethyl]-dimethyl-amine | 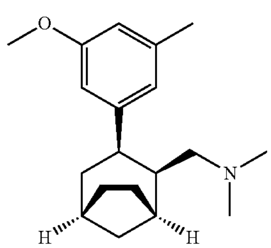 | MS (m/z): 288 (M + 1). |

EXAMPLE 122

Synthesis of 3-(2-dimethylaminomethyl-bicyclo[3.2.1]oct-3-yl)-phenol hydrochloride

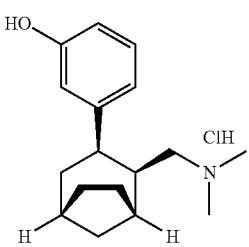

Add $H_2O$ (70 mg, 3.89 mmol) and TMSCl (126 mg, 1.17 mmol) to a solution of 3-(2-dimethylaminomethyl-bicyclo[3.2.1]oct-3-yl)-phenol (252 mg, 0.97 mmol) in 2-butanone (30 ml). Then stir the reaction mixture at ambient temperature for 12 hours. Evaporate the mixture under vacuum to give 3-(2-dimethylaminomethyl-bicyclo[3.2.1]oct-3-yl)-phenol hydrochloride as white solid (286 mg, Yield: 99.8%). $^1$H NMR (400 MHz, $D_2O$) δ 7.04-7.07 (t, J=10.4, 1H), 6.58-6.72 (m, 3H), 2.80-2.91 (m, 1H), 2.52-2.54 (m, 3H), 2.44-2.48 (m, 3H), 2.33-2.41 (m, 1H), 2.20-2.29 (m, 1H), 2.11 (s, 1H), 1.99 (s, 2H), 1.36-1.47 (m, 8H).

The following compounds may be prepared essentially by the method of Example 122.

| Ex. No. | Chemical name | Structure | Physical data |
|---|---|---|---|
| 123 | [3-(3-methoxy-phenyl)-bicyclo[3.2.1]oct-2-ylmethyl]-dimethyl-amine hydrochloride | 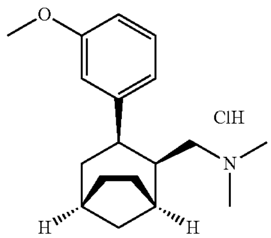 | ¹H NMR (400 MHz, D₂O) δ 7.23-7.27 (t, J = 15.6, 1H), 6.80-6.90 (m, 3H), 3.73 (s, 3H), 2.95-3.01 (m, 1H), 2.54-2.62 (m, 6H), 2.38-2.42 (m, 2H), 2.22 (s, 1H), 2.12-2.14 (m, 2H), 1.48-1.67 (m, 8H). |
| 124 | 3-(2-dimethylamino-methyl-bicyclo[3.2.1]oct-3-yl)-5-fluoro-phenol hydrochloride | 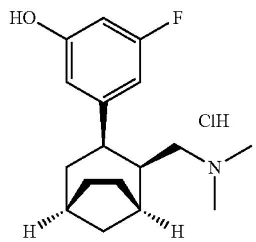 | ¹H NMR (400 MHz, D₂O) δ 6.55-6.49 (m, 2H), 6.41-6.38 (d, J = 12.0, 1H), 2.97-2.91 (m, 1H), 2.60-2.56 (m, 3H), 2.52 (s, 3H), 2.46-2.33 (m, 3H), 2.16 (s, 1H), 2.08-1.99 (m, 3H), 1.62-1.59 (m, 1H), 1.45-1.37 (m, 4H), 1.37-1.35 (m, 1H). |
| 125 | [3-(3-fluoro-5-methoxy-phenyl)-bicyclo[3.2.1]oct-2-ylmethyl]-dimethyl-amine hydrochloride | 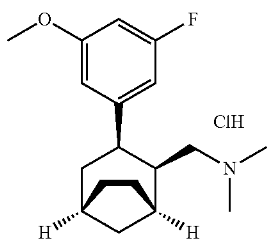 | ¹H NMR (400 MHz, D₂O) δ 6.61-6.59 (d, J = 8.0, 2H), 6.52-6.50 (m, 1H), 3.66 (s, 3H), 2.94-2.90 (m, 1H), 2.58-2.52 (m, 6H), 2.37-2.33 (m, 2H), 2.16 (s, 1H), 2.06-2.03 (m, 2H), 1.61-1.36 (m, 8H). |
| 126 | 3-(2-dimethylamino-methyl-bicyclo[3.2.1]oct-3-yl)-4-fluoro-phenol hydrochloride | 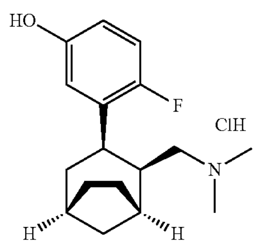 | ¹H NMR (400 MHz, D₂O) δ 6.91-6.83 (m, 1H), 6.74 (s, 1H), 6.62-6.49 (m, 1H), 3.03-2.94 (m, 1H), 2.49 (s, 4H), 2.42-2.35 (m, 2H), 2.19-2.08 (m, 6H), 1.63-1.40 (m, 7H). |
| 127 | [3-(2-fluoro-5-methoxy-phenyl)-bicyclo[3.2.1]oct-2-ylmethyl]-dimethyl-amine hydrochloride | 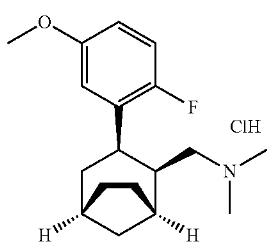 | ¹H NMR (400 MHz, D₂O) δ 6.98-6.86 (m, 1H), 6.76 (s, 1H), 6.75-6.74 (m, 1H), 3.68 (s, 3H), 3.04-2.98 (m, 1H), 2.81 (s, 1H), 2.64-2.55 (m, 6H), 2.36-2.39 (d, J = 12.0, 1H), 2.21 (s, 1H), 2.06-1.98 (m, 2H), 1.69-1.42 (m, 8H). |
| 128 | 3-(2-dimethylamino-methyl-bicyclo[3.2.1]oct-3-yl)-5-methyl-phenol hydrochloride | 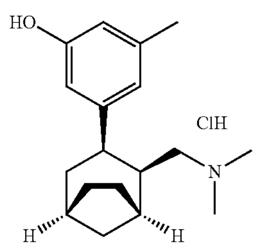 | ¹H NMR (400 MHz, Methanol-d4) δ 6.59 (s, 1H), 6.51 (s, 2H), 3.06-3.12 (m, 1H), 2.67-2.80 (m, 6H), 2.53-2.54 (m, 1H), 2.33-2.38 (m, 3H), 2.28 (s, 3H), 2.17-2.21 (t, J = 12.0, 1H), 1.52-1.87 (m, 8H). |

| Ex. No. | Chemical name | Structure | Physical data |
|---|---|---|---|
| 129 | [3-(3-methoxy-5-methyl-phenyl)-bicyclo[3.2.1]oct-2-ylmethyl]dimethyl-amine hydrochloride | 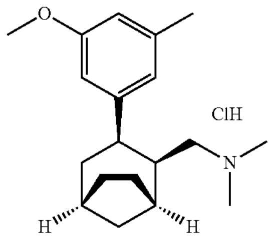 | $^1$H NMR (400 MHz, Methanol-d4) δ 6.71 (s, 1H), 6.64-6.65 (d, J = 5.6, 2H), 3.80 (s, 3H), 3.13-3.34 (m, 1H), 2.82-2.83 (d, J = 2.4, 3H), 2.72 (d, J = 2.4, 3H), 2.51-2.55 (m, 1H), 2.35-2.44 (m, 6H), 2.23-2.26 (t, J = 11.2, 1H), 1.60-1.85 (m, 8H). |

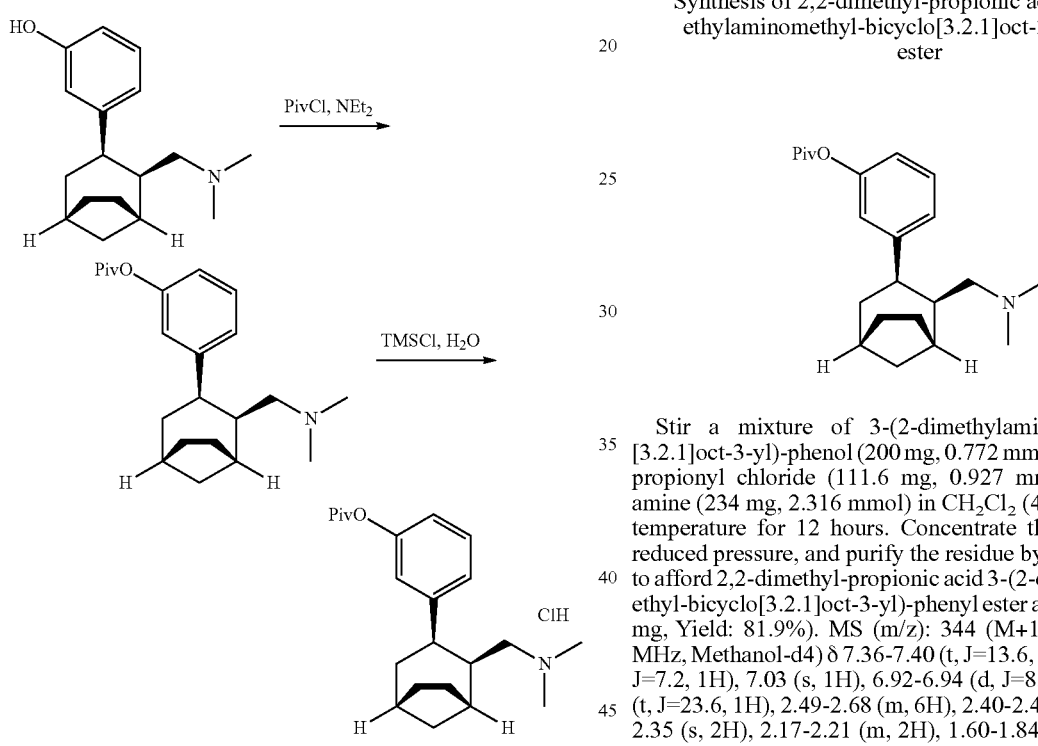

Scheme G

EXAMPLE 130

Synthesis of 2,2-dimethyl-propionic acid 3-(2-dimethylaminomethyl-bicyclo[3.2.1]oct-3-yl)-phenyl ester Stir a mixture of 3-(2-dimethylaminomethyl-bicyclo[3.2.1]oct-3-yl)-phenol (200 mg, 0.772 mmol), 2,2-dimethyl-propionyl chloride (111.6 mg, 0.927 mmol) and triethyl amine (234 mg, 2.316 mmol) in CH$_2$Cl$_2$ (40 mL) at ambient temperature for 12 hours. Concentrate the mixture under reduced pressure, and purify the residue by preparative TLC to afford 2,2-dimethyl-propionic acid 3-(2-dimethylaminomethyl-bicyclo[3.2.1]oct-3-yl)-phenyl ester as white solid (217 mg, Yield: 81.9%). MS (m/z): 344 (M+1). $^1$H NMR (400 MHz, Methanol-d4) δ 7.36-7.40 (t, J=13.6, 1H), 7.19-7.21 (d, J=7.2, 1H), 7.03 (s, 1H), 6.92-6.94 (d, J=8.0, 1H), 2.97-3.03 (t, J=23.6, 1H), 2.49-2.68 (m, 6H), 2.40-2.44 (d, J=13.2, 1H), 2.35 (s, 2H), 2.17-2.21 (m, 2H), 1.60-1.84 (m, 8H), 1.37 (s, 9H).

The following compounds are prepared essentially by the method of Example 130.

| Ex. | Chemical name | Structure | Physical data |
|---|---|---|---|
| 131 | benzoic acid 3-(2-dimethyl-aminomethyl-bicyclo[3.2.1]oct-3-yl)-phenyl ester | 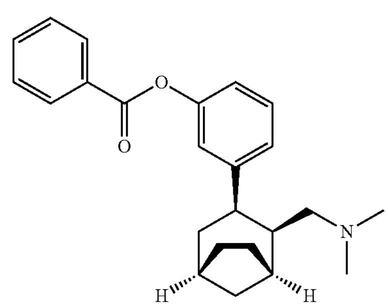 | MS (m/z): 364 (M + 1), $^1$H NMR (400 MHz, CDCl$_3$) δ 8.19-8.22 (m, 2H), 7.63-7.64 (t, J = 7.6, 1H), 7.50-7.52 (t, J = 7.6, 2H), 7.32-7.36 (t, J = 16.4, 1H), 7.04-7.10 (m, 3H), 2.46 (s, 1H), 2.19-2.39 (m, 3H), 2.10 (s, 6H), 1.80-1.90 (t, J = 37.2, 1H), 1.52-1.71 (m, 9H). |

-continued

| Ex. | Chemical name | Structure | Physical data |
|---|---|---|---|
| 132 | 2,2-dimethyl-propionic acid 3-(2-dimethylamino-methyl-bicyclo[3.2.1]oct-3-yl)-5-fluoro-phenyl ester | 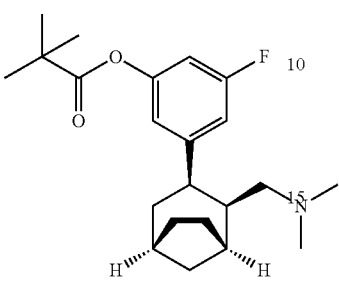 | MS (m/z): 362 (M + 1), $^1$H NMR (400 MHz, Methanol-d4) δ 6.96-6.98 (d, J = 10.0, 1H), 6.84 (s, 1H), 6.73-6.76 (m, 1H), 2.66-2.72 (m, 1H), 2.49-2.54 (m, 1H), 2.30-2.37 (m, 8H), 2.04-2.07 (m, 2H), 1.56-1.81 (m, 8H), 1.36 (s, 9H). |
| 133 | isobutyric acid 3-(2-dimethyl-aminomethyl-bicyclo[3.2.1]oct-3-yl)-5-fluoro-phenyl ester | 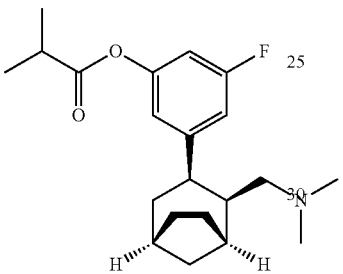 | MS (m/z): 348 (M + 1). $^1$H NMR (400 MHz, Methanol-d4) δ 6.82-6.85 (d, J = 9.6, 1H), 6.73 (s, 1H), 6.62-6.65 (m, 1H), 2.68-2.75 (m, 1H), 2.34-2.46 (m, 3H), 2.15-2.28 (m, 1H), 2.15 (s, 6H), 1.76-1.81 (m, 2H), 1.44-1.69 (m, 8H), 1.19-1.20 (d, J = 7.2, 6H). |
| 134 | 2,2-dimethyl-propionic acid 3-(2-dimethylamino-methyl-bicyclo[3.2.1]oct-3-yl)-4-fluoro-phenyl ester | 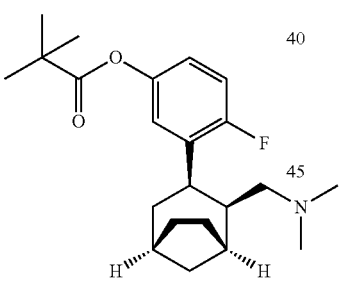 | MS (m/z): 362 (M + 1). $^1$H NMR (Methanol-d4, 400 MHz) δ 7.10 (t, J = 8.8, 2H), 6.90 (m, 1H), 2.92 (m, 1H), 2.43 (s, 1H), 2.33 (m, 2H), 2.03 (s, 6H), 1.90 (s, 1H), 1.50-1.82 (m, 9H), 1.45 (s, 9H). |
| 135 | isobutyric acid 3-(2-dimethyl-aminomethyl-bicyclo[3.2.1]oct-3-yl)-4-fluoro-phenyl ester | 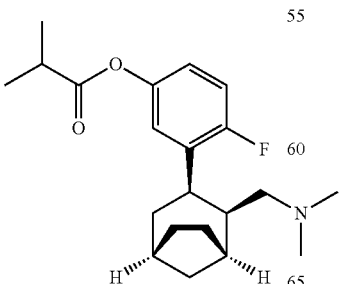 | MS (m/z): 348 (M + 1). $^1$H NMR (Methanol-d4, 400 MHz) δ 7.13 (t, J = 8.4, 2H), 6.90 (m, 1H), 2.85 (m, 2H), 2.40 (s, 1H), 2.33 (m, 2H), 2.06 (s, 6H), 1.50-1.88 (m, 10H), 1.31 (d, J = 6.4, 6H). |

EXAMPLE 136

Synthesis of 2,2-dimethyl-propionic acid 3-(2-dimethylaminomethyl-bicyclo[3.2.1]oct-3-yl)-phenyl ester hydrochloride

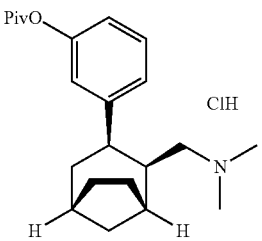

Add H$_2$O (9 mg, 0.5 mmol) and TMSCl (39 mg, 0.357 mmol) to a solution of 2,2-dimethyl-propionic acid 3-(2-dimethylaminomethyl-bicyclo[3.2.1]oct-3-yl)-phenyl ester (102 mg, 0.297 mmol) in 2-butanone (50 mL). Then stir the reaction mixture at ambient temperature for 4 hours. Evaporate the mixture under vacuum to give 2,2-dimethyl-propionic acid 3-(2-dimethylaminomethyl-bicyclo[3.2.1]oct-3-yl)-phenyl ester hydrochloride as white solid (112 mg, Yield: 100%). $^1$H NMR (400 MHz, Methanol-d4) δ 7.38-7.42 (t, J=15.6, 1H), 7.20-7.22 (d, J=7.6, 1H), 7.05 (s, 1H), 6.94-6.96 (m, 1H), 3.08-3.14 (m, 1H), 2.79 (s, 3H), 2.66 (s, 3H), 2.53-2.57 (m, 2H), 2.36 (s, 2H), 2.23 (m, 1H), 1.61-1.85 (m, 8H), 1.39 (s, 9H).

The following compounds may be prepared essentially by the method of Example 135.

| Ex. No. | Chemical name | Structure | Physical data |
|---|---|---|---|
| 137 | 2,2-dimethyl-propionic acid 3-(2-dimethylaminomethyl-bicyclo[3.2.1]oct-3-yl)-5-fluoro-phenyl ester hydrochloride | 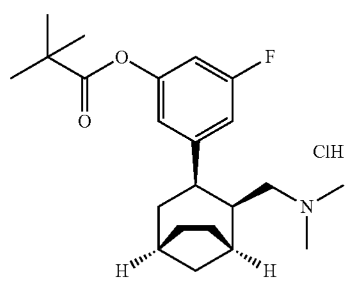 | $^1$H NMR (400 MHz, Methanol-d4) δ 7.04-7.06 (d, J = 9.6, 1H), 6.92 (s, 1H), 6.78-6.81 (m, 1H), 3.10-3.16 (m, 1H), 2.70-2.81 (m, 6H), 2.52-2.58 (m, 2H), 2.36 (s, 2H), 2.24 (m, 1H), 1.58-1.86 (m, 8H), 1.37 (s, 9H). |
| 138 | isobutyric acid 3-(2-dimethylaminomethyl-bicyclo[3.2.1]oct-3-yl)-5-fluoro-phenyl ester hydrochloride | 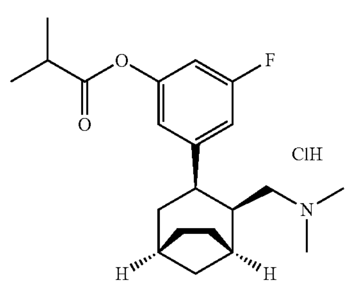 | $^1$H NMR (400 MHz, Methanol-d4) δ 7.03-7.06 (d, J = 9.6, 1H), 6.95 (s, 1H), 6.79-6.83 (m, 1H), 3.10-3.16 (m, 1H), 2.82-2.90 (m, 1H), 2.81 (s, 3H), 2.69 (s, 3H), 2.52-2.58 (m, 2H), 2.37-2.38 (m, 2H), 2.22-2.27 (m, 1H), 1.56-1.85 (m, 8H), 1.31 (s, 6H). |
| 139 | 2,2-dimethyl-propionic acid 3-(2-dimethylaminomethyl-bicyclo[3.2.1]oct-3-yl)-4-fluoro-phenyl ester hydrochloride | 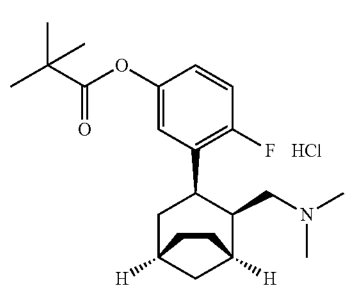 | $^1$H NMR (400 MHz, Methanol-d4) δ 7.22 (m, 2H), 6.95 (s, 1H), 3.12 (t, J = 11.2, 1H), 2.98 (s, 1H), 2.72 (s, 6H), 2.45 (d, J = 12.8, 1H), 2.39 (s, 2H), 2.25 (s, 1H), 1.84 (m, 1H), 1.52-1.81 (m, 7H), 1.47 (s, 9H). |

| Ex. No. | Chemical name | Structure | Physical data |
|---|---|---|---|
| 140 | isobutyric acid 3-(2-dimethylaminomethyl-bicyclo[3.2.1]oct-3-yl)-4-fluoro-phenyl ester hydrochloride | 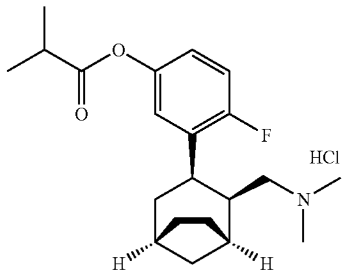 | 1H NMR (400 MHz Methanol-d4) δ 7.26 (s, 1H), 7.15 (m, 1H), 7.01 (s, 1H), 3.16 (t, J = 10.8, 1H), 2.98 (s, 1H), 2.84 (m, 3H), 2.70 (s, 3H), 2.53 (m, 1H), 2.41 (s, 1H), 2.38 (s, 1H), 2.27 (s, 1H), 1.53-1.92 (m, 9H), 1.29 (d, J = 6.8, 6H). |

For compounds of the formula Id, below, Schemes H-J and Preparations and/or Examples 147-164 illustrate methods of preparing them.

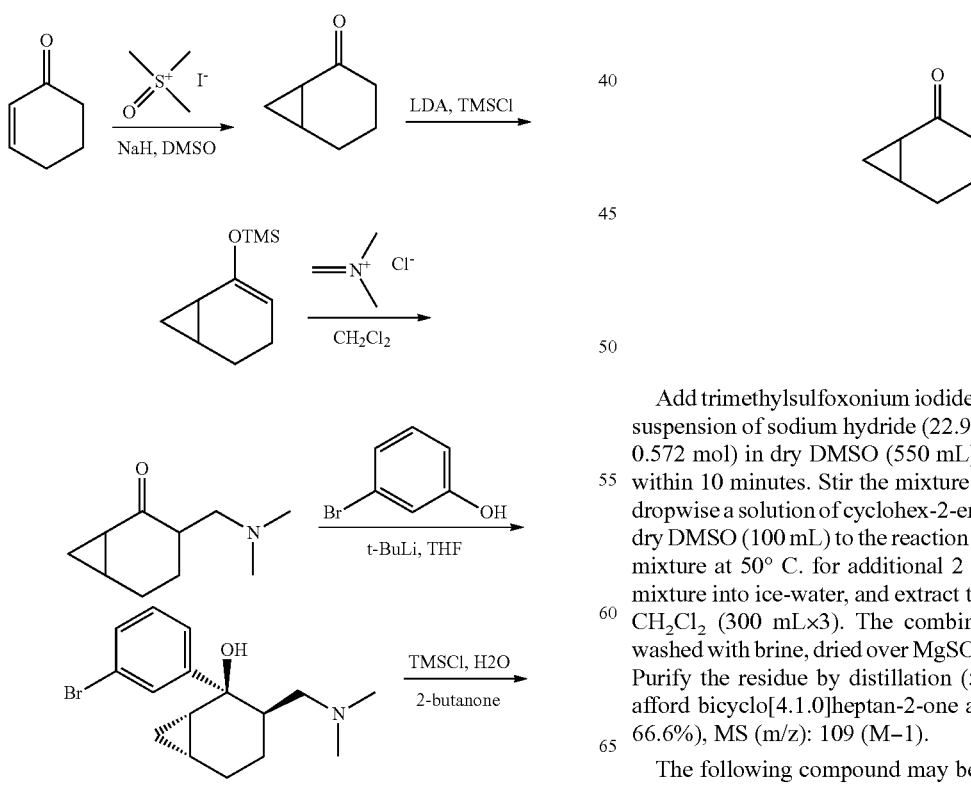

Scheme H

PREPARATION 141

Synthesis of bicyclo[4.1.0]heptan-2-one

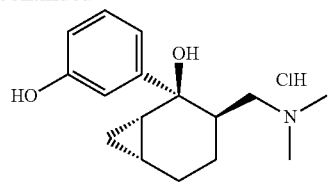

Add trimethylsulfoxonium iodide (126.3 g, 0.572 mol) to a suspension of sodium hydride (22.9 g, 60% in oil dispersion, 0.572 mol) in dry DMSO (550 mL) at ambient temperature within 10 minutes. Stir the mixture for 1 hour, and then add dropwise a solution of cyclohex-2-enone (51.2 g, 0.52 mol) in dry DMSO (100 mL) to the reaction mixture. Stir the reaction mixture at 50° C. for additional 2 hours. Pour the reaction mixture into ice-water, and extract the aqueous mixture with $CH_2Cl_2$ (300 mL×3). The combined organic layers were washed with brine, dried over $MgSO_4$, concentrated in vacuo. Purify the residue by distillation (55~60° C., 5 mmHg) to afford bicyclo[4.1.0]heptan-2-one as colorless oil (38.45 g, 66.6%), MS (m/z): 109 (M−1).

The following compound may be prepared essentially by the method of Preparation 141.

| Prep No. | Chemical name | Structure | Physical data |
|---|---|---|---|
| 142 | 5,5-Dimethyl-bicyclo[4.1.0]heptan-2-one | 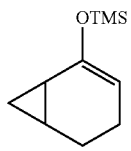 | MS (m/z): 137 (M − 1). |

PREPARATION 143

Synthesis of (bicyclo[4.1.0]hept-2-en-2-yloxy)-trimethyl-silane

Add dropwise bicyclo[4.1.0]heptan-2-one (43.3 g, 0.393 mol) in dry THF (50 mL) to a solution of LDA (237 mL, 0.472 mol) in THF (500 mL). Stir the reaction mixture for 30 min and then add dropwise TMSCl (64.2 g, 0.59 mol) to the reaction mixture. Stir the resultant solution for additional 1 hour. Pour the mixture into ice water (92 mL) and extract the aqueous mixture with EtOAc (100 mL×3). The combined organic layers are washed with brine, dried over MgSO₄, filtered and concentrated in vacuo to afford crude (bicyclo[4.1.0]hept-2-en-2-yloxy)-trimethyl-silane (68.0 g, 95.0%) as yellowish oil, MS (m/z): 181 (M−1).

The following compound may be prepared essentially by the method of Preparation 143.

| Prep No. | Chemical name | Structure | Physical data |
|---|---|---|---|
| 144 | (5,5-Dimethyl-bicyclo[4.1.0]hept-2-en-2-yloxy)-trimethyl-silane | 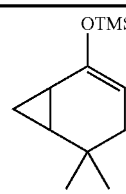 | MS (m/z): 209 (M − 1). |

PREPARATION 145

Synthesis of 3-dimethylaminomethyl-bicyclo[4.1.0]heptan-2-one

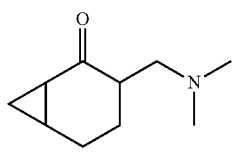

Add (bicyclo[4.1.0]hept-2-en-2-yloxy)-trimethyl-silane (72.9 g, 0.40 mol) to a cooled suspension of N,N-dimethyl-methyleneiminium chloride (48.6 g, 0.52 mol) in CH₂Cl₂ (400 mL) at 0° C. After being stirred for overnight at ambient temperature, dilute the reaction mixture with 2 N HCl (200 mL). After removal of organic layers, wash the aqueous layer with EtOAc (50 mL×3) and then basify with NaOH to PH=10. Extract the resultant mixture with EtOAc (100 mL×4). The combined organic layers are washed with brine, dried over Na₂SO₄, filtered and concentrated in vacuo. Purify the residue by distillation (80~85° C., 5 mmHg) to afford 3-dimethylaminomethyl-bicyclo[4.1.0]heptan-2-one (16.0 g, 24.0%) as colorless oil, MS (m/z): 168 (M+1).

The following compound may be prepared essentially by the method of Preparation 145.

| Prep No. | Chemical name | Structure | Physical data |
|---|---|---|---|
| 146 | 3-Dimethylaminomethyl-5,5-dimethyl-bicyclo[4.1.0]heptan-2-one | 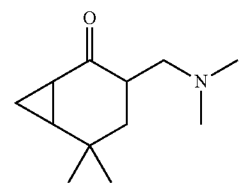 | MS (m/z): 196 (M + 1). |

EXAMPLE 147

Synthesis of 3-Dimethylaminomethyl-2-(3-hydroxy-phenyl)-bicyclo[4.1.0]heptan-2-ol

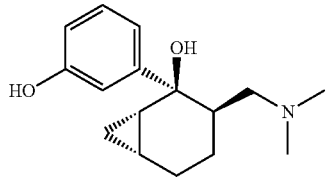 [SMILES: CN(C)C[C@H]1CC[C@@H]2C[C@@H]2[C@]1(O)c1cccc(O)c1]

Add a solution of t-BuLi (5.8 mL, 8.68 mmol) via syringe to a solution of 3-bromo-phenol (752 mg, 4.34 mmol) in THF (60 mL) at −78° C. under N₂. After being stirred at −78° C. for 1 hour, add a solution of 3-dimethylaminomethyl-bicyclo[4.1.0]heptan-2-one (300 mg, 2.17 mmol) in THF (2 mL) to the reaction mixture and stir the reaction mixture at −78° C. for additional 2 hours. Quench the reaction mixture with saturated NH₄Cl solution (30 mL). Extract the aqueous resultant mixture with EtOAc (60 mL×3). The combined organic layers are washed with brine (30 mL), dried over Na₂SO₄, filtered, and concentrated under vacuum. Purify the residue by Preparative HPLC to give 3-dimethylaminomethyl-2-(3-hydroxy-phenyl)-bicyclo[4.1.0]heptan-2-ol as white solid (73 mg, yield: 12.9%). MS (m/z): 262 (M+1).

The following compounds may be prepared essentially by the method of Example 147.

| Ex. No. | Chemical name | Structure | Physical data |
|---|---|---|---|
| 148 | 3-Dimethylaminomethyl-2-(3-methoxy-phenyl)-bicyclo[4.1.0]heptan-2-ol | 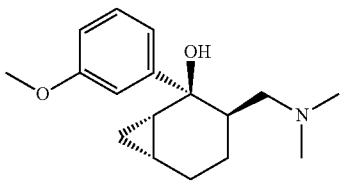 | MS (m/z): 276 (M + 1). |
| 149 | 3-Dimethylaminomethyl-2-(3-fluoro-5-methoxy-phenyl)-bicyclo[4.1.0]heptan-2-ol | 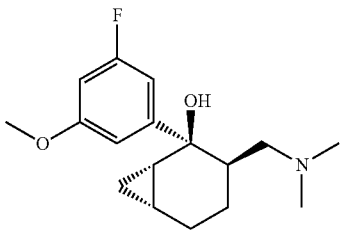 | MS (m/z): 294 (M + 1). |
| 150 | 3-Dimethylaminomethyl-2-(5-methoxy-2-methyl-phenyl)-bicyclo[4.1.0]heptan-2-ol | 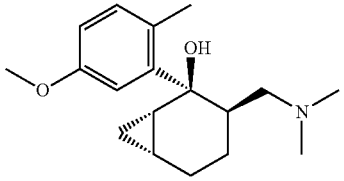 | MS (m/z): 290 (M + 1). |
| 151 | 3-Dimethylaminomethyl-2-(3-methoxy-phenyl)-5,5-dimethyl-bicyclo[4.1.0]heptan-2-ol | 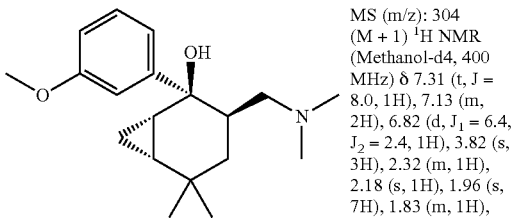 | MS (m/z): 304 (M + 1) $^1$H NMR (Methanol-d4, 400 MHz) δ 7.31 (t, J = 8.0, 1H), 7.13 (m, 2H), 6.82 (d, $J_1$ = 6.4, $J_2$ = 2.4, 1H), 3.82 (s, 3H), 2.32 (m, 1H), 2.18 (s, 1H), 1.96 (s, 7H), 1.83 (m, 1H), 1.38 (m, 1H), 1.28 (m, 3H), 1.22 (m, 2H), 1.10 (s, 3H), 1.02 (m, 1H), 0.61 (m, 1H), 0.50 (m, 1H). |
| 152 | 3-Dimethylaminomethyl-2-(3-hydroxy-phenyl)-5,5-dimethyl-bicyclo[4.1.0]heptan-2-ol | 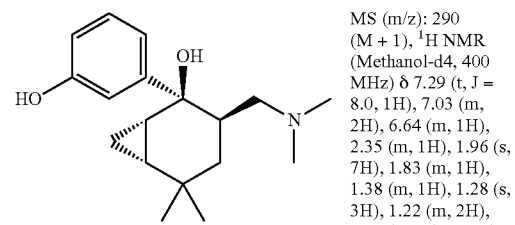 | MS (m/z): 290 (M + 1), $^1$H NMR (Methanol-d4, 400 MHz) δ 7.29 (t, J = 8.0, 1H), 7.03 (m, 2H), 6.64 (m, 1H), 2.35 (m, 1H), 1.96 (s, 7H), 1.83 (m, 1H), 1.38 (m, 1H), 1.28 (s, 3H), 1.22 (m, 2H), 1.10 (s, 3H), 1.02 (m, 1H), 0.61 (m, 1H), 0.50 (m, 1H). |

EXAMPLE 153

Synthesis of 3-dimethylaminomethyl-2-(3-hydroxy-phenyl)-bicyclo[4.1.0]heptan-2-ol hydrochloride

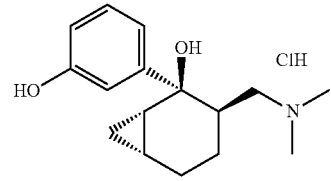 [SMILES: CN(C)C[C@H]1CC[C@@H]2C[C@@H]2[C@]1(O)c1cccc(O)c1 ; Cl]

Add H₂O (10 mg, 0.560 mmol) and TMSCl (33 mg, 0.308 mmol) to a solution of 3-dimethylaminomethyl-2-(3-hydroxy-phenyl)-bicyclo[4.1.0]heptan-2-ol (73 mg, 0.280 mmol) in 2-butanone (10 mL). Then stir the mixture at room temperature for 2 hours. Evaporate the mixture under vacuum to give 3-dimethylaminomethyl-2-(3-hydroxyl-phenyl)-bicyclo[4.1.0]heptan-2-ol hydrochloride as white solid (83 mg, Yield: 100%). $^1$H NMR (400 MHz, Methanol-d4) δ 7.21-7.25 (t, J=16.0, 1H), 7.17-7.18 (t, J=4.4, 1H), 7.11-7.13 (m, 1H), 6.76-6.79 (d, J=10.0, 1H), 3.23-3.25 (m, 1H), 2.68-2.69 (m, 7H), 2.14-2.17 (m, 1H), 2.04-2.09 (m, 1H), 1.76-1.81 (m, 1H), 1.62-1.64 (m, 1H), 1.47-1.49 (m, 1H), 1.11-1.16 (m, 1H), 0.93-1.05 (m, 1H), 0.73-0.84 (m, 1H), 0.50-0.53 (m, 1H).

The following compounds may prepared essentially by the method of Example 153.

Scheme I

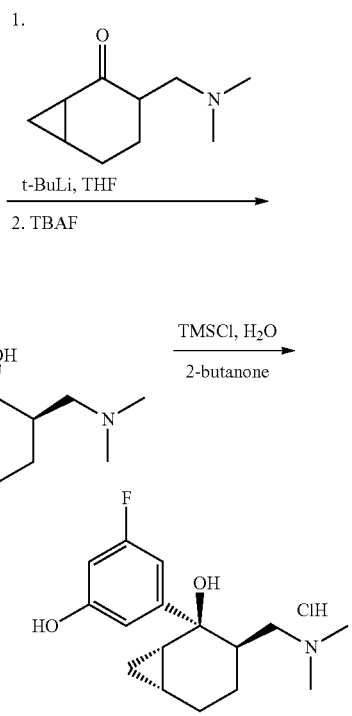

| Ex. No. | Chemical name | Structure | Physical data |
|---|---|---|---|
| 154 | 3-Dimethylaminomethyl-2-(3-methoxy-phenyl)-bicyclo[4.1.0] heptan-2-ol hydrochloride | 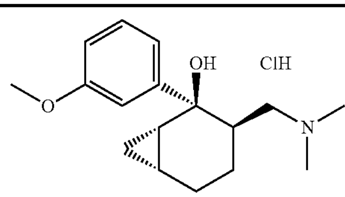 | $^1$H NMR (400 MHz, Methanol-d4) δ 7.23 (m, 1H), 7.17 (m, 1H), 7.11 (m, 1H), 6.78 (m, 1H), 3.72 (s, 3H), 2.95 (m, 1H), 2.60-2.71 (m, 7H), 2.16 (m, 1H), 2.05 (m, 1H), 1.80 (m, 1H), 1.65 (m, 1H), 1.48 (m, 1H), 1.15 (m, 1H), 1.01 (m, 1H), 0.67 (m, 1H), 0.50 (m, 1H). |
| 155 | 3-Dimethylaminomethyl-2-(3-fluoro-5-methoxy-phenyl)-bicyclo[4.1.0] heptan-2-ol hydrochloride | 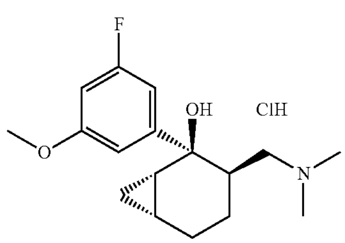 | $^1$H NMR (400 MHz, Methanol-d4) δ 7.08 (d, J = 1.6, 1H), 7.00 (m, 1H), 6.62 (m,1H), 3.82 (s, 3H), 3.02 (m, 1H), 2.75 (m, 7H), 2.23 (m, 1H), 2.10 (m, 1H), 1.81 (m, 1H), 1.73 (m, 1H), 1.62 (m, 1H), 1.26 (m, 1H), 1.12 (m, 1H), 0.85 (m, 1H), 0.64 (m, 1H). |
| 156 | 3-Dimethylaminomethyl-2-(5-methoxy-2-methyl-phenyl)-bicyclo[4.1.0] heptan-2-ol hydrochloride | 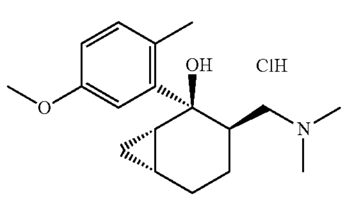 | $^1$H NMR (400 MHz, Methanol-d4) δ 7.10-7.12 (d, J = 8.0, 1H), 6.92 (s, 1H), 6.75-6.77 (d, J = 8.0, 1H), 3.79 (s, 3H), 3.12 (s, 2H), 2.85 (s, 6H), 2.59 (s, 3H), 2.47 (s, 1H), 2.15-2.16 (m, 1H), 1.63-1.80 (m, 3H), 1.41-1.44 (m, 1H), 1.25-1.29 (m, 1H), 0.70-0.71 (m, 1H), 0.25-0.26 (m, 1H). |

EXAMPLE 157

Synthesis of 3-dimethylaminomethyl-2-(3-fluoro-5-hydroxy-phenyl)-bicyclo[4.1.0]heptan-2-ol

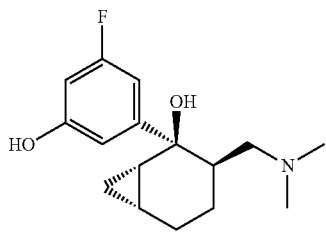 [SMILES: CN(C)C[C@H]1CC[C@@H]2C[C@@H]2[C@]1(O)c1cc(O)cc(F)c1]

Add a solution of t-BuLi (19.4 mL, 25.2 mmol) via syringe to a solution of (3-bromo-5-fluoro-phenoxy)-tert-butyl-dimethyl-silane (6.99 g, 22.9 mmol) in THF (100 mL) at −78° C. under $N_2$. After being stirred at −78° C. for 1 hour, add dropwise a solution of 3-dimethylaminomethyl-bicyclo[4.1.0]heptan-2-one (2.55 g, 15.3 mmol) to the reaction mixture and stir the reaction mixture at −78° C. for additional 2 hours. Quench the reaction with saturated $NH_4Cl$ solution (30 mL). Extract the resultant aqueous mixture with EtOAc (100 mL×3). The combined organic layers are washed with brine (30 mL), dried over $Na_2SO_4$, filtered, and concentrated under vacuum. Treat the residue with TBAF (6.00 g, 22.9 mmol) in $CH_2Cl_2$ (80 mL) at ambient temperature for 4 hours. Concentrate the mixture, and purify the residue by preparative HPLC to give 3-dimethylaminomethyl-2-(3-fluoro-5-hydroxy-phenyl)-bicyclo[4.1.0]heptan-2-ol as white solid (592 mg, yield: 13.9%). MS (m/z): 280 (M+1).

The following compounds may be prepared essentially by the method of Example 157.

EXAMPLE 160

Synthesis of 3-dimethylaminomethyl-2-(3-fluoro-5-hydroxy-phenyl)-bicyclo[4.1.0]heptan-2-ol hydrochloride

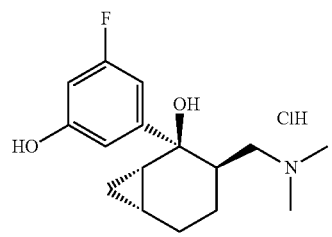

Add $H_2O$ (18 mg, 1.0 mmol) and TMSCl (92 mg, 0.857 mmol) to a solution of 3-dimethylaminomethyl-2-(3-fluoro-5-hydroxy-phenyl)-bicyclo[4.1.0]heptan-2-ol (218 mg, 0.781 mmol) in 2-butanone (70 mL). Then stir the reaction mixture at room temperature for 2 hours. After removal the solvent by evaporation, wash the residue with EtOAc (3 mL×2) to give 3-dimethylaminomethyl-2-(3-fluoro-5-hydroxy-phenyl)-bicyclo[4.1.0]heptan-2-ol hydrochloride as white solid (72 mg, Yield: 67.8%). $^1$H NMR (400 MHz, $D_2O$) δ 6.93 (s, 1H), 6.87-6.89 (d, J=9.6, 1H), 6.42-6.58 (m, 1H), 3.32-3.33 (t, J=3.2, 1H), 2.98-3.04 (m, 1H), 2.77 (m, 6H), 2.22-2.23 (m, 1H), 2.06 (m, 1H), 1.81-1.85 (m, 2H), 1.61-1.71 (m, 1H), 1.17-1.21 (m, 1H), 1.08-1.10 (m, 1H), 0.83-0.86 (m, 1H), 0.56-0.60 (m, 1H).

The following compounds may be prepared essentially by the method of Example 160.

| Ex. No. | Chemical name | Structure | Physical data |
|---|---|---|---|
| 158 | 3-Dimethylaminomethyl-2-(2-fluoro-5-hydroxy-phenyl)-bicyclo[4.1.0]heptan-2-ol | 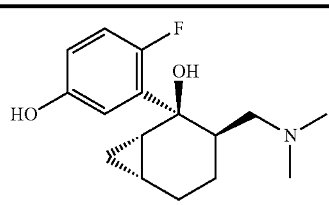 | MS (m/z): 280 (M + 1). |
| 159 | 3-Dimethylaminomethyl-2-(3-hydroxy-5-methyl-phenyl)-bicyclo[4.1.0]heptan-2-ol | 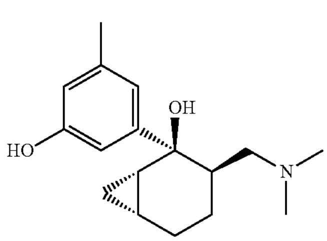 [SMILES: Cc1cc(O)cc([C@]2(O)[C@@H](CN(C)C)CC[C@@H]3C[C@@H]32)c1] | MS (m/z): 276 (M + 1). |

| Ex. No. | Chemical name | Structure | Physical data |
|---|---|---|---|
| 161 | 3-Dimethylaminomethyl-2-(2-fluoro-5-hydroxy-phenyl)-bicyclo[4.1.0]heptan-2-ol hydrochloride | 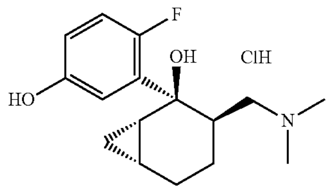 [SMILES: CN(C)C[C@H]1CC[C@@H]2C[C@@H]2[C@]1(O)c1cc(O)ccc1F ; Cl] | $^1$H NMR (400 MHz, Methanol-d4) δ 7.27-7.30 (m, 1H), 6.91 (m, 1H), 6.69-6.73 (m, 1H), 3.06-3.11 (m, 1H), 2.76-2.86 (m, 7H), 2.46-2.54 (m, 1H), 2.20-2.26 (m, 1H), 1.83-1.87 (m, 1H), 1.64-1.71 (m, 1H), 1.52-1.57 (m, 1H), 1.19-1.21 (m, 1H), 1.02-1.14 (m, 1H), 0.73-0.79 (m, 1H), 0.59-0.63 (m, 1H). |
| 162 | 3-Dimethylaminomethyl-2-(3-hydroxy-5-methyl-phenyl)-bicyclo[4.1.0]heptan-2-ol hydrochloride | 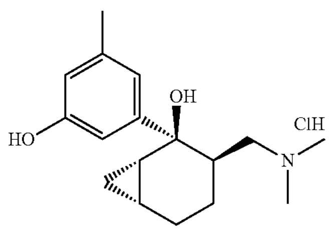 [SMILES: Cc1cc(O)cc([C@]2(O)[C@@H](CN(C)C)CC[C@@H]3C[C@@H]32)c1 ; Cl] | $^1$H NMR (400 MHz, Methanol-d4) δ 6.95 (s, 1H), 6.91 (s, 1H), 6.56 (s, 1H), 2.97-3.04 (m, 1H), 2.78-2.82 (d, $J_1$ = 13.2, $J_2$ = 2.0, 1H), 2.74 (s, 6H), 2.31 (s, 3H), 2.20-2.27 (m, 1H), 2.05-2.10 (m, 1H), 1.80-1.87 (m, 1H), 1.68-1.76 (m, 1H), 1.55-1.60 (m, 1H), 1.17-1.21 (m, 1H), 1.06-1.12 (m, 1H), 0.86 (m, 1H), 0.58 (m, 1H). |

Scheme J

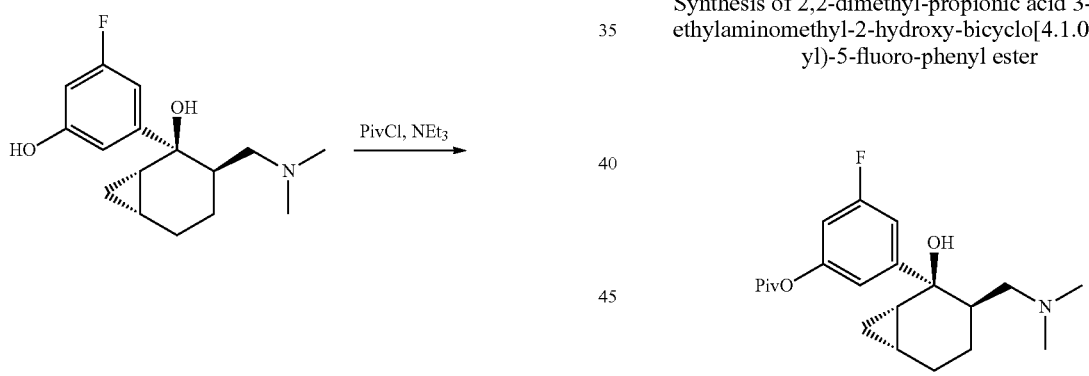

EXAMPLE 163

Synthesis of 2,2-dimethyl-propionic acid 3-(3-dimethylaminomethyl-2-hydroxy-bicyclo[4.1.0]hept-2-yl)-5-fluoro-phenyl ester Stir a mixture of 3-dimethylaminomethyl-2-(3-fluoro-5-hydroxy-phenyl)-bicyclo[4.1.0]heptan-2-ol (295 mg, 1.06 mmol), 2,2-dimethyl-propionyl chloride (153 mg, 1.27 mmol) and triethyl-amine (321 mg, 3.18 mmol) in $CH_2Cl_2$ (40 mL) at ambient temperature for 5 hours. Quench the mixture with 10 mL of $H_2O$, Separate the aqueous layer off, and concentrate the organic layer under reduced pressure. Purify the residue by preparative TLC to give 2,2-dimethyl-propionic acid 3-(3-dimethylaminomethyl-2-hydroxy-bicyclo[4.1.0]hept-2-yl)-5-fluoro-phenyl ester as white solid (228 mg, Yield: 59.2%). MS (m/z): 364 (M+1). $^1$H NMR (400 MHz, Methanol-d4) δ 7.25-7.28 (d, $J_1$=10.4, $J_2$=1.6, 1H), 7.14 (s, 1H), 6.76-6.78 (d, $J_1$=9.2, $J_2$=2.4, 1H), 2.37-2.46 (m, 1H), 2.15-2.19 (m, 7H), 1.99-2.03 (d, J=13.2, 1H), 1.82 (m, 2H), 1.53-1.68 (m, 2H), 1.37 (s, 9H), 1.17 (m, 1H), 1.01-1.06 (m, 1H), 0.75-0.81 (m, 1H), 0.48-0.50 (m, 1H).

The following compound may be prepared essentially by the method of Example 163.

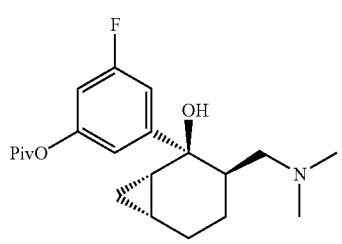

| Ex. No. | Chemical name | Structure | Physical data |
|---|---|---|---|
| 164 | 2,2-Dimethyl-propionic acid 3-(3-dimethylaminomethyl-2-hydroxy-bicyclo[4.1.0]hept-2-yl)-4-fluoro-phenyl ester | 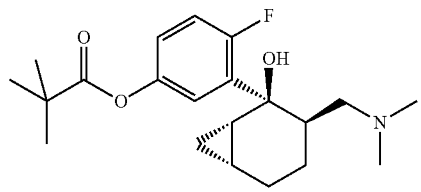 [SMILES: CN(C)C[C@H]1CC[C@@H]2C[C@@H]2[C@]1(O)c1cc(OC(=O)C(C)(C)C)ccc1F] | MS (m/z): 364 (M + 1) $^{1}$H NMR (400 MHz, Methanol-d4) δ 7.50-7.53 (m, 1H), 7.06-7.15 (m, 1H), 6.96-7.00 (m, 1H), 2.41-2.44 (m, 1H), 2.17-2.22 (m, 2H), 2.02 (s, 5H), 1.98-2.02 (m, 2H), 1.80-1.85 (m, 1H), 1.52-1.64 (m, 2H), 1.38 (s, 9H), 1.13-1.22 (m, 1H), 1.02-1.06 (m, 1H), 0.70-0.72 (m, 1H), 0.59-0.636 (m, 1H). |

For compounds of the formula Ie, below, Scheme K and Preparations and/or Examples 165-176 illustrate methods of preparing them.

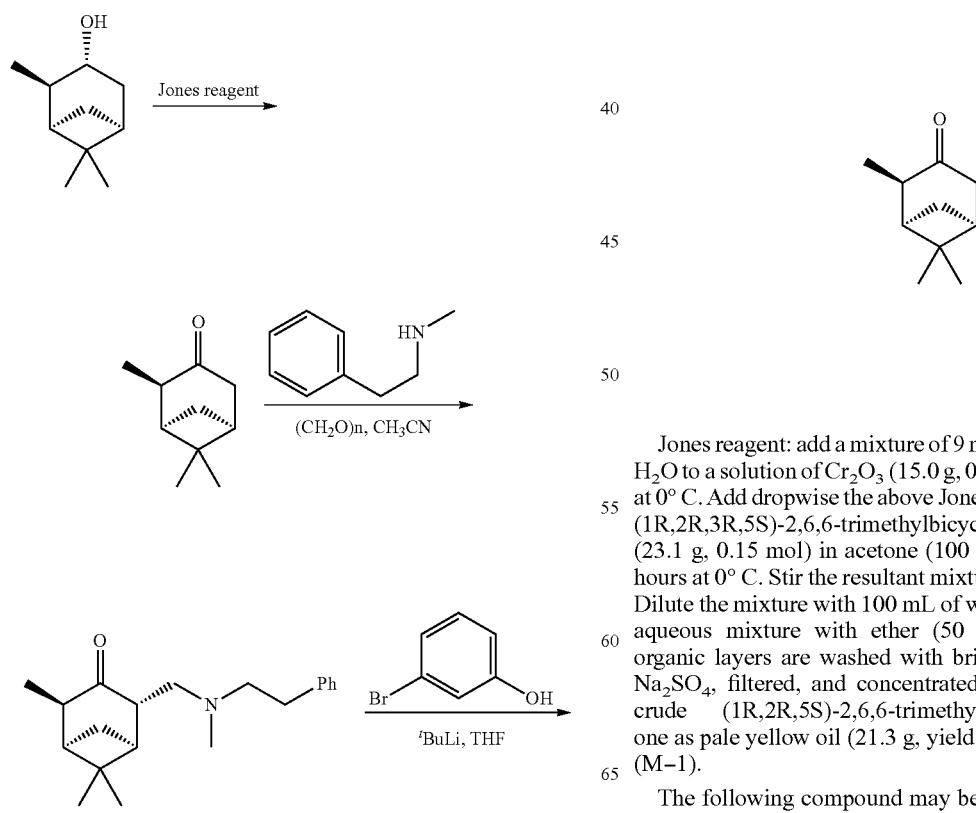

Scheme K

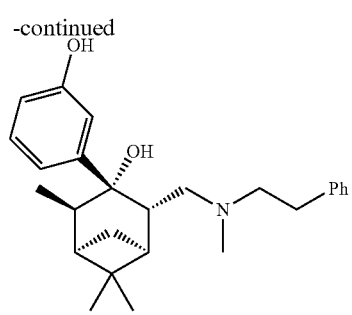

PREPARATION 165

(1R,2R,5S)-2,6,6-trimethylbicyclo[3.1.1]heptan-3-one

Jones reagent: add a mixture of 9 ml of $H_2SO_4$ and 40 ml of $H_2O$ to a solution of $Cr_2O_3$ (15.0 g, 0.15 mol) in $H_2O$ (20 mL) at 0° C. Add dropwise the above Jones reagent to a solution of (1R,2R,3R,5S)-2,6,6-trimethylbicyclo[3.1.1]heptan-3-ol (23.1 g, 0.15 mol) in acetone (100 mL) over a period for 2 hours at 0° C. Stir the resultant mixture for additional 1 hour. Dilute the mixture with 100 mL of water and then extract the aqueous mixture with ether (50 mL×3). The combined organic layers are washed with brine (20 mL), dried over $Na_2SO_4$, filtered, and concentrated under vacuum to give crude (1R,2R,5S)-2,6,6-trimethylbicyclo[3.1.1]heptan-3-one as pale yellow oil (21.3 g, yield: 93.4%), MS (m/z): 151 (M−1).

The following compound may be prepared essentially by the method of Preparation 165.

| Prep No. | Chemical name | Structure | Physical data |
|---|---|---|---|
| 166 | (1S,2S,5R)-2,6,6-trimethylbicyclo[3.1.1]heptan-3-one | 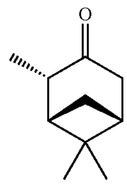 | MS (m/z): 151 (M − 1). |

PREPARATION 167

(1R,2R,4S,5S)-2,6,6-trimethyl-4-((methyl(phenethyl)amino)methyl)bicyclo[3.1.1]heptan-3-one

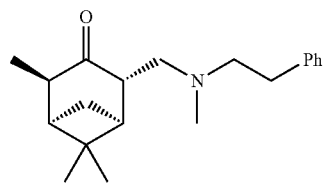 [SMILES: C[C@H]1C(=O)[C@H](CN(C)CCc2ccccc2)[C@@H]2C[C@H]1C2(C)C]

Stir a mixture of (1R,2R,5S)-2,6,6-trimethylbicyclo[3.1.1]heptan-3-one (7.6 g, 50.0 mmol), (HCHO)$_n$ (1.8 g, 60.0 mmol), N-methyl-2-phenylethanamine (6.75 g, 50.0 mmol) and 5.0 mL of conc. HCl in MeCN (50 mL) at 70° C. for 3 hours. After removal of the solvent under vacuum, dissolve the residue in H$_2$O (30 mL) and washed with EtOAc (20 mL×2). Basify the aqueous solution with K$_2$CO$_3$ to pH=9 and extract the resultant mixture with EtOAc (30 mL×3). The combined organic layers were washed with brine (20 mL), dried over Na$_2$SO$_4$, filtered, and concentrated under vacuum to give crude product as brown oil, which was further purified by silica gel chromatography to give (1R,2R,4S,5S)-2,6,6-trimethyl-4-((methyl(phenethyl)amino) methyl)bicycle[3.1.1]heptan-3-one as pale yellow oil (9.24 g, yield: 61.8%), MS (m/z): 300 (M+1).

The following compound may be prepared essentially by the method of Preparation 167.

EXAMPLE 169

(1R,2R,3S,4S,5S)-3-(3-hydroxyphenyl)-2,6,6-trimethyl-4-((methyl(phenethyl)amino)methyl)bicyclo[3.1.1]heptan-3-ol

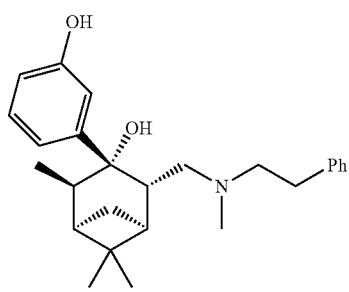 [SMILES: C[C@@H]1[C@H]2C[C@@H]([C@@H](CN(C)CCc3ccccc3)[C@]1(O)c1cccc(O)c1)C2(C)C]

Add a solution of t-BuLi (20 mL, 26.0 mmol) via syringe to a solution of 3-bromo-phenol (2.06 g, 12 mmol) in THF (20 mL) at −78° C. under N$_2$. After being stirred at −78° C. for 1 hour, add a solution of (1R,2R,4S,5S)-2,6,6-trimethyl-4-((methyl(phenethyl)amino)methyl)bicyclo[3.1.1]heptan-3-one (2.99 g, 10 mmol) in THF (2 mL) to the reaction mixture and stir the reaction mixture at −78° C. for additional 2 hours. Quench the reaction with saturated NH$_4$Cl solution (30 mL). Extract the aqueous mixture with EtOAc (60 mL×3). The combined organic layers are washed with brine (30 mL), dried over Na$_2$SO$_4$, filtered, and concentrated under vacuum. Purify the residue by Preparative HPLC to give (1R,2R,3S,4S,5S)-3-(3-hydroxyphenyl)-2,6,6-trimethyl-4-((methyl (phenethyl)amino)methyl)bicyclo[3.1.1]heptan-3-ol as pale yellow oil (0.27 g, yield: 6.9%), MS (m/z): 394 (M+1).

The following compound may be prepared essentially by the method of Example 169.

| Prep No. | Chemical name | Structure | Physical data |
|---|---|---|---|
| 168 | (1S,2S,4R,5R)-2,6,6-trimethyl-4-((methyl (phenethyl)amino)methyl) bicyclo[3.1.1]heptan-3-one | 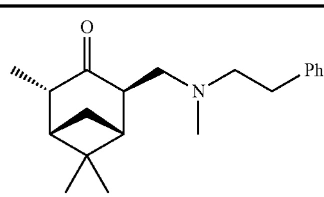 | MS (m/z): 300 (M + 1). |

| Ex. No. | Chemical name | Structure | Physical data |
|---|---|---|---|
| 170 | (1R,2R,3S,4S,5S)-3-(3-methoxyphenyl)-2,6,6-trimethyl-4-((methyl(phenethyl)amino)methyl)bicyclo[3.1.1]heptan-3-ol | 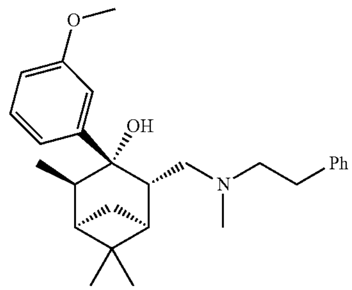 [SMILES: COc1cccc([C@]2(O)[C@H](C)[C@H]3C[C@@H]([C@H]2CN(C)CCc2ccccc2)C3(C)C)c1] | MS (m/z): 408 (M + 1). |
| 171 | (1S,2S,3R,4R,5R)-3-(3-hydroxyphenyl)-2,6,6-trimethyl-4-((methyl(phenethyl)amino)methyl)bicyclo[3.1.1]heptan-3-ol | 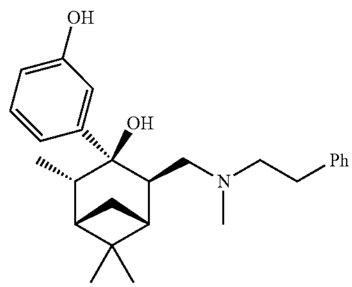 [SMILES: C[C@H]1[C@@H]2C[C@H]([C@H](CN(C)CCc3ccccc3)[C@@]1(O)c1cccc(O)c1)C2(C)C] | MS (m/z): 394 (M + 1). |
| 172 | (1S,2S,3R,4R,5R)-3-(3-methoxyphenyl)-2,6,6-trimethyl-4-((methyl(phenethyl)amino)methyl)bicyclo[3.1.1]heptan-3-ol | 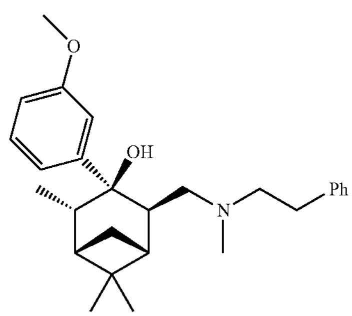 [SMILES: COc1cccc([C@@]2(O)[C@@H](C)[C@@H]3C[C@H]([C@@H]2CN(C)CCc2ccccc2)C3(C)C)c1] | MS (m/z): 408 (M + 1). |

EXAMPLE 173

(1R,2R,3S,4S,5S)-3-(3-hydroxyphenyl)-2,6,6-trimethyl-4-((methyl(phenethyl)amino)methyl)bicyclo[3.1.1]heptan-3-ol hydrochloride

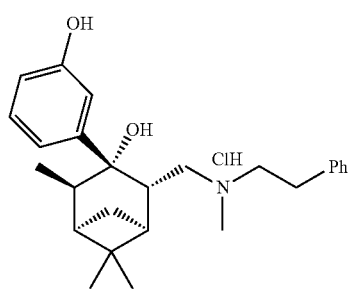 [SMILES: C[C@@H]1[C@H]2C[C@@H]([C@@H](CN(C)CCc3ccccc3)[C@]1(O)c1cccc(O)c1)C2(C)C ; Cl]

Add $H_2O$ (4 mg, 0.25 mmol) and TMSCl (27 mg, 0.25 mmol) to a solution of (1R,2R,3S,4S,5S)-3-(3-hydroxyphenyl)-2,6,6-trimethyl-4-((methyl(phenethyl)amino)methyl)bicyclo[3.1.1]heptan-3-ol (100 mg, 0.25 mmol) in 2-butanone (5 mL). Stir the reaction mixture at room temperature for 3 hours. After removal solvent by evaporation, wash the residue with EtOAc (1 mL×2) and dry under vacuum to give (1R,2R,3S,4S,5S)-3-(3-hydroxyphenyl)-2,6,6-trimethyl-4-((methyl(phenethyl)amino)methyl)bicyclo[3.1.1]heptan-3-ol hydrochloride (93 mg, Yield: 85.3%) as white solid. $^1$H NMR (400 MHz, $D_2O$) δ 7.21-7.32 (m, 7H), 7.97-7.99 (d, J=7.2, 1H), 6.71-6.78 (dd, $J_1$=8.0, $J_2$=22.0, 1H), 2.86-3.33 (m, 5H), 2.43-2.68 (m, 7H), 2.11-2.20 (m, 2H), 1.73-1.75 (m, 1H), 1.23-1.25 (d, J=5.6, 3H), 1.04-1.05 (d, J=4.4, 3H), 0.69-0.71 (d, J=5.6, 3H). $[α]_D^{20}$=−8.6 (c=1.4 mg/mL, MeOH).

The following compounds may be prepared essentially by the method of Example 173.

| Ex. No. | Chemical name | Structure | Physical data |
|---|---|---|---|
| 174 | (1R,2R,3S,4S,5S)-3-(3-methoxyphenyl)-2,6,6-trimethyl-4-((methyl(phenethyl)amino)methyl)bicyclo[3.1.1]heptan-3-ol hydrochloride | 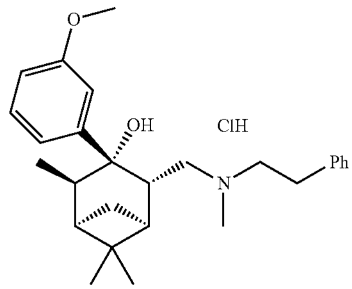 [SMILES: COc1cccc([C@]2(O)[C@H](C)[C@H]3C[C@@H]([C@H]2CN(C)CCc2ccccc2)C3(C)C)c1 ; Cl] | $^1$H NMR (400 MHz, D$_2$O) δ 7.02-7.26 (m, 7H), 6.74-6.86 (m, 2H), 3.64-3.66 (d, J = 10.4, 3H), 2.76-3.22 (m, 5H), 2.32-2.53 (m, 7H), 2.02-2.14 (m, 2H), 1.64-1.67 (m, 1H), 1.14-1.56 (d, J = 6.8, 3H), 0.95-0.97 (d, J = 6.4, 3H), 0.63 (s, 3H). [α] D = −16.1 (c = 6.4 mg/mL, MeOH) |
| 175 | (1S,2S,3R,4R,5R)-3-(3-hydroxyphenyl)-2,6,6-trimethyl-4-((methyl(phenethyl)amino)methyl)bicyclo[3.1.1]heptan-3-ol hydrochloride | 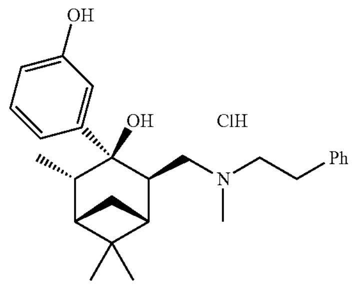 [SMILES: C[C@H]1[C@@H]2C[C@H]([C@H](CN(C)CCc3ccccc3)[C@@]1(O)c1cccc(O)c1)C2(C)C ; Cl] | MS (m/z): 394 (M + 1). [α] D = 9.3 (c = 4.5 mg/mL, MeOH) |
| 176 | (1S,2S,3R,4R,5R)-3-(3-methoxyphenyl)-2,6,6-trimethyl-4-((methyl(phenethyl)amino)methyl)bicyclo[3.1.1]heptan-3-ol hydrochloride | 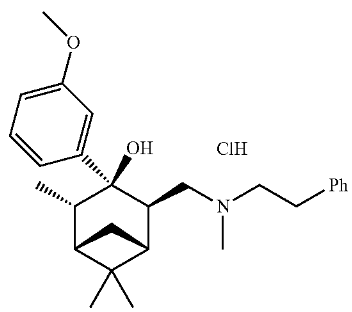 [SMILES: COc1cccc([C@@]2(O)[C@@H](C)[C@@H]3C[C@H]([C@@H]2CN(C)CCc2ccccc2)C3(C)C)c1 ; Cl] | MS (m/z): 408 (M + 1). [α] D = 14.3 (c = 6.0 mg/mL, MeOH) |

For compounds of the formula If, below, Scheme L and Preparations and/or Examples 177-180 illustrate methods of preparing them.

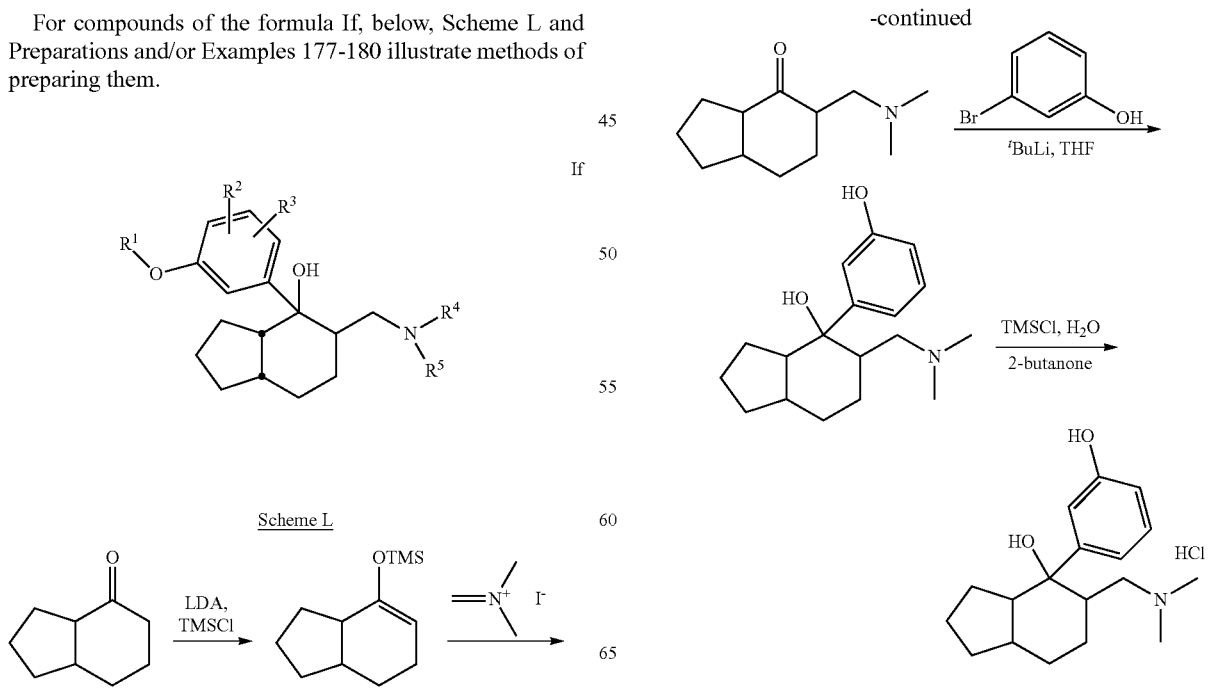

Scheme L

PREPARATION 177

Synthesis of (2,3,3a,6,7,7a-hexahydro-1H-inden-4-yloxy)trimethylsilane

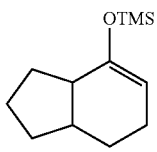

Add dropwise hexahydro-1H-inden-4(2H)-one (1.6 g, 11.6 mmol) in dry THF (5 mL) to a solution of LDA (23.2 mL, 23.2 mmol) in THF (30 mL). Stir the reaction mixture for 30 min and then add dropwise TMSCl (3.5 g, 32.0 mmol) to the reaction mixture. Stir the resultant solution for additional 1 hour. Pour the mixture into ice water (50 mL) and extract the aqueous mixture with EtOAc (50 mL×3). The combined organic layers are washed with brine, dried over MgSO$_4$, filtered and concentrated in vacuo to afford crude (2,3,3a,6,7,7a-hexahydro-1H-inden-4-yloxy)trimethylsilane (2.45 g, 100%) as yellowish oil, MS (m/z): 209 (M−1).

PREPARATION 178

5-((dimethylamino)methyl)hexahydro-1H-inden-4(2H)-one

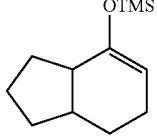

Add (2,3,3a,6,7,7a-hexahydro-1H-inden-4-yloxy)trimethylsilane (2.45 g, 11.6 mmol) to a cooled suspension of N,N-dimethylmethyleneiminium iodide (2.78 g, 15.0 mmol) in CH$_2$Cl$_2$ (60 mL) at 0° C. After being stirred for overnight at ambient temperature, dilute the reaction mixture with 2 N HCl (20 mL). After removal of organic layers, wash the aqueous layer with EtOAc (30 mL×3) and then basify with NaOH to PH=10. Extract the resultant mixture with EtOAc (50 mL×4). The combined organic layers are washed with brine, dried over Na$_2$SO$_4$, filtered and concentrated in vacuo to afford 5-((dimethylamino)methyl)hexahydro-1H-inden-4(2H)-one (623 mg, 27.5%) as oil, MS (m/z): 196 (M+1).

EXAMPLE 179

5-((dimethylamino)methyl)-4-(3-hydroxyphenyl)octahydro-1H-inden-4-ol

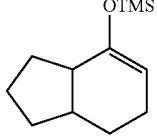

Add a solution of t-BuLi (2.1 mL, 3.07 mmol) via syringe to a solution of 3-bromo-phenol (569 mg, 3.076 mmol) in THF (50 mL) at −78° C. under N$_2$. After being stirred at −78° C. for 1 hour, add a solution of 35-((dimethylamino)methyl)hexahydro-1H-inden-4(2H)-one (300 mg, 1.54 mmol) in THF (2 mL) to the reaction mixture and stir the reaction mixture at −78° C. for additional 2 hours. Quench the reaction mixture with saturated NH$_4$Cl solution (30 mL). Extract the aqueous resultant mixture with EtOAc (50 mL×3). The combined organic layers are washed with brine (30 mL), dried over Na$_2$SO$_4$, filtered, and concentrated under vacuum. Purify the residue by Preparative HPLC to give 5-((dimethylamino)methyl)-4-(3-hydroxyphenyl)octahydro-1H-inden-4-ol (92 mg, yield: 19.7%). MS (m/z): 290 (M+1).

EXAMPLE 180

5-((dimethylamino)methyl)-4-(3-hydroxyphenyl)octahydro-1H-inden-4-ol hydrochloride

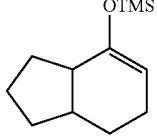

Add H$_2$O (10 mg, 0.54 mmol) and TMSCl (35 mg, 0.33 mmol) to a solution of 5-((dimethylamino)methyl)-4-(3-hydroxyphenyl)octahydro-1H-inden-4-ol (78 mg, 0.27 mmol) in 2-butanone (10 mL). Then stir the mixture at room temperature for 12 hours. Evaporate the mixture under vacuum to give 5-((dimethylamino)methyl)-4-(3-hydroxyphenyl)octahydro-1H-inden-4-ol hydrochloride as a mixture of 4 diastereoisomers (91 mg, Yield: 100%).

EXAMPLE 181

(+)-(1S,2R,3R,5R)-2-((dimethylamino)methyl)-3-(3-hydroxyphenyl)bicyclo[3.2.1]octan-3-ol and (−)-(1R,2S,3S,5S)-2-((dimethylamino)methyl)-3-(3-hydroxyphenyl)bicyclo[3.2.1]octan-3-ol

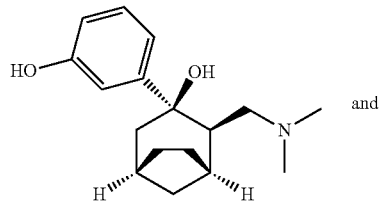

and

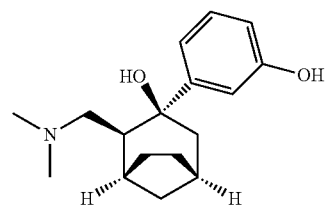

Separate 0.5 g of 2-((dimethylamino)methyl)-3-(3-hydroxyphenyl)bicyclo[3.2.1]octan-3-ol (1.82 mmol) by SFC to afford (+)-(1S,2R,3R,5R)-2-((dimethylamino) methyl)-3-(3-hydroxyphenyl)bicyclo[3.2.1]octan-3-ol (8 mg, Yield: 3.2%; MS (m/z): 276 (M+1)) and (−)-(1R,2S,3S,5S)-2-((dimethylamino)methyl)-3-(3-hydroxyphenyl)bicyclo [3.2.1]octan-3-ol (135 mg, Yield: 54.0%; MS (m/z): 276 (M+1)) as white solids. The relative configuration of two enantioisomers is confirmed by 2D NMR and the absolute configuration of the two enantioisomers is determined by x-ray analysis. (+)-Enantioisomers show better biological activity than (−)-enantioisomer in bioassay(s).

EXAMPLE 182

(S)-3-((1S,2R,3R,5R)-2-((dimethylamino)methyl)-3-hydroxybicyclo[3.2.1]octan-3-yl)phenyl 2-phenylpropanoate hydrochloride

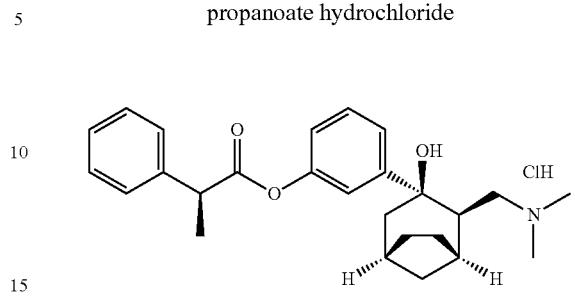

Stir a solution of (S)-2-phenylpropanoic acid (300 mg, 2.0 mmol) in 5 mL of oxalyl chloride for 3 hours at room temperature. After removal of solvent under vacuum, (S)-2-phenylpropanoyl chloride is obtained as pole yellow oil. Dissolve the oil in 10 mL of $CH_2Cl_2$. Add (1S,2R,3R,5R)-2-((dimethylamino)methyl)-3-(3-hydroxyphenyl)bicyclo[3.2.1]octan-3-ol (400 mg, 1.45 mmol) and $Et_3N$ (293 mg, 2.9 mmol) to the solution. Stir the resultant mixture at room temperature for additional 3 hours. After addition of 20 mL of water, basify the mixture with $K_2CO_3$ to pH=10, and extract the aqueous mixture with EtOAc (20 mL×3). The combined organic layers are washed with brine (20 mL), dried over $Na_2SO_4$, filtered, and concentrated under vacuum. Purify the residue by silica gel chromatography ($CH_2Cl_2$:MeOH=30:1) to afford (S)-3-((1S,2R,3R,5R)-2-((dimethylamino)methyl)-3-hydroxybicyclo[3.2.1]octan-3-yl)phenyl 2-phenylpropanoate (500 mg, 84.7%; MS (m/z): 408 (M+1)) as yellow oil. Stir (S)-3-((1S,2R,3R,5R)-2-((dimethylamino)methyl)-3-hydroxybicyclo[3.2.1]octan-3-yl)phenyl 2-phenylpropanoate (250 mg, 0.61 mmol) with $H_2O$ (11 mg, 0.61 mmol) and TMSCl (66 mg, 0.61 mmol) in 2-butanone (5 mL) for 3 hours. Collect the precipitate by filtration to afford (S)-3-((1S,2R,3R,5R)-2-((dimethylamino)methyl)-3-hydroxybicyclo [3.2.1]octan-3-yl)phenyl 2-phenylpropanoate hydrochlorid (215 mg, Yield: 79.3%) as white solid. The absolute configuration of its hydrochloride salt form was confirmed by x-ray analysis. $^1$H NMR (400 MHz, DMSO) δ 9.81 (br, 1H), 7.31-7.41 (m, 7H), 7.14 (s, 1H), 6.87-6.90 (m, 1H), 5.01 (s, 1H), 4.08-4.10 (m, 1H), 3.02-3.08 (m, 1H), 2.42-2.58 (m, 4H), 2.12-2.26 (m, 6H), 1.90-1.99 (m, 2H), 1.75-1.80 (m, 2H), 1.51-1.59 (m, 6H).

The following compound may be prepared essentially by the method of Example 182.

| Ex. No | Chemical name | Structure | Physical data |
|---|---|---|---|
| 183 | (S)-3-((1R,2S,3S,5S)-2-((dimethylamino)methyl)-3-hydroxybicyclo[3.2.1]octan-3-yl)phenyl 2-phenylpropanoate hydrochloride | 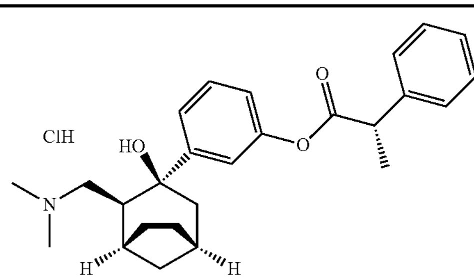 | $^1$H NMR (400 MHz, DMSO) δ 9.78 (br, 1H), 7.34-7.47 (m, 7H), 7.23 (s, 1H), 6.91-6.93 (m, 1H), 5.14 (s, 1H), 4.13-4.18 (m, 1H), 3.09-3.15 (m, 1H), 2.48-2.65 (m, 4H), 2.17-2.32 (m, 6H), 1.97-2.06 (m, 2H), 1.81-1.86 (m, 2H), 1.49-1.66 (m, 6H). |

EXAMPLE 184

3-(4-dimethylaminomethyl-bicyclo[3.2.1]oct-2-en-3-yl)-phenol and 3-((1S,5R)-2-((dimethylamino)methyl)bicyclo[3.2.1]oct-2-en-3-yl)phenol

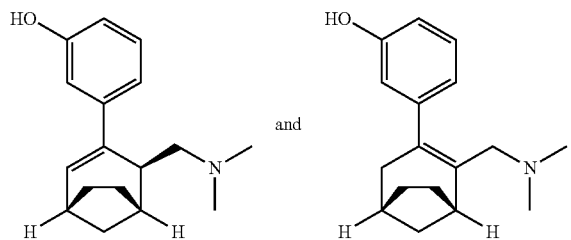 [SMILES: CN(C)C[C@@H]1C(c2cccc(O)c2)=C[C@@H]2CC[C@H]1C2 ; CN(C)CC1=C(c2cccc(O)c2)C[C@@H]2CC[C@H]1C2]

Add TsOH (5.0 g, 29.1 mmol) to a solution of 2-dimethylaminomethyl-3-(3-hydroxy-phenyl)-bicyclo[3.2.1]octan-3-ol (4.8 g, 17.5 mmol) in toluene (150 mL). Heat the reaction mixture to reflux for 2 hours and then quench the reaction by addition of saturated aqueous K₂CO₃ (20 mL). Extract the aqueous layer with EtOAc (60 mL×3). The combined organic layers are washed with brine, dried over Na₂SO₄ and evaporated under vacuum. Purify the residue by preparative HPLC to yield 3-(4-dimethylaminomethyl-bicyclo[3.2.1]oct-2-en-3-yl)-phenol (2.27 g, 50.2%; MS (m/z): 258 (M+1)) and 3-(2-((dimethylamino)methyl)bicyclo[3.2.1]oct-2-en-3-yl)phenol (517 mg, 11.5%; MS (m/z): 258 (M+1)) as white solid. Two isomers show comparable biological activity in bioassay.

For compounds of the formula Ig, below, Scheme M and Preparations and/or Examples 185-187 illustrate methods of preparing them.

Ig

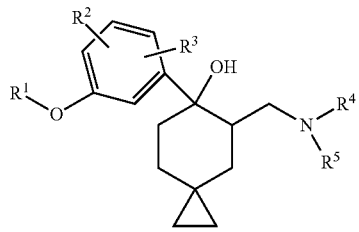

Scheme M

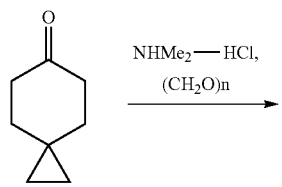

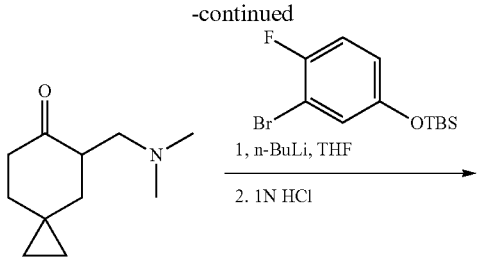

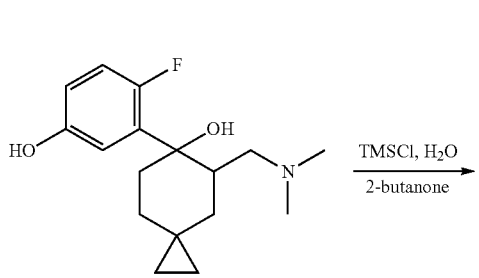

PREPARATION 185

5-dimethylaminomethyl-spiro[2.5]octan-6-one

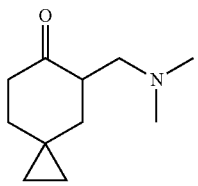

Stir a mixture of spiro[2.5]octan-6-one (252 mg, 2.03 mmol), (HCHO)ₙ (61 mg, 2.03 mmol), dimethylamine hydrochloride (166 mg, 2.03 mmol) and 0.3 mL of conc. HCl in MeCN (30 mL) at 60° C. for 6 hours. Quench the reaction with saturated aqueous NH₄Cl solution (15 mL). Basify the aqueous solution with K₂CO₃ to pH=9. Extract the aqueous mixture with EtOAc (30 mL×2). The combined organic layers are washed with brine (15 mL), dried over Na₂SO₄, filtered, and concentrated under vacuum. Purify the residue by silica gel chromatography (CH₂Cl₂:MeOH=30:1) to afford 5-Dimethylaminomethyl-spiro[2.5]octan-6-one as brown oil (142 mg, yield: 38.4%). MS (m/z): 182 (M+1).

EXAMPLE 186

5-dimethylaminomethyl-6-(2-fluoro-5-hydroxy-phenyl)-spiro[2.5]octan-6-ol

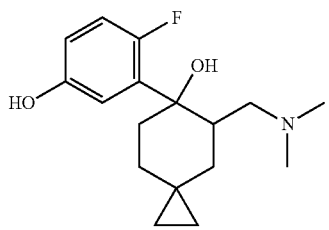 [SMILES: CN(C)CC1CC2(CC2)CCC1(O)c1cc(O)ccc1F]

Cool a solution of (3-bromo-4-fluoro-phenoxy)-tert-butyl-dimethyl-silane (472 mg, 1.547 mmol) in THF (40 mL) to −78° C. under $N_2$. Then add dropwise a solution of n-BuLi (0.63 mL, 1.547 mmol) in hexane via syringe to the reaction solution. After being stirred at −78° C. for 2 hour, add dropwise a solution of 5-Dimethylaminomethyl-spiro[2.5]octan-6-one (70 mg, 0.387 mmol) in THF (1 mL) to the reaction mixture and stir the mixture at −78° C. for additional 2 hours. Quench the reaction with 20 mL of diluted HCl (2N), and stir at ambient temperature for 2 hours. Basify the resultant mixture with $K_2CO_3$ to pH=9, and extract with EtOAc (30 mL×2). The combined organic layers are washed with brine, dried over $Na_2SO_4$, filtered, and concentrated under vacuum. Purify the residue by silica gel chromatography ($CH_2Cl_2$ to $CH_2Cl_2$:MeOH=10:1) to afford 5-dimethylaminomethyl-6-(2-fluoro-5-hydroxy-phenyl)-spiro[2.5]octan-6-ol as white solid (41 mg, yield: 36.3%). MS (m/z): 294 (M+1).

EXAMPLE 187

5-dimethylaminomethyl-6-(2-fluoro-5-hydroxy-phenyl)-spiro[2.5]octan-6-ol hydrochloride

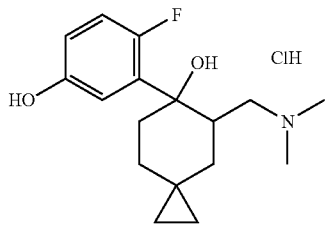 [SMILES: CN(C)CC1CC2(CC2)CCC1(O)c1cc(O)ccc1F ; Cl]

Add $H_2O$ (9 mg, 0.500 mmol) and TMSCl (18 mg, 0.167 mmol) to a solution of 5-dimethylaminomethyl-6-(2-fluoro-5-hydroxy-phenyl)-spiro[2.5]octan-6-ol (41 mg, 0.139 mmol) in 2-butanone (30 mL). Stir the mixture at 0° C. for 2 hours. Concentrate the mixture under vacuum to give 5-dimethylaminomethyl-6-(2-fluoro-5-hydroxy-phenyl)-spiro[2.5]octan-6-ol hydrochloride as white solid (46 mg, Yield: 100%). $^1$H NMR (400 MHz, $D_2O$) δ 7.13-7.15 (d, $J_1$=6.8, $J_2$=3.2, 1H), 6.93-6.98 (d, $J_1$=12.0, $J_2$=8.8, 1H), 6.69-6.73 (m, 1H), 3.05-3.10 (m, 1H), 2.65-2.76 (m, 8H), 2.44-2.45 (m, 1H), 2.27-2.35 (m, 2H), 1.70-1.74 (m, 1H), 0.96-0.98 (m, 1H), 0.79-0.82 (m, 1H), 0.45 (m, 1H).

Mu opioid agonists, such as morphine, are well known to control pain (Tschenkte et al., Tapentadol Hydrochloride—Analgesic, Mu-opioid receptor agonist, Noradrenaline reuptake inhibitor. E. Drugs Fut 2006, 31(12): 1053). However, mu opioid agonists also can cause several undesired side effects such as nausea, emesis, constipation, mental clouding, and respiratory depression. In addition, use of opioids for an extended period of time (as is needed in chronic pain) can result in physical dependence and addiction.

Tramadol, a mu-opioid agonist, has not been associated with clinically significant side effects such as respiratory depression, constipation, or sedation (Id.). In addition, extended use of Tramadol does not lead to tolerance, dependence, and addiction (Id.). Tramadol is believed to exert its chronic pain relief through a combination of three mechanisms of action; mu opioid agonism and serotonin and norepinephrine reuptake inhibition (Raffa et al., Opioid and nonopioid components independently contribute to the mechanism of action of tramadol, an 'atypical' opioid analgesic. J Pharmacol Exp Ther. 1992 January; 260(1):275-85). Because Tramadol relieves pain through a combination of mechanisms of action it is able to relieve pain even though it is a much less potent mu opioid receptor agonist compared to morphine. The reason for the better side effect profile of Tramadol as compared to morphine is believed to be a result of Tramadol's lower affinity for the mu opioid receptor. A molecule that, like Tramadol, controls chronic pain by multiple mechanisms of action is desired, and a compound which possessed a favorable side effect profile, particularly as compared to morphine, and that also was longer acting was sought. Preferably, a molecule that needed to be administered at most 1 time per day for extended pain relief is sought.

Molecules that are mu opioid agonists and also norepinephrine and/or serotonin reuptake inhibitors are preferably selected for evaluation in the rat tail flick model. In order to be selected for the rat tail flick model the compound needs to demonstrate an EC50 of less than 50 micromolar in a functional assay for mu opioid receptor activation. In addition, the active species needs to demonstrate an IC50 of less than 500 micromolar in a functional assay for inhibition of norepinephrine and/or serotonin reuptake. Activity of the corresponding phenols are used to select ether and ester prodrugs for evaluation in the rat tail flick model.

The Tail Flick Assay, based upon the methods of D'Amour & Smith (J. Pharmacol. Exp. Therap., 72: 74-79, 1941), is used to measure loss of pain sensation in the rat tail, allowing the experimenter to screen drugs for analgesic effect. Since then, the method has been used in a number of publications. For example, it was used to evaluate the analgesic effect of O-alkyl derivatives of tramadol by Liming Shao and Michael Hewitt etc. (Boiorganic & Medicinal Chemistry Letters, 18:1674-1680, 2008).

A Tail Flick Unit is used to measure tail flick latency in response to heat. The unit consists of an infrared (I.R.) source (50 W bulb) with adjustable intensity that is focused through a flush mounted window on the upper panel of the unit and onto the rat tail. Once I.R. source is focused on the rat tail and turned on, a timer starts. When the thermal threshold for pain is reached and the rat flicks its tail, the I.R source automatically shuts off and the timer stop, displaying the latency time.

On the day of experiment, the animals are tested to determine baseline latency. Each rat is given one test to determine latency to tail flick with a cut off 10 seconds. Baselines are recorded and those animals with a baseline latency of 2-5 seconds are used in the experiment. Animals are divided into several groups according to the baseline latency. The Tail-flick latencies are measured at different timepoints for up to 180 minutes after administration of vehicle or test articles. If treatment group continues to display pain control after 180 minutes, additional measurements are taken every 60 minutes until pain control is no longer observed.

I.R. Source is set at 40 units (determined to elicit tail flick response in desired 2-5 seconds in naïve animals). A cut off time of 10 seconds is set to avoid tissue damage, in the event that the animal does not flick its tail.

Test articles or vehicle are administered by intravenous (IV) injection through the tail vein or by oral gavage at time 0. Animals are gently restrained and held on top of a tail flick unit. The tail is then wiped clean with a cotton square and placed over the I.R. source so that the beam is focused at approximately midway the length of the tail. After the rat is in position, the I.R. source is turned on. When the thermal threshold for pain is reached, the rat flicked its tail and the I.R. source automatically shuts off. Latency time (in seconds) is then recorded.

Data are recorded and graphed as % MPE (Maximum Possible Effect). % MPE is calculated using the following formula:

% MPE=[(Test latency−Baseline latency)/(Cut off latency(10 sec.'s)−Baseline latency)]*100

Compounds were administered by the IV route in 20% 2-hydroxypropyl-beta-cyclodextrin (20% HP-β-CD). The dose levels of test article were 2.5, 5, or 20 mg/kg. Examples 2, 3, 13, 40, 77, 78, 114, and Tramadol provided at least 50% MPE at 20 mg/kg. Compounds 5, 8, 17, 105, 107, 148, 158, and 159 provided at least 50% MPE at 5 mg/kg. Compounds 82, 84, and 116 provided at least 50% MPE at 2.5 mg/kg.

Compounds were administered by oral gavage in 0.5% methylcellulose at 20 or 30 mg/kg. Examples 2, 3, 13, 115, and Tramadol provided at least 50% MPE at 30 mg/kg. Compounds 5, 39, 65, 106, and 115 provided at least 50% MPE at 20 mg/kg.

The data above supports the contention the compounds are useful in controlling pain.

We claim:

1. A compound, or salt thereof, of formula I:

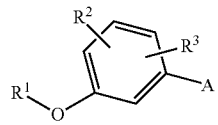

I wherein A is

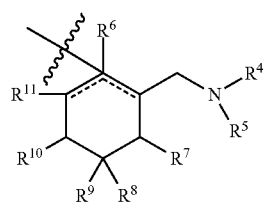

$R^1$ is hydrogen, $C_1$-$C_5$ alkyl, $C_1$-$C_5$ haloalkyl, $C_1$-$C_5$ alkanol, —($C_1$-$C_5$ alkyl)phenyl, or phenyl, or a group of the formula —C(O)—$R^{12}$, where $R^{12}$ is $C_1$-$C_5$ alkyl, $C_1$-$C_5$ alkoxy, $C_1$-$C_5$ haloalkyl, $C_1$-$C_5$ alkanol, —($C_1$-$C_5$ alkyl)phenyl, or phenyl;

$R^2$ is hydrogen, $C_1$-$C_5$ alkyl, $C_1$-$C_5$ alkoxy, halogen, $C_1$-$C_5$ haloalkyl, or $C_1$-$C_5$ haloalkoxy;

$R^3$ is hydrogen, $C_1$-$C_5$ alkyl, $C_1$-$C_5$ alkoxy, halogen, $C_1$-$C_5$ haloalkyl, or $C_1$-$C_5$ haloalkoxy;

$R^4$ is hydrogen, $C_1$-$C_5$ alkyl, or —($C_1$-$C_5$ alkyl)phenyl;

$R^5$ is hydrogen, $C_1$-$C_5$ alkyl, or —($C_1$-$C_5$ alkyl)phenyl;

$R^6$ is hydrogen, hydroxy, or is absent;

$R^7$ is hydrogen;

$R^8$ is hydrogen or methyl;

$R^9$ is hydrogen or methyl;

$R^{10}$ is hydrogen;

$R^{11}$ is hydrogen or $C_1$-$C_5$ alkyl;

provided that one of A), B), and C) is present, wherein A), B) and C) are:

A) $R^7$ and $R^{10}$ combine to form —$CH_2$— or —($CH_2$)$_2$—;

B) $R^8$ and $R^9$ combine to form a cyclopropyl group with the carbon to which they are attached; and C) $R^{10}$ and $R^{11}$ combine to form —$CH_2$— or —($CH_2$)$_3$.

2. The compound of claim 1 wherein A is selected from

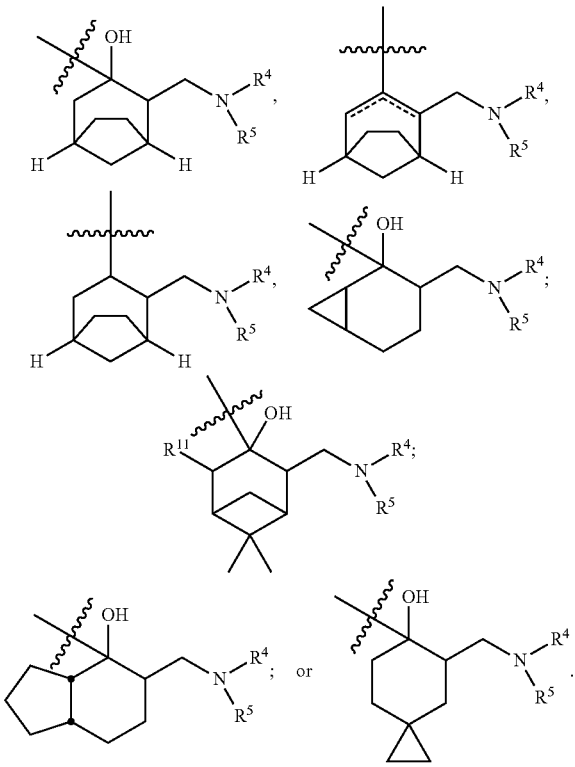

3. The compound of claim 2 of the formula Ia:

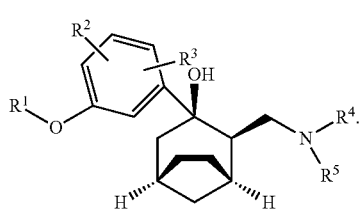

Ia or a salt thereof.

4. The compound of claim 2 wherein it is
2-dimethylaminomethyl-3-(3-methoxy-phenyl)-bicyclo[3.2.1]octan-3-ol;
2-dimethylaminomethyl-3-(3-fluoro-5-methoxy-phenyl)-bicyclo[3.2.1]octan-3-ol;
2-dimethylaminomethyl-3-(5-methoxy-2-trifluoromethoxy-phenyl)-bicyclo[3.2.1]octan-3-ol;
2-dimethylaminomethyl-3-(2-fluoro-5-methoxy-phenyl)-bicyclo[3.2.1]octan-3-ol;
2-dimethylaminomethyl-3-(4-fluoro-3-methoxy-phenyl)-bicyclo[3.2.1]octan-3-ol;
2-dimethylaminomethyl-3-(2-fluoro-3-methoxy-phenyl)-bicyclo[3.2.1]octan-3-ol;
2-dimethylaminomethyl-3-(3-methoxy-5-methyl-phenyl)-bicyclo[3.2.1]octan-3-ol;
3-(2-chloro-5-methoxy-phenyl)-2-dimethylaminomethyl-bicyclo[3.2.1]octan-3-ol;
3-(3-chloro-5-methoxyphenyl)-2-dimethylaminomethyl-bicyclo[3.2.1]octan-3-ol;
2-dimethylaminomethyl-3-(5-methoxy-2-methyl-phenyl)-bicyclo[3.2.1]octan-3-ol;
2-dimethylaminomethyl-3-(3-methoxy-4-methyl-phenyl)-bicyclo[3.2.1]octan-3-ol;
2-dimethylaminomethyl-3-(3-hydroxy-phenyl)-bicyclo[3.2.1]octan-3-ol;
2-dimethylaminomethyl-3-(2-fluoro-5-hydroxy-phenyl)-bicyclo[3.2.1]octan-3-ol;
2-dimethylaminomethyl-3-(3-fluoro-5-hydroxy-phenyl)-bicyclo[3.2.1]octan-3-ol;
2-dimethylaminomethyl-3-(3-hydroxy-5-trifluoromethyl-phenyl)-bicyclo[3.2.1]octan-3-ol;
2-dimethylaminomethyl-3-(5-hydroxy-2-trifluoromethoxy-phenyl)-bicyclo[3.2.1]octan-3-ol;
2-dimethylaminomethyl-3-(3-hydroxy-4-trifluoromethyl-phenyl)-bicyclo[3.2.1]octan-3-ol;
2-dimethylaminomethyl-3-(4-fluoro-3-hydroxy-phenyl)-bicyclo[3.2.1]octan-3-ol;
2-dimethylaminomethyl-3-(2-fluoro-3-hydroxy-phenyl)-bicyclo[3.2.1]octan-3-ol;
2-dimethylaminomethyl-3-(3-hydroxy-5-methyl-phenyl)-bicyclo[3.2.1]octan-3-ol;
3-(2-chloro-5-hydroxy-phenyl)-2-dimethylaminomethyl-bicyclo[3.2.1]octan-3-ol;
3-(3-chloro-5-hydroxy-phenyl)-2-dimethylaminomethyl-bicyclo[3.2.1]octan-3-ol;
2-dimethylaminomethyl-3-(5-hydroxy-2-methyl-phenyl)-bicyclo[3.2.1]octan-3-ol;
2-dimethylaminomethyl-3-(3-hydroxy-4-methyl-phenyl)-bicyclo[3.2.1]octan-3-ol;
3-(3,4-difluoro-5-hydroxy-phenyl)-2-dimethylaminomethyl-bicyclo[3.2.1]octan-3-ol;
2-dimethylaminomethyl-3-(2-fluoro-5-hydroxy-phenyl)-bicyclo[3.2.1]octan-3-ol;
2,2-dimethyl-propionic acid 3-(2-dimethylaminomethyl-3-hydroxy-bicyclo[3.2.1]oct-3-yl)-4-fluoro-phenyl ester;
benzoic acid 3-(2-dimethylaminomethyl-3-hydroxy-bicyclo[3.2.1]oct-3-yl)-4-fluoro-phenyl ester;
2,2-dimethyl-propionic acid 3-(2-dimethylaminomethyl-3-hydroxy-bicyclo[3.2.1]oct-3-yl)-phenyl ester;
benzoic acid 3-(2-dimethylaminomethyl-3-hydroxy-bicyclo[3.2.1]oct-3-yl)-phenyl ester;
2,2-dimethyl-propionic acid 3-(2-dimethylaminomethyl-3-hydroxy-bicyclo[3.2.1]oct-3-yl)-5-fluoro-phenyl ester; or
benzoic acid 3-(2-dimethylaminomethyl-3-hydroxy-bicyclo[3.2.1]oct-3-yl)-5-fluoro-phenyl ester;
or a salt thereof.

5. The compound of claim 2 of the formula Ib:

or a salt thereof.

6. The compound of claim 2 wherein it is
3-(4-dimethylaminomethyl-bicyclo[3.2.1]oct-2-en-3-yl)-phenol;
[3-(3-methoxy-phenyl)-bicyclo[3.2.1]oct-3-en-2-ylmethyl]-dimethyl-amine;
[3-(5-methoxy-2-trifluoromethoxy-phenyl)-bicyclo[3.2.1]oct-3-en-2-ylmethyl]-dimethyl-amine;
3-(4-dimethylaminomethyl-bicyclo[3.2.1]oct-2-en-3-yl)-4-trifluoromethoxy-phenol;
[3-(3-fluoro-5-methoxy-phenyl)-bicyclo[3.2.1]oct-3-en-2-ylmethyl]-dimethyl-amine;
3-(4-dimethylaminomethyl-bicyclo[3.2.1]oct-2-en-3-yl)-5-fluoro-phenol;
[3-(2-fluoro-5-methoxy-phenyl)-bicyclo[3.2.1]oct-3-en-2-ylmethyl]-dimethyl-amine;
3-(4-dimethylaminomethyl-bicyclo[3.2.1]oct-2-en-3-yl)-4-fluoro-phenol;
[3-(3-methoxy-5-methyl-phenyl)-bicyclo[3.2.1]oct-3-en-2-ylmethyl]-dimethyl-amine;
3-(4-dimethylaminomethyl-bicyclo[3.2.1]oct-2-en-3-yl)-5-methyl-phenol;
3-chloro-5-(4-dimethylaminomethyl-bicyclo[3.2.1]oct-2-en-3-yl)-phenol;
[3-(5-methoxy-2-methyl-phenyl)-bicyclo[3.2.1]oct-3-en-2-ylmethyl]-dimethyl-amine;
3-(4-dimethylaminomethyl-bicyclo[3.2.1]oct-2-en-3-yl)-4-methyl-phenol;
4-chloro-3-(4-dimethylaminomethyl-bicyclo[3.2.1]oct-2-en-3-yl)-phenol;
2,2-dimethyl-propionic acid 3-(4-dimethylaminomethyl-bicyclo[3.2.1]oct-2-en-3-yl)-phenyl ester;
benzoic acid 3-(4-dimethylaminomethyl-bicyclo[3.2.1]oct-2-en-3-yl)-phenyl ester;
2,2-dimethyl-propionic acid 3-(4-dimethylaminomethyl-bicyclo[3.2.1]oct-2-en-3-yl)-5-fluorophenyl ester;
isobutyric acid 3-(4-dimethylaminomethyl-bicyclo[3.2.1]oct-2-en-3-yl)-5-fluoro-phenyl ester;
2,2-dimethyl-propionic acid 3-(4-dimethylaminomethyl-bicyclo[3.2.1]oct-2-en-3-yl)-4-fluoro-phenyl ester; or
isobutyric acid 3-(4-dimethylaminomethyl-bicyclo[3.2.1]oct-2-en-3-yl)-4-fluoro-phenyl ester;
or a salt thereof.

7. The compound of claim 2 wherein it is of the formula Ic:

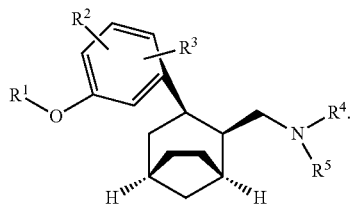

Ic or a salt thereof.

8. The compound of claim 2 wherein it is:
3-(2-dimethylaminomethyl-bicyclo[3.2.1]oct-3-yl)-phenol;
[3-(3-methoxy-phenyl)-bicyclo[3.2.1]oct-2-ylmethyl]-dimethyl-amine;
3-(2-dimethylaminomethyl-bicyclo[3.2.1]oct-3-yl)-5-fluoro-phenol;
[3-(3-fluoro-5-methoxy-phenyl)-bicyclo[3.2.1]oct-2-ylmethyl]-dimethyl-amine;
3-(2-dimethylaminomethyl-bicyclo[3.2.1]oct-3-yl)-4-fluoro-phenol;
[3-(2-fluoro-5-methoxy-phenyl)-bicyclo[3.2.1]oct-2-ylmethyl]-dimethyl-amine;
3-(2-dimethylaminomethyl-bicyclo[3.2.1]oct-3-yl)-5-methyl-phenol;
[3-(3-methoxy-5-methyl-phenyl)-bicyclo[3.2.1]oct-2-ylmethyl]-dimethyl-amine;
2,2-dimethyl-propionic acid 3-(2-dimethylaminomethyl-bicyclo[3.2.1]oct-3-yl)-phenyl ester;
benzoic acid 3-(2-dimethylaminomethyl-bicyclo[3.2.1]oct-3-yl)-phenyl ester;
2,2-dimethyl-propionic acid 3-(2-dimethylaminomethyl-bicyclo[3.2.1]oct-3-yl)-5-fluoro-phenyl ester;
isobutyric acid 3-(2-dimethylaminomethyl-bicyclo[3.2.1]oct-3-yl)-5-fluoro-phenyl ester;
2,2-dimethyl-propionic acid 3-(2-dimethylaminomethyl-bicyclo[3.2.1]oct-3-yl)-4-fluoro-phenyl ester;
or isobutyric acid 3-(2-dimethylaminomethyl-bicyclo[3.2.1]oct-3-yl)-4-fluoro-phenyl ester;
or a salt thereof.

9. The compound of claim 2 wherein it is of the formula Id:

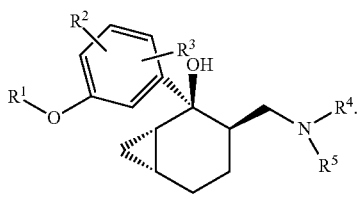

Id or a salt thereof.

10. The compound of claim 2 wherein it is
3-dimethylaminomethyl-2-(3-hydroxy-phenyl)-bicyclo[4.1.0]heptan-2-ol;
3-dimethylaminomethyl-2-(3-methoxy-phenyl)-bicyclo[4.1.0]heptan-2-ol;
3-dimethylaminomethyl-2-(3-fluoro-5-methoxy-phenyl)-bicyclo[4.1.0]heptan-2-ol;
3-dimethylaminomethyl-2-(5-methoxy-2-methyl-phenyl)-bicyclo[4.1.0]heptan-2-ol;
3-dimethylaminomethyl-2-(3-methoxy-phenyl)-5,5-dimethyl-bicyclo[4.1.0]heptan-2-ol;
3-dimethylaminomethyl-2-(3-hydroxy-phenyl)-5,5-dimethyl-bicyclo[4.1.0]heptan-2-ol;
3-dimethylaminomethyl-2-(3-fluoro-5-hydroxy-phenyl)-bicyclo[4.1.0]heptan-2-ol;
3-dimethylaminomethyl-2-(2-fluoro-5-hydroxy-phenyl)-bicyclo[4.1.0]heptan-2-ol;
3-dimethylaminomethyl-2-(3-hydroxy-5-methyl-phenyl)-bicyclo[4.1.0]heptan-2-ol;
2,2-dimethyl-propionic acid 3-(3-dimethylaminomethyl-2-hydroxy-bicyclo[4.1.0]hept-2-yl)-5-fluoro-phenyl ester; or
2,2-dimethyl-propionic acid 3-(3-dimethylaminomethyl-2-hydroxy-bicyclo[4.1.0]hept-2-yl)-4-fluoro-phenyl ester;
or a salt thereof.

11. The compound of claim 2 wherein it is of the formula Ie:

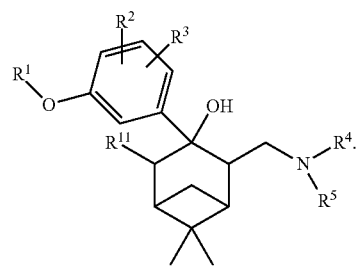

Ie or a salt thereof.

12. The compound of claim 11 wherein it is
(1R,2R,3S,4S,5S)-3-(3-hydroxyphenyl)-2,6,6-trimethyl-4-((methyl(phenethyl)amino)methyl)bicyclo[3.1.1]heptan-3-ol;
(1R,2R,3S,4S,5S)-3-(3-methoxyphenyl)-2,6,6-trimethyl-4-((methyl(phenethyl)amino)methyl)bicyclo[3.1.1]heptan-3-ol;
(1S,2S,3R,4R,5R)-3-(3-hydroxyphenyl)-2,6,6-trimethyl-4-((methyl(phenethyl)amino)methyl)bicyclo[3.1.1]heptan-3-ol;
(1S,2S,3R,4R,5R)-3-(3-methoxyphenyl)-2,6,6-trimethyl-4-((methyl(phenethyl)amino)methyl)bicyclo[3.1.1]heptan-3-ol;
or a salt thereof.

13. The compound of claim 2 wherein it is of the formula If:

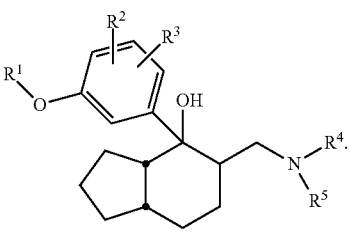

If or a salt thereof.

14. The compound of claim 13 wherein it is 5-((dimethylamino)methyl)-4-(3-hydroxyphenyl)octahydro-1H-inden-4-ol, or a salt thereof.

15. The compound of claim 2 wherein it is (+)-(1S,2R,3R,5R)-2-((dimethylamino)methyl)-3-(3-hydroxyphenyl)bicyclo[3.2.1]octan-3-ol;
- (−)-(1R,2S,3S,5S)-2-((dimethylamino)methyl)-3-(3-hydroxyphenyl)bicyclo[3.2.1]octan-3-ol;
- (S)-3-((1S,2R,3R,5R)-2-((dimethylamino)methyl)-3-hydroxybicyclo[3.2.1]octan-3-yl)phenyl 2-phenylpropanoate hydrochloride;
- (S)-3-(1R,2S,3S,5S)-2-((dimethylamino)methyl)-3-hydroxybicyclo[3.2.1]octan-3-yl)phenyl 2-phenylpropanoate hydrochloride;
- 3-(4-dimethylaminomethyl-bicyclo[3.2.1]oct-2-en-3-yl)-phenol;
- 3-((1S,5R)-2-((dimethylamino)methyl)bicyclo[3.2.1]oct-2-en-3-yl)phenol; and salty or a salt thereof.

16. A compound of claim 2 wherein it is of the formula Ig:

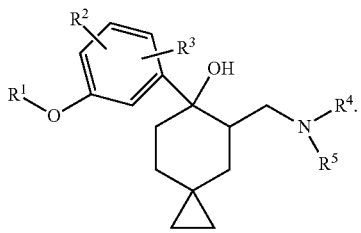

or a salt thereof.

17. The compound of claim 16 where it is 5-dimethylaminomethyl-6-(2-fluoro-5-hydroxy-phenyl)-spiro[2.5]octan-6-ol, or a salt thereof.

18. The compound of claim 4 wherein it is 2-dimethylaminomethyl-3-(3-methoxy-5-methyl-phenyl)-bicyclo[3.2.1]octan-3-ol, or a salt thereof.

19. The compound of claim 4 wherein it is 2-dimethylaminomethyl-3-(3-hydroxy-5-methyl-phenyl)-bicyclo[3.2.1]octan-3-ol, or a salt thereof.

20. The compound of claim 10 wherein it is 3-dimethylaminomethyl-2-(3-fluoro-5-hydroxy-phenyl)-bicyclo[4.1.0]heptan-2-ol, or a salt thereof.

21. The compound of claim 10 wherein it is 3-dimethylaminomethyl-2-(2-fluoro-5-hydroxy-phenyl)-bicyclo[4.1.0]heptan-2-ol, or a salt thereof.

22. The compound of claim 10 wherein it is 2,2-dimethyl-propionic acid 3-(3-dimethylaminomethyl-2-hydroxy-bicyclo[4.1.0]hept-2-yl)-5-fluoro-phenyl ester, or a salt thereof.

23. The compound of claim 10 wherein it is 2,2-dimethyl-propionic acid 3-(3-dimethylaminomethyl-2-hydroxy-bicyclo[4.1.0]hept-2-yl)-4-fluoro-phenyl ester, or a salt thereof.

24. A pharmaceutical formulation comprising a compound claim 2 and one or more pharmaceutically acceptable carriers.

25. The pharmaceutical formulation of claim 24 wherein it further comprises at least one additional active ingredient.

26. The pharmaceutical formulation of claim 24 wherein it is a human pharmaceutical formulation.

27. The pharmaceutical formulation of claim 24 wherein it is a veterinary pharmaceutical formulation.

28. A method of controlling pain in a mammal in need thereof comprising administering an effective amount of a compound of claim 1 to said mammal.

29. The method of claim 28 wherein at least one other active ingredient is administered to said mammal.

30. The method of claim 28 wherein said mammal is a human.

31. The method of claim 28 wherein said mammal is a companion animal.

* * * * *